US006242669B1

(12) United States Patent
Feitelson et al.

(10) Patent No.: US 6,242,669 B1
(45) Date of Patent: Jun. 5, 2001

(54) PESTICIDAL TOXINS AND NUCLEOTIDE SEQUENCES WHICH ENCODE THESE TOXINS

(75) Inventors: Jerald S. Feitelson; H. Ernest Schnepf; Kenneth E. Narva; Brian A. Stockhoff; James Schmeits; David Loewer; Charles Joseph Dullum, all of San Diego; Judy Muller-Cohn, Del Mar; Lisa Stamp, San Diego; George Morrill, El Cajon; Stacey Finstad-Lee, San Diego, all of CA (US)

(73) Assignee: Mycogen Corporation, Indianapolis, IN (US)

( * ) Notice: Subject to any disclaimer, the term of this patent is extended or adjusted under 35 U.S.C. 154(b) by 0 days.

(21) Appl. No.: 09/073,898

(22) Filed: May 6, 1998

Related U.S. Application Data

(63) Continuation-in-part of application No. 08/960,780, filed on Oct. 30, 1997.
(60) Provisional application No. 60/029,848, filed on Oct. 30, 1996.

(51) Int. Cl.[7] .............................. A01H 5/00; C12N 1/21; C12N 15/32; C12N 5/14

(52) U.S. Cl. .......................... 800/295; 800/298; 800/302; 435/252.3; 435/410; 435/418; 536/23.71

(58) Field of Search ............................... 536/23.71, 23.7; 800/295, 298, 302; 435/320.1, 252.3, 410, 418

(56) References Cited

U.S. PATENT DOCUMENTS 4,448,885 5/1984 Schnepf et al. ................. 435/252.33
4,467,036 8/1984 Schnepf et al. ................... 435/320.1
4,797,276 1/1989 Herrnstadt et al. .................. 424/821
4,853,331 8/1989 Herrnstadt et al. ................ 435/252.3
4,918,006 4/1990 Ellar et al. .......................... 435/69.1
4,948,734 8/1990 Edwards et al. ......................... 514/2
4,990,332 2/1991 Payne et al. .................... 424/93.461
5,039,523 8/1991 Payne et al. .................... 424/93.461
5,093,120 3/1992 Edwards et al. ......................... 514/2
5,126,133 6/1992 Payne et al. .................... 424/93.461
5,151,363 9/1992 Payne .............................. 435/252.5
5,164,180 11/1992 Payne et al. .................... 424/93.461
5,169,629 12/1992 Payne et al. .................... 424/93.461
5,204,237 4/1993 Gaertner et al. ......................... 435/6
5,236,843 8/1993 Narva et al. ...................... 435/252.3
5,262,399 11/1993 Hickle et al. ....................... 424/93.2
5,270,448 12/1993 Payne ...................................... 514/2
5,281,530 1/1994 Sick et al. ......................... 435/252.3
5,322,932 6/1994 Narva et al. ......................... 530/350
5,350,577 9/1994 Payne ............................ 424/93.461
5,426,049 6/1995 Sick et al. ......................... 435/252.3
5,439,881 8/1995 Narva et al. ............................ 514/2
5,667,993 9/1997 Feitelson et al. .................. 435/91.2
5,670,365 9/1997 Feitelson .......................... 435/252.3
5,770,696 6/1998 Warren ............................... 530/350
5,840,868 11/1998 Warren et al. ...................... 536/23.1
5,849,870 12/1998 Warren et al. ....................... 530/350
5,866,326 2/1999 Warren et al. ........................... 435/6
5,872,212 2/1999 Warren et al. ....................... 530/350
5,877,012 3/1999 Estruch et al. .................... 435/252.3
5,888,801 3/1999 Warren et al. .................... 436/252.5
5,889,174 3/1999 Warren et al. .................... 536/23.71

FOREIGN PATENT DOCUMENTS 0359472 3/1990 (EP) .
9404684 3/1994 (WO) .
9405771 3/1994 (WO) .
9421795 9/1994 (WO) .
9424264 10/1994 (WO) .
9605314 2/1996 (WO) .
9610083 4/1996 (WO) .
9818932 5/1998 (WO) .

OTHER PUBLICATIONS

Gaertner, F. H., Leo Kim (1988) "Current Applied Recombinant DNA Projects" TIBTECH 6(4):54–57.

Gaertner, F.H. 1990 "Cellular Delivery Systems for Insecticidal Proteins: Living and Non–Living Microorganisms" in *Controlled Delivery of Crop Protection Agents*, R.M. Wilkins, ed., Taylor and Francis, New York and London, pp. 245–255.

Couch, T.L. (1980) "Mosquito Pthogenicity of *Bacukkys tgyrubguebsus* var. israelensis" in Developments in Industrial Microbiology 22:61–76.

Beegle, C.C. (1978) "Use of Entomogenous Bacteria in Agroccosystems" in Developments in Industrial Microbiology 20:97–104.

Feitelson, J.S., Jewel Payne, Leo Kim (1992) *Bacillus thuringiensis*: Insects and Beyond Bio/Technology 10:271–275.

Lambert, B., et al. (1996) "A *Bacillus thuringiensis* Insecticidal Crystal Protein with a High Activity against Members of the Family Noctuidae" Applied and Environmental MicroBiology 62(1): 80–86.

Gleave, A.P., et al. (1992) Identification of an Insecticidal Crystal Protein from *Bacillus thuringiensis* DSIR517 with Significant Sequence Differences from Previously Described Toxins38 Journal of General Microbiolgy 138:55–62.

Shevelev, A.B., et al. (1993) "Primary Structure of cryX**, the Novel δ–endotoxin–related gene from *Bacillus thuringiensis* spp. galleriae" FEBS 336(1): 79–82.

(List continued on next page.)

*Primary Examiner*—Gabriele E. Bugalsky
(74) *Attorney, Agent, or Firm*—Saliwanchik, Lloyd & Saliwanchik

(57) ABSTRACT

Disclosed and claimed are novel *Bacillus thuringiensis* isolates, pesticidal toxins, genes, and nucleotide probes and primers for the identification of genes encoding toxins active against pests. The primers are useful in PCR techniques to produce gene fragments which are characteristic of genes encoding these toxins. The subject invention provides entirely new families of toxins from Bacillus isolates.

48 Claims, No Drawings

OTHER PUBLICATIONS

Smulevitch, S.V., et al. (1991) "Nucleotide Sequence of a Novel δ–Endotoxin Gene cryig of *Bacillus thuringiensis* ssp. galleriae" FEBS 293(1–2):25–28.

Schnepf, H.E., H.R. Whiteley (1981) "Dloning and Expression of the *Bacillus thuringiensis* Crystal Protein Gene in *Escheria coli*" Proc. Natl. Acad. Sci. USA 78(5): 2893–2897.

Estruch, J.J., et al. (1996) "Vip3A, A Novel *Bacillus thuringiensis* Vegetative Insecticidal Protein with a Wide Spectrum of Activities Against Lepidopteran Insects" Proc. Natl. Acad. Sci. USA 93:5389–5394.

Carozzi, N.B., et al. (1991) "Prediction of Insecticidal Activity of *Bacillus thuringiensis* Strains by Polymerase Chain Reaction Product Profiles" Applied and Environmental Microbiology 57(11):3057–3061.

Asano, Shoji, Hidetaka Hori, Yunlong Cui (1994) "A Unique Activity in *Bacillus thuringiensis* Growth Medium" Appl. Entomol. Zool. 29(1):39–45.

Li, Jade (1992) "Bacterial Toxins" Current Opinion in Structural Biology 2:545–556.

PESTICIDAL TOXINS AND NUCLEOTIDE SEQUENCES WHICH ENCODE THESE TOXINS

CROSS-REFERENCE TO RELATED APPLICATIONS

This application is a continuation-in-part of co-pending application Ser. No. 08/960,780, filed Oct. 30, 1997; which claims priority from provisional application Ser. No. 60/029, 848, filed Oct. 30, 1996.

BACKGROUND OF THE INVENTION

The soil microbe *Bacillus thuringiensis* (B.t.) is a Gram-positive, spore-forming bacterium characterized by parasporal crystalline protein inclusions. These inclusions often appear microscopicallyas distinctively shaped crystals. The proteins can be highly toxic to pests and specific in their toxic activity. Certain B.t. toxin genes have been isolated and sequenced, and recombinant DNA-based B.t. products have been produced and approved for use. In addition, with the use of genetic engineering techniques, new approaches for delivering these B.t. endotoxins to agricultural environments are under development, including the use of plants genetically engineered with endotoxin genes for insect resistance and the use of stabilized intact microbial cells as B.t. endotoxin delivery vehicles (Gaertner, F. H., L. Kim [1988] *TIBTECH* 6:S4–S7). Thus, isolated B.t. endotoxin genes are becoming commercially valuable.

Until the last fifteen years, commercial use of B.t. pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystalline δ-endotoxin which is toxic to the larvae of a number of lepidopteran insects.

In recent years, however, investigators have discovered B.t. pesticides with specificities for a much broader range of pests. For example, other species of B.t., namely *israelensis* and *morrisoni* (a.k.a. *tenebrionis*, a.k.a. B.t. M-7, a.k.a. B.t. *san diego*), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255.). See also Couch, T. L. (1980) "Mosquito Pathogenicity of *Bacillus thuringiensis* var. *israelensis*," *Developments in Industrial Microbiology* 22:61–76; and Beegle, C. C. (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang Ent.* 96:500–508 describe *Bacillus thuringiensis* var. *tenebrionis*, which is reportedly active against two beetles in the order Coleoptera. These are the Colorado potato beetle, *Leptinotarsa decemlineata*, and *Agelastica alni*.

More recently, new subspecies of B.t. have been identified, and genes responsible for active δ-endotoxin proteins have been isolated (Höfte, H., H. R. Whiteley [1989] *Microbiological Reviews* 52(2):242–255). Höfte and Whiteley classified B.t. crystal protein genes into four major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported (Feitelson, J. S., J. Payne, L. Kim [1992] *Bio/Technology* 10:271–275). CryV has been proposed to designate a class of toxin genes that are nematode-specific. Lambert et al. (Lambert, B., L. Buysse, C. Decock, S. Jansens, C. Piens, B. Saey, J. Seurinck, K. van Audenhove, J. Van Rie, A. Van Vliet, M. Peferoen [1996] *Appl. Environ. Microbiol* 62(1):80–86) describe the characterization of a Cry9 toxin active against lepidopterans. Published PCT applications WO 94/05771 and WO 94/24264 also describe B.t. isolates active against lepidopteran pests. Gleave et al. ([1991] JGM 138:55–62), Shevelev et al. ([1993] *FEBS Lett.* 336:79–82; and Smulevitch et al. ([1991] *FEBS Lett.* 293:25–26) also describe B.t. toxins. Many other classes of B.t. genes have now been identified.

The cloning and expression of a B.t. crystal protein gene in *Escherichia coli* has been described in the published literature (Schnepf, H. E., H. R. Whiteley [1981] *Proc. Natl. Acad. Sci. USA* 78:2893–2897.). U.S. Pat. Nos. 4,448,885 and 4,467,036 both disclose the expression of B.t. crystal protein in *E. coli.* U.S. Pat. Nos. 4,990,332; 5,039,523; 5,126,133; 5,164,180; and 5,169,629 are among those which disclose B.t. toxins having activity against lepidopterans. PCT application WO96/05314 discloses PS86W1, PS86V1, and other B.t. isolates active against lepidopteran pests. The PCT patent applications published as WO94/24264 and WO94/05771 describe B.t. isolates and toxins active against lepidopteran pests. B.t. proteins with activity against members of the family Noctuidae are described by Lambert et al., supra. U.S. Pat. Nos. 4,797,276 and 4,853,331 disclose *B. thuringiensis* strain *tenebrionis* which can be used to control coleopteran pests in various environments. U.S. Pat. No. 4,918,006 discloses B.t. toxins having activity against dipterans. U.S. Pat. Nos. 5,151,363 and 4,948,734 disclose certain isolates of B.t. which have activity against nematodes. Other U.S. patents which disclose activity against nematodes include U.S. Pat. Nos. 5,093,120; 5,236,843; 5,262,399; 5,270,448; 5,281,530; 5,322,932; 5,350,577; 5,426,049; 5,439,881, 5,667,993; and 5,670,365. As a result of extensive research and investment of resources, other patents have issued for new B.t. isolates and new uses of B.t. isolates. See Feitelson et al., supra, for a review. However, the discovery of new B.t. isolates and new uses of known B.t. isolates remains an empirical, unpredictable art.

Isolating responsible toxin genes has been a slow empirical process. Carozzi et al. (Carozzi, N. B., V. C. Kramer, G. W. Warren, S. Evola, G. Koziel (1991) *Appl. Env. Microbiol.* 57(11):3057–3061) describe methods for identifyingtoxin genes. U.S. Pat. No. 5,204,237 describes specific and universal probes for the isolation of B.t. toxin genes. That patent, however, does not describe the probes and primers of the subject invention.

WO 94/21795, WO 96/10083, and Estruch, J. J. et al. (1996) *PNAS* 93:5389–5394 describe toxins obtained from Bacillus microbes. These toxins are reported to be produced during vegetative cell growth and were thus termed vegetative insecticidal proteins (VIP). These toxins were reported to be distinct from crystal-forming δ-endotoxins. Activity of these toxins against lepidopteran and coleopteran pests was reported. These applications make specific reference to toxins designated Vip1A(a), Vip1A(b), Vip2A(a), Vip2A(b), Vip3A(a), and Vip3A(b). The toxins and genes of the current invention are distinct from those disclosed in the '795 and '083 applications and the Estruch article.

BRIEF SUMMARY OF THE INVENTION

The subject invention concerns materials and methods useful in the control of non-mammalian pests and, particularly, plant pests. In one embodiment, the subject invention provides novel B.t. isolates having advantageous activity against non-mammalian pests. In a further embodiment, the subject invention provides new toxins useful for the control of non-mammalian pests. In a preferred embodiment, these pests are lepidopterans and/or coleopterans. The toxins of the subject invention include δ-endotoxins as well as soluble toxins which can be obtained from the supernatant of Bacillus cultures.

The subject invention further provides nucleotide sequences which encode the toxins of the subject invention. The subject invention further provides nucleotide sequences and methods useful in the identification and characterization of genes which encode pesticidal toxins.

In one embodiment, the subject invention concerns unique nucleotide sequences which are useful as hybridization probes and/or primers in PCR techniques. The primers produce characteristic gene fragments which can be used in the identification, characterization, and/or isolation of specific toxin genes. The nucleotide sequences of the subject invention encode toxins which are distinct from previously-described toxins.

In a specific embodiment,the subject invention provides new classes of toxins having advantageous pesticidal activities. These classes of toxins can be encoded by polynucleotide sequences which are characterized by their ability to hybridize with certain exemplified sequences and/or by their ability to be amplified by PCR using certain exemplified primers.

One aspect of the subject invention pertains to the identification and characterization of entirely new families of *Bacillus thuringiensis* toxins having advantageous pesticidal properties. Specific new toxin families of the subject invention include MIS-1, MIS-2, MIS-3, MIS-4, MIS-5, MIS-6, MIS-7, MIS-8, WAR-1, and SUP-1. These families of toxins, and the genes which encode them, can be characterized in terms of, for example, the size of the toxin or gene, the DNA or amino acid sequence, pesticidal activity, and/or antibody reactivity. With regard to the genes encoding the novel toxin families of the subject invention, the current disclosure provides unique hybridization probes and PCR primers which can be used to identify and characterize DNA within each of the exemplified families.

In one embodiment of the subject invention, Bacillus isolates can be cultivated under conditions resulting in high multiplication of the microbe. After treating the microbe to provide single-stranded genomic nucleic acid, the DNA can be contacted with the primers of the invention and subjected to PCR amplification. Characteristic fragments of toxin-encoding genes will be amplified by the procedure, thus identifying the presence of the toxin-encoding gene(s).

A further aspect of the subject invention is the use of the disclosed nucleotide sequences as probes to detect genes encoding Bacillus toxins which are active against pests.

Further aspects of the subject invention include the genes and isolates identified using the methods and nucleotide sequences disclosed herein. The genes thus identified encode toxins active against pests. Similarly, the isolates will have activity against these pests. In a preferred embodiment, these pests are lepidopteran or coleopteran pests.

In a preferred embodiment, the subject invention concerns plants cells transformed with at least one polynucleotide sequence of the subject invention such that the transformed plant cells express pesticidal toxins in tissues consumed by target pests. As described herein, the toxins useful according to the subject invention may be chimeric toxins produced by combining portions of multiple toxins. In addition, mixtures and/or combinations of toxins can be used according to the subject invention.

Transformation of plants with the genetic constructs disclosed herein can be accomplished using techniques well known to those skilled in the art and would typically involve modification of the gene to optimize expression of the toxin in plants.

Alternatively, the Bacillus isolates of the subject invention, or recombinant microbes expressing the toxins described herein, can be used to control pests. In this regard, the invention includes the treatment of substantially intact Bacillus cells, and/or recombinant cells containing the expressed toxins of the invention, treated to prolong the pesticidal activity when the substantially intact cells are applied to the environment of a target pest. The treated cell acts as a protective coating for the pesticidal toxin. The toxin becomes active upon ingestion by a target insect.

BRIEF DESCRIPTION OF THE SEQUENCES

SEQ ID NO. 1 is a forward primer, designated "the 339 forward primer," used according to the subject invention.

SEQ ID NO. 2 is a reverse primer, designated "the 339 reverse primer," used according to the subject invention.

SEQ ID NO. 3 is a nucleotide sequence encoding a toxin from B.t. strain PS36A.

SEQ ID NO. 4 is an amino acid sequence for the 36A toxin.

SEQ ID NO. 5 is a nucleotide sequence encoding a toxin from B.t. strain PS81F.

SEQ ID NO. 6 is an amino acid sequence for the 81F toxin.

SEQ ID NO. 7 is a nucleotide sequence encoding a toxin from B.t. strain Javelin 1990.

SEQ ID NO. 8 is an amino acid sequence for the Javelin 1990 toxin.

SEQ ID NO. 9 is a forward primer, designated "158C2 PRIMERA," used according to the subject invention.

SEQ ID NO. 10 is a nucleotide sequence encoding a portion of a soluble toxin from B.t. PS158C2.

SEQ ID NO. 11 is a forward primer, designated "49C PRIMER A," used according to the subject invention.

SEQ ID NO. 12 is a nucelotide sequence of a portion of a toxin gene from B.t. strain PS49C.

SEQ ID NO. 13 is a forward primer, designated "49C PRIMER B," used according to the subject invention.

SEQ ID NO. 14 is a reverse primer, designated "49C PRIMER C," used according to the subject invention.

SEQ ID NO. 15 is an additional nucleotide sequence of a portion of a toxin gene from PS49C.

SEQ ID NO. 16 is a forward primer used according to the subject invention.

SEQ ID NO. 17 is a reverse primer used according to the subject invention.

SEQ ID NO. 18 is a nucleotide sequence of a toxin gene from B.t. strain PS10E 1.

SEQ ID NO. 19 is an amino acid sequence from the 10E1 toxin.

SEQ ID NO. 20 is a nucleotide sequence of a toxin gene from B.t. strain PS31J2.

SEQ ID NO. 21 is an amino acid sequence from the 31J2 toxin.

SEQ ID NO. 22 is a nucleotide sequence of a toxin gene from B.t. strain PS33D2.

SEQ ID NO. 23 is an amino acid sequence from the 33D2 toxin.

SEQ ID NO. 24 is a nucleotide sequence of a toxin gene from B.t. strain PS66D3

SEQ ID NO. 25 is an amino acid sequence from the 66D3 toxin.

SEQ ID NO. 26 is a nucleotide sequence of a toxin gene from B.t. strain PS68F.

SEQ ID NO. 27 is an amino acid sequence from the 68F toxin.

SEQ ID NO. 28 is a nucleotide sequence of a toxin gene from B.t. strain PS69AA2

SEQ ID NO. 29 is an amino acid sequence from the 69AA2 toxin.

SEQ ID NO. 30 is a nucleotide sequence of a toxin gene from B.t. strain PS 168G1.

SEQ ID NO. 31 is a nucleotide sequence of a MIS toxin gene from B.t. strain PS177C8.

SEQ ID NO. 32 is an amino acid sequence from the 177C8-MIS toxin.

SEQ ID NO. 33 is a nucleotide sequence of a toxin gene from B.t. strain PS177I8

SEQ ID NO. 34 is an amino acid sequence from the 177I8 toxin.

SEQ ID NO. 35 is a nucleotide sequence of a toxin gene from B.t. strain PS185AA2.

SEQ ID NO. 36 is an amino acid sequence from the 185AA2 toxin.

SEQ ID NO. 37 is a nucleotide sequence of a toxin gene from B.t. strain PS196F3.

SEQ ID NO. 38 is an amino acid sequence from the 196F3 toxin.

SEQ ID NO. 39 is a nucleotide sequence of a toxin gene from B.t. strain PS196J4.

SEQ ID NO. 40 is an amino acid sequence from the 196J4 toxin.

SEQ ID NO. 41 is a nucleotide sequence of a toxin gene from B.t. strain PS197T1.

SEQ ID NO. 42 is an amino acid sequence from the 197T1 toxin.

SEQ ID NO. 43 is a nucleotide sequence of a toxin gene from B.t. strain PS197U2.

SEQ ID NO. 44 is an amino acid sequence from the 197U2 toxin.

SEQ ID NO. 45 is a nucleotide sequence of a toxin gene from B.t. strain PS202E1.

SEQ ID NO. 46 is an amino acid sequence from the 202E1 toxin.

SEQ ID NO. 47 is a nucleotide sequence of a toxin gene from B.t. strain KB33.

SEQ ID NO. 48 is a nucleotide sequence of a toxin gene from B.t. strain KB38.

SEQ ID NO. 49 is a forward primer, designated "ICON-forward," used according to the subject invention.

SEQ ID NO. 50 is a reverse primer, designated "ICON-reverse," used according to the subject invention.

SEQ ID NO. 51 is a nucleotide sequence encoding a 177C8-WAR toxin gene from B.t. strain PS177C8.

SEQ ID NO. 52 is an amino acid sequence of a 177C8-WAR toxin from B.t. strain PS177C8.

SEQ ID NO. 53 is a forward primer, designated "SUP-1A," used according to the subject invention.

SEQ ID NO. 54 is a reverse primer, designated "SUP-1B," used according to the subject invention.

SEQ ID NOS. 55–110 are primers used according to the subject invention.

SEQ ID NO. 111 is the reverse complement of the primer of SEQ ID NO. 58.

SEQ ID NO. 112 is the reverse complement of the primer of SEQ ID NO. 60.

SEQ ID NO. 113 is the reverse complement of the primer of SEQ ID NO. 64.

SEQ ID NO. 114 is the reverse complement of the primer of SEQ ID NO. 66.

SEQ ID NO. 115 is the reverse complement of the primer of SEQ ID NO. 68.

SEQ ID NO. 116 is the reverse complement of the primer of SEQ ID NO. 70.

SEQ ID NO. 117 is the reverse complement of the primer of SEQ ID NO. 72.

SEQ ID NO. 118 is the reverse complement of the primer of SEQ ID NO. 76.

SEQ ID NO. 119 is the reverse complement of the primer of SEQ ID NO. 78.

SEQ ID NO. 120 is the reverse complement of the primer of SEQ ID NO. 80.

SEQ ID NO. 121 is the reverse complement of the primer of SEQ ID NO. 82.

SEQ ID NO. 122 is the reverse complement of the primer of SEQ ID NO. 84.

SEQ ID NO. 123 is the reverse complement of the primer of SEQ ID NO. 86.

SEQ ID NO. 124 is the reverse complement of the primer of SEQ ID NO. 88.

SEQ ID NO. 125 is the reverse complement of the primer of SEQ ID NO. 92.

SEQ ID NO. 126 is the reverse complement of the primer of SEQ ID NO. 94.

SEQ ID NO. 127 is the reverse complement of the primer of SEQ ID NO. 96.

SEQ ID NO. 128 is the reverse complement of the primer of SEQ ID NO. 98.

SEQ ID NO. 129 is the reverse complement of the primer of SEQ ID NO. 99.

SEQ ID NO. 130 is the reverse complement of the primer of SEQ ID NO. 100.

SEQ ID NO. 131 is the reverse complement of the primer of SEQ ID NO. 104.

SEQ ID NO. 132 is the reverse complement of the primer of SEQ ID NO. 106.

SEQ ID NO. 133 is the reverse complement of the primer of SEQ ID NO. 108.

SEQ ID NO. 134 is the reverse complement of the primer of SEQ ID NO. 110.

SEQ ID NO. 135 is a MIS-7 forward primer.

SEQ ID NO. 136 is a MIS-7 reverse primer.

SEQ ID NO. 137 is a MIS-8 forward primer.

SEQ ID NO. 138 is a MIS-8 reverse primer.

SEQ ID NO. 139 is a nucleotide sequence of a MIS-7 toxin gene designated 157C1-A from B.t. strain PS157C1.

SEQ ID NO. 140 is an amino acid sequence of a MIS-7 toxin designated 157C1-A from B.t. strain PS157C1.

SEQ ID NO. 141 is a nucleotide sequence of a MIS-7 toxin gene from B.t. strain PS201Z.

SEQ ID NO. 142 is a nucleotide sequence of a MIS-8 toxin gene from B.t. strain PS31F2.

SEQ ID NO. 143 is a nucleotide sequence of a MIS-8 toxin gene from B.t. strain PS185Y2.

SEQ ID NO. 144 is a nucleotide sequence of a MIS-1 toxin gene from B.t. strain PS33F1.

DETAILED DISCLOSURE OF THE INVENTION

The subject invention concerns materials and methods for the control of non-mammalian pests. In specific embodiments, the subject invention pertains to new *Bacillus thuringiensis* isolates and toxins which have activity against lepidopterans and/or coleopterans. The subject invention further concerns novel genes which encode pesticidal toxins and novel methods for identifying and characterizing Bacillus genes which encode toxins with useful properties. The subject invention concerns not only the polynucleotide sequences which encode these toxins, but also the use of these polynucleotide sequences to produce recombinant hosts which express the toxins. The proteins of the subject invention are distinct from protein toxins which have previously been isolated from *Bacillus thuringiensis.*

B.t. isolates useful according to the subject invention have been deposited in the permanent collection of the Agricultural Research Service Patent Culture Collection (NRRL), Northern Regional Research Center, 1815 North University Street, Peoria, Ill. 61604, USA. The culture repository numbers of the B.t. strains are as follows:

TABLE 1

| Culture | Repository No. | Deposit Date | Patent No. |
|---|---|---|---|
| B.t. PS11B (MT274) | NRRL B-21556 | April 18, 1996 | |
| B.t. PS24J | NRRL B-18881 | August 30, 1991 | |
| B.t. PS31G1 (MT278) | NRRL B-21560 | April 18, 1996 | |
| B.t. PS36A | NRRL B-18929 | December 27, 1991 | |
| B.t. PS33F2 | NRRL B-18244 | July 28, 1987 | 4,861,595 |
| B.t. PS40D1 | NRRL B-18300 | February 3, 1988 | 5,098,705 |
| B.t. PS43F | NRRL B-18298 | February 2, 1988 | 4,996,155 |
| B.t. PS45B1 | NRRL B-18396 | August 16, 1988 | 5,427,786 |
| B.t. PS49C | NRRL B-21532 | March 14, 1996 | |
| B.t. PS52A1 | NRRL B-18245 | July 28, 1987 | 4,861,595 |
| B.t. PS62B1 | NRRL B-18398 | August 16, 1988 | 4,849,217 |
| B.t. PS81A2 | NRRL B-18484 | April l9,1989 | 5,164,180 |
| B.t. PS81F | NRRL B-18424 | October 7, 1988 | 5,045,469 |
| B.t. PS81GG | NRRL B-18425 | October 11, 1988 | 5,169,629 |
| B.t. PS81I | NRRL B-18484 | April 19, 1989 | 5,126,133 |
| B.t. PS85A1 | NRRL B-18426 | October 11, 1988 | |
| B.t. PS86A1 | NRRL B-18400 | August 16, 1988 | 4,849,217 |
| B.t. PS86B1 | NRRL B-18299 | February 2, 1988 | 4,966,765 |
| B.t. PS86BB1 (MT275) | NRRL B-21557 | April 18, 1996 | |
| B.t. PS86Q3 | NRRL B-18765 | February 6, 1991 | 5,208,017 |
| B.t. PS86V1 (MT276) | NRRL B-21558 | April 18, 1996 | |
| B.t. PS86W1 (MT277) | NRRL B-21559 | April 18, 1996 | |
| B.t. PS89J3 (MT279) | NRRL B-21561 | April 18, 1996 | |
| B.t. PS91C2 | NRRL B-18931 | February 6, 1991 | |
| B.t. PS92B | NRRL B-18889 | September 23, 1991 | 5,427,786 |
| B.t. PS101Z2 | NRRL B-18890 | October 1, 1991 | 5,427,786 |
| B.t. PS122D3 | NRRL B-18376 | June 9, 1988 | 5,006,336 |
| B.t. PS123D1 | NRRL B-21011 | October 13, 1992 | 5,508,032 |
| B.t. PS157C1 (MT104) | NRRL B-18240 | July 17, 1987 | 5,262,159 |
| B.t. PS158C2 | NRRL B-18872 | August 27, 1991 | 5,268,172 |
| B.t. PS169E | NRRL B-18682 | July 17,1990 | 5,151,363 |
| B.t. PS177F1 | NRRL B-18683 | July 17,1990 | 5,151,363 |
| B.t. PS177G | NRRL B-18684 | July 17,1990 | 5,151,363 |
| B.t. PS185L2 | NRRL B-21535 | March 14, 1996 | |
| B.t. PS185U2 (MT280) | NRRL B-21562 | April 18, 1996 | |
| B.t. PS192M4 | NRRL B-18932 | December 27, 1991 | 5,273,746 |
| B.t. PS201L1 | NRRL B-18749 | January 9, 1991 | 5,298,245 |
| B.t. PS204C3 | NRRL B-21008 | October 6, 1992 | |
| B.t. PS204G4 | NRRL B-18685 | July 17, 1990 | 5,262,399 |
| B.t. PS242H10 | NRRL B-21439 | March 14, 1996 | |
| B.t. PS242K17 | NRRL B-21540 | March 14, 1996 | |
| B.t. PS244A2 | NRRL B-21541 | March 14, 1996 | |
| B.t. PS244D1 | NRRL B-21542 | March 14, 1996 | |
| B.t. PS10E1 | NRRL B-21862 | October 24, 1997 | |
| B.t. PS31F2 | NRRL B-21876 | October 24, 1997 | |
| B.t. PS31J2 | NRRL B-21009 | October 13, 1992 | |
| B.t. PS33D2 | NRRL B-21870 | October 24, 1997 | |
| B.t. PS66D3 | NRRL B-21858 | October 24, 1997 | |
| B.t. PS68F | NRRL B-21857 | October 24, 1997 | |
| B.t. PS69AA2 | NRRL B-21859 | October 24, 1997 | |
| B.t. PS146D | NRRL B-21866 | October 24, 1997 | |
| B.t. PS168G1 | NRRL B-21873 | October 24, 1997 | |
| B.t. PS175I4 | NRRL B-21865 | October 24, 1997 | |
| B.t. PS177C8a | NRRL B-21867 | October 24, 1997 | |
| B.t. PS177I8 | NRRL B-21868 | October 24, 1997 | |
| B.t. PS185AA2 | NRRL B-21861 | October 24, 1997 | |

TABLE 1-continued

| Culture | Repository No. | Deposit Date | Patent No. |
|---|---|---|---|
| B.t. PS196J4 | NRRL B-21860 | October 24, 1997 | |
| B.t. PS196F3 | NRRL B-21872 | October 24, 1997 | |
| B.t. PS197T1 | NRRL B-21869 | October 24, 1997 | |
| B.t. PS197U2 | NRRL B-21871 | October 24, 1997 | |
| B.t. PS202E1 | NRRL B-21874 | October 24, 1997 | |
| B.t. PS217U2 | NRRL B-21864 | October 24, 1997 | |
| KB33 | NRRL B-21875 | October 24, 1997 | |
| KB38 | NRRL B-21863 | October 24, 1997 | |
| KB53A49-4 | NRRL B-21879 | October 24, 1997 | |
| KB68B46-2 | NRRL B-21877 | October 24, 1997 | |
| KB68B51-2 | NRRL B-21880 | October 24, 1997 | |
| KB68B55-2 | NRRL B-21878 | October 24, 1997 | |
| PS80JJ1 | NRRL B-18679 | July 17, 1990 | 5,151,363 |
| PS94R1 | NRRL B-21801 | July 1, 1997 | |
| PS101DD | NRRL B-21802 | July 1, 1997 | |
| PS202S | NRRL B-21803 | July 1, 1997 | |
| PS213E5 | NRRL B-21804 | July 1, 1997 | |
| PS218G2 | NRRL B-21805 | July 1, 1997 | |
| PS33F1 | NRRL B-21977 | April 24, 1998 | |
| PS71G4 | NRRL B-21978 | April 24, 1998 | |
| PS86D1 | NRRL B-21979 | April 24, 1998 | |
| PS185V2 | NRRL B-21980 | April 24,1998 | |
| PS191A21 | NRRL B-21981 | April 24,1998 | |
| PS201Z | NRRL B-21982 | April 24, 1998 | |
| PS205A3 | NRRL B-21983 | April 24, 1998 | |
| PS205C | NRRL B-21984 | April 24,1998 | |
| PS234E1 | NRRL B-21985 | April 24, 1998 | |
| PS248N10 | NRRL B-21986 | April 24, 1998 | |
| KB63B19-13 | NRRL B-21990 | April 29, 1998 | |
| KB63B19-7 | NRRL B-21989 | April 29, 1998 | |
| KB68B62-7 | NRRL B-21991 | April 29, 1998 | |
| KB68B63-2 | NRRL B-21992 | April 29, 1998 | |
| KB69A125-1 | NRRL B-21993 | April 29, 1998 | |
| KB69A125-3 | NRRL B-21994 | April 29, 1998 | |
| KB69A125-5 | NRRL B-21995 | April 29, 1998 | |
| KB69A127-7 | NRRL B-21996 | April 29, 1998 | |
| KB69A132-1 | NRRL B-21997 | April 29, 1998 | |
| KB69B2-1 | NRRL B-21998 | April 29, 1998 | |
| KB70B5-3 | NRRL B-21999 | April 29, 1998 | |
| KB71A125-15 | NRRL B-30001 | April 29, 1998 | |
| KB71A35-6 | NRRL B-30000 | April 29, 1998 | |
| KB71A72-1 | NRRL B-21987 | April 29, 1998 | |
| KB71A134-2 | NRRL B-21988 | April 29, 1998 | |

Cultures which have been deposited for the purposes of this patent application were deposited under conditions that assure that access to the cultures is available during the pendency of this patent application to one determined by the Commissioner of Patents and Trademarks to be entitled thereto under 37 CFR 1.14 and 35 U.S.C. 122. The deposits will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the culture(s). The depositor acknowledges the duty to replace the deposit(s) should the depository be unable to furnish a sample when requested, due to the condition of a deposit. All restrictions on the availability to the public of the subject culture deposits will be irrevocably removed upon the granting of a patent disclosing them.

Many of the strains useful according to the subject invention are readily available by virtue of the issuance of patents disclosing these strains or by their deposit in public collections or by their inclusion in commercial products. For example, the B.t. strain used in the commercial product, Javelin, and the HD isolates are all publicly available.

Mutants of the isolates referred to herein can be made by procedures well known in the art. For example, an asporogenous mutant can be obtained through ethylmethane sulfonate (EMS) mutagenesis of an isolate. The mutants can be made using ultraviolet light and nitrosoguanidine by procedures well known in the art.

In one embodiment, the subject invention concerns materials and methods including nucleotide primers and probes for isolating, characterizing, and identifying Bacillus genes encoding protein toxins which are active against non-mammalian pests. The nucleotide sequences described herein can also be used to identify new pesticidal Bacillus isolates. The invention further concerns the genes, isolates, and toxins identified using the methods and materials disclosed herein.

The new toxins and polynucleotide sequences provided here are defined according to several parameters. One characteristic of the toxins described herein is pesticidal activity. In a specific embodiment, these toxins have activity against coleopteran and/or lepidopteran pests. The toxins and genes of the subject invention can be further defined by their amino acid and nucleotide sequences. The sequences of the molecules can be defined in terms of homology to certain exemplified sequences as well as in terms of the ability to hybridize with, or be amplified by, certain exemplified probes and primers. The toxins provided herein can also be identified based on their immunoreactivity with certain antibodies.

An important aspect of the subject invention is the identification and characterization of new families of Bacillus toxins, and genes which encode these toxins. These families have been designated MIS-1, MIS-2, MIS-3, MIS-4, MIS-5, MIS-6, MIS-7, MIS-8, WAR-1, and SUP-1. Toxins within these families, as well as genes encoding toxins within these families, can readily be identified as described herein by, for example, size, amino acid or DNA sequence, and antibody reactivity. Amino acid and DNA sequence characteristics include homology with exemplified sequences, ability to hybridize with DNA probes, and ability to be amplified with specific primers.

The MIS-1 family of toxins includes toxins from isolates PS68F and PS33F1. Also provided are hybridization probes and PCR primers which specifically identify genes falling in the MIS-1 family.

A second family of toxins identified herein is the MIS-2 family. This family includes toxins which can be obtained from isolates PS66D3, PS197T1, and PS31J2. The subject invention further provides probes and primers for the identification of MIS-2 toxins and genes.

A third family of toxins identified herein is the MIS-3 family. This family includes toxins which can be obtained from B.t. isolates PS69AA2 and PS33D2. The subject invention further provides probes and primers for identification of the MIS-3 genes and toxins.

Polynucleotide sequences encoding MIS-4 toxins can be obtained from the B.t. isolate designated PS197U2. The subject invention further provides probes and primers for the identification of genes and toxins in this family.

A fifth family of toxins identified herein is the MIS-5 family. This family includes toxins which can be obtained from B.t. isolates KB33 and KB38. The subject invention further provides probes and primers for identification of the MIS-5 genes and toxins.

A sixth family of toxins identified herein is the MIS-6 family. This family includes toxins which can be obtained from B.t. isolates PS196F3, PS168G1, PS196J4, PS202E1, PS10E1, and PS185AA2. The subject invention further provides probes and primers for identification of the MIS-6 genes and toxins.

A seventh family of toxins identified herein is the MIS-7 family. This family includes toxins which can be obtained from B.t. isolates PS157C1, PS205C, and PS201Z. The subject invention further provides probes and primers for identification of the MIS-7 genes and toxins.

An eighth family of toxins identified herein is the MIS-8 family. This family includes toxins which can be obtained from B.t. isolates PS31F2 and PS185Y2. The subject invention further provides probes and primers for identification of the MIS-8 genes and toxins.

In a preferred embodiment, the genes of the MIS family encode toxins having a molecular weight of about 70 to about 100 kDa and, most preferably, the toxins have a size of about 80 kDa. Typically, these toxins are soluble and can be obtained from the supernatant of Bacillus cultures as described herein. These toxins have toxicity against non-mammalian pests. In a preferred embodiment, these toxins have activity against coleopteran pests. The MIS proteins are further useful due to their ability to form pores in cells. These proteins can be used with second entities including, for example, other proteins. When used with a second entity, the MIS protein will facilitate entry of the second agent into a target cell. In a preferred embodiment, the MIS protein interacts with MIS receptors in a target cell and causes pore formation in the target cell. The second entity may be a toxin or another molecule whose entry into the cell is desired.

The subject invention further concerns a family of toxins designated WAR-1. The WAR-1 toxins typically have a size of about 30–50 kDa and, most typically, have a size of about 40 kDa. Typically, these toxins are soluble and can be obtained from the supernatant of Bacillus cultures as described herein. The WAR-1 toxins can be identified with primers described herein as well as with antibodies. In a specific embodiment, the antibodies can be raised to, for example, toxin from isolate PS177C8.

An additional family of toxins provided according to the subject invention are the toxins designated SUP-1. Typically, these toxins are soluble and can be obtained from the supernatant of Bacillus culturesas described herein. In a preferred embodiment, the SUP-1 toxins are active against lepidopteran pests. The SUP-1 toxins typically have a size of about 70–100 kDa and, preferably, about 80 kDa. The SUP-1 family is exemplified herein by toxins from isolates PS49C and PS158C2. The subject invention provides probes and primers useful for the identification of toxins and genes in the SUP-1 family The subject invention further provides specific Bacillus toxins and genes which did not fall into any of the new families disclosed herein. These specific toxins and genes include toxins and genes which can be obtained from PS177C8 and PS 177I8.

Toxins in the MIS, WAR, and SUP families are all soluble and can be obtained as described herein from the supernatant of Bacillus cultures. These toxins can be used alone or in combination with other toxins to control pests. For example, toxins from the MIS families may be used in conjunction with WAR-type toxins to achieve control of pests, particularly coleopteran pests. These toxins may be used, for example, with δ-endotoxins which are obtained from Bacillus isolates.

Table 2 provides a summary of the novel families of toxins and genes of the subject invention. Each of the eight MIS families is specifically exemplified herein by toxins which can be obtained from particular B.t. isolates as shown in Table 2. Genes encoding toxins in each of these families can be identified by a variety of highly specific parameters, including the ability to hybridize with the particular probes set forth in Table 2. Sequence identity in excess of about 80% with the probes set forth in Table 2 can also be used to identify the genes of the various families. Also exemplified are particular primer pairs which can be used to amplify the genes of the subject invention. A portion of a gene within the indicated families would typically be amplifiable with at least one of the enumerated primer pairs. In a preferred embodiment, the amplified portion would be of approximately the indicated fragment size. Primers shown in Table 2 consist of polynucleotide sequences which encode peptides as shown in the sequence listing attached hereto. Additional primers and probes can readily be constructed by those skilled in the art such that alternate polynucleotide sequences encoding the same amino acid sequences can be used to identify and/or characterize additional genes encoding pesticidal toxins. In a preferred embodiment, these additional toxins, and their genes, could be obtained from Bacillus isolates.

TABLE 2

| Family | Isolates | Probes (SEQ ID NO.) | Primer Pairs (SEQ ID NOS.) | Fragment size (nt) |
|---|---|---|---|---|
| MIS-1 | PS68F, PS33F1 | 26, 144 | 56 and 111 | 69 |
| | | | 56 and 112 | 506 |
| | | | 58 and 112 | 458 |
| MIS-2 | PS66D3, PS197T1, PS31J2 | 24, 41, 20 | 62 and 113 | 160 |
| | | | 62 and 114 | 239 |
| | | | 62 and 115 | 400 |
| | | | 62 and 116 | 509 |
| | | | 62 and 117 | 703 |
| | | | 64 and 114 | 102 |
| | | | 64 and 115 | 263 |
| | | | 64 and 116 | 372 |
| | | | 64 and 117 | 566 |
| | | | 66 and 115 | 191 |
| | | | 66 and 116 | 300 |
| | | | 66 and 117 | 494 |
| | | | 68 and 116 | 131 |
| | | | 68 and 117 | 325 |
| | | | 70 and 117 | 213 |
| MIS-3 | PS69AA2, PS33D2 | 28, 22 | 74 and 118 | 141 |
| | | | 74 and 119 | 376 |
| | | | 74 and 120 | 389 |
| | | | 74 and 121 | 483 |
| | | | 74 and 122 | 715 |
| | | | 74 and 123 | 743 |
| | | | 74 and 124 | 902 |
| | | | 76 and 119 | 253 |
| | | | 76 and 120 | 266 |
| | | | 76 and 121 | 360 |
| | | | 76 and 122 | 592 |
| | | | 76 and 123 | 620 |
| | | | 76 and 124 | 779 |
| | | | 78 and 120 | 31 |
| | | | 78 and 121 | 125 |
| | | | 78 and 122 | 357 |
| | | | 78 and 123 | 385 |
| | | | 78 and 124 | 544 |
| | | | 80 and 121 | 116 |
| | | | 80 and 122 | 348 |
| | | | 80 and 123 | 376 |
| | | | 80 and 124 | 535 |
| | | | 82 and 122 | 252 |
| | | | 82 and 123 | 280 |
| | | | 82 and 124 | 439 |
| | | | 84 and 123 | 46 |
| | | | 84 and 124 | 205 |
| | | | 86 and 124 | 177 |
| MIS-4 | PS197U2 | 43 | 90 and 125 | 517 |
| | | | 90 and 126 | 751 |
| | | | 90 and 127 | 821 |
| | | | 92 and 126 | 258 |
| | | | 92 and 127 | 328 |
| | | | 94 and 127 | 92 |
| MIS-5 | KB33, KB38 | 47, 48 | 97 and 128 | 109 |
| | | | 97 and 129 | 379 |
| | | | 97 and 130 | 504 |
| | | | 98 and 129 | 291 |
| | | | 98 and 130 | 416 |
| | | | 99 and 130 | 144 |
| MIS-6 | PS196F3, PS168G1, PS196J4, PS202E1, PS10E1, PS185AA2 | 18, 30, 35, 37, 39, 45 | 102 and 131 | 66 |
| | | | 102 and 132 | 259 |
| | | | 102 and 133 | 245 |
| | | | 102 and 134 | 754 |
| | | | 104 and 132 | 213 |
| | | | 104 and 133 | 199 |
| | | | 104 and 134 | 708 |
| | | | 106 and 133 | 31 |
| | | | 106 and 134 | 518 |
| | | | 108 and 134 | 526 |
| MIS-7 | PS205C, PS157C1 (157C1-A), PS201Z | 139, 141 | 135 and 136 | 598 |
| MIS-8 | PS31F2, PS185Y2 | 142, 143 | 137 and 138 | 585 |
| SUP-1 | PS49C, PS158C2 | 10, 12, 15 | 53 and 54 | 370 |

Furthermore, chimeric toxins may be used according to the subject invention. Methods have been developed for making useful chimeric toxins by combining portions of B.t. proteins. The portions which are combined need not, themselves, be pesticidal so long as the combination of portions creates a chimeric protein which is pesticidal. This can be done using restriction enzymes, as described in, for example, European Patent 0 228 838; Ge, A. Z., N. L. Shivarova, D. H. Dean (1989) *Proc. Natl. Acad. Sci. USA* 86:4037–4041;Ge, A. Z., D. Rivers, R. Milne, D. H. Dean (1991) *J Biol. Chem.* 266:17954–17958;Schnepf, H. E., K. Tomczak, J. P. Ortega, H. R. Whiteley (1990) *J Biol. Chem.* 265:20923–20930; Honee, G., D. Convents, J. Van Rie, S. Jansens, M. Peferoen, B. Visser (1991) *Mol. Microbiol.* 5:2799–2806. Alternatively, recombination using cellular recombination mechanisms can be used to achieve similar results. See, for example, Caramori, T., A. M. Albertini, A. Galizzi (1991) *Gene* 98:37–44; Widner, W. R., H. R. Whiteley (1990) *J Bacteriol.* 172:2826–2832; Bosch, D., B. Schipper, H. van der Kliej, R. A. de Maagd, W. J. Stickema (1994) *Biotechnology* 12:915–918. A number of other methods are known in the art by which such chimeric DNAs can be made. The subject invention is meant to include chimeric proteins that utilize the novel sequences identified in the subject application.

With the teachings provided herein, one skilled in the art could readily produce and use the various toxins and polynucleotide sequences described herein.

Genes and Toxins

The genes and toxins useful according to the subject invention include not only the full length sequences but also fragments of these sequences, variants, mutants, and fusion proteins which retain the characteristic pesticidal activity of the toxins specifically exemplified herein. Chimeric genes and toxins, produced by combining portions from more than one Bacillus toxin or gene, may also be utilized according to the teachings of the subject invention. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the exemplified toxins.

It is apparent to a person skilled in this art that genes encoding active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from Bacillus isolates and/or DNA libraries using the teachings provided herein. There are a number of methods for obtaining the pesticidal toxins of the instant invention. For example, antibodies to the pesticidal toxins disclosed and claimed herein can be used to identify and isolate toxins from a mixture of proteins. Specifically, antibodies may be raised to the portions of the toxins which are most constant and most distinct from other Bacillus toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins are within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

A further method for identifying the toxins and genes of the subject invention is through the use of oligonucleotide probes. These probes are detectable nucleotide sequences. Probes provide a rapid method for identifying toxin-encoding genes of the subject invention. The nucleotide segments which are used as probes according to the invention can be synthesized using a DNA synthesizer and standard procedures.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. This amino acid identity will typically be greater than 60%, preferably be greater than 75%, more preferably greater than 80%, more preferably greater than 90%, and can be greater than 95%. These identities are as determined using standard alignment techniques. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 3 provides a listing of examples of amino acids belonging to each class.

TABLE 3

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The δ-endotoxins of the subject invention can also be characterized in terms of the shape and location of toxin inclusions, which are described above.

As used herein, reference to "isolated" polynucleotides and/or "purified" toxins refers to these molecules when they are not associated with the other molecules with which they would be found in nature. Thus, reference to "isolated and purified" signifies the involvement of the "hand of man" as described herein. Chimeric toxins and genes also involve the "hand of man."

Recombinant Hosts

The toxin-encoding genes of the subject invention can be introduced into a wide variety of microbial or plant hosts. Expression of the toxin gene results, directly or indirectly, in the production and maintenance of the pesticide. With suitable microbial hosts, e.g., Pseudomonas, the microbes can be applied to the situs of the pest, where they will proliferate and be ingested. The result is a control of the pest. Alternatively, the microbe hosting the toxin gene can be killed and treated under conditions that prolong the activity of the toxin and stabilize the cell. The treated cell, which retains the toxic activity, then can be applied to the environment of the target pest.

Where the Bacillus toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A wide variety of ways are available for introducing a Bacillus gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Synthetic genes which are functionally equivalent to the toxins of the subject invention can also be used to transform hosts. Methods for the production of synthetic genes can be found in, for example, U.S. Pat. No. 5,380,831.

Treatment of Cells

As mentioned above, Bacillus or recombinant cells expressing a Bacillus toxin can be treated to prolong the toxin activity and stabilize the cell. The pesticide microcapsule that is formed comprises the Bacillus toxin within a cellular structure that has been stabilized and will protect the toxin when the microcapsule is applied to the environment of the target pest. Suitable host cells may include either prokaryotes or eukaryotes. As hosts, of particular interest will be the prokaryotes and the lower eukaryotes, such as fungi. The cell will usually be intact and be substantially in the proliferative form when treated, rather than in a spore form.

Treatment of the microbial cell, e.g., a microbe containing the Bacillus toxin gene, can be by chemical or physical means, or by a combination of chemical and/or physical means, so long as the technique does not deleteriously affect the properties of the toxin, nor diminish the cellular capability of protecting the toxin. Methods for treatment of microbial cells are disclosed in U.S. Pat. Nos. 4,695,455 and 4,695,462, which are incorporated herein by reference.

Methods and Formulations for Control of Pests

Control of pests using the isolates, toxins, and genes of the subject invention can be accomplished by a variety of methods known to those skilled in the art. These methods include, for example, the application of Bacillus isolates to the pests (or their location), the application of recombinant microbes to the pests (or their locations), and the transformation of plants with genes which encode the pesticidal toxins of the subject invention. Transformations can be made by those skilled in the art using standard techniques. Materials necessary for these transformations are disclosed herein or are otherwise readily available to the skilled artisan.

Formulated bait granules containing an attractant and the toxins of the Bacillus isolates, or recombinant microbes comprising the genes obtainable from the Bacillus isolates disclosed herein, can be applied to the soil. Formulated product can also be applied as a seed-coating or root treatment or total plant treatment at later stages of the crop cycle. Plant and soil treatments of Bacillus cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations that contain cells will generally have from about $10^2$ to about $10^4$ cells/mg. These formulations will be administered at about 50 mg (liquid or dry) to 1 kg or more per hectare.

The formulations can be applied to the environment of the pest, e.g, soil and foliage, by spraying, dusting, sprinkling, or the like.

Polynucleotide Probes

It is well known that DNA possesses a fundamental property called base complementarity. In nature, DNA ordinarily exists in the form of pairs of anti-parallel strands, the bases on each strand projecting from that strand toward the opposite strand. The base adenine (A) on one strand will always be opposed to the base thymine (T) on the other strand, and the base guanine (G) will be opposed to the base cytosine (C). The bases are held in apposition by their ability to hydrogen bond in this specific way. Though each individual bond is relatively weak, the net effect of many adjacent hydrogen bonded bases, together with base stacking effects, is a stable joining of the two complementary strands. These bonds can be broken by treatments such as high pH or high temperature, and these conditions result in the dissociation, or "denaturation," of the two strands. If the DNA is then placed in conditions which make hydrogen bonding of the bases thermodynamically favorable, the DNA strands will anneal, or "hybridize," and reform the original double stranded DNA. If carried out under appropriate conditions, this hybridization can be highly specific. That is, only strands with a high degree of base complementarity will be able to form stable double stranded structures. The relationship of the specificity of hybridization to reaction conditions is well known. Thus, hybridization may be used to test whether two pieces of DNA are complementary in their base sequences. It is this hybridization mechanism which facilitates the use of probes of the subject invention to readily detect and characterize DNA sequences of interest.

The probes may be RNA, DNA, or PNA (peptide nucleic acid). The probe will normally have at least about 10 bases, more usually at least about 17 bases, and may have up to about 100 bases or more. Longer probes can readily be utilized, and such probes can be, for example, several kilobases in length. The probe sequence is designed to be at least substantially complementary to a portion of a gene encoding a toxin of interest. The probe need not have perfect complementarity to the sequence to which it hybridizes. The probes may be labelled utilizing techniques which are well known to those skilled in this art.

One approach for the use of the subject invention as probes entails first identifying by Southern blot analysis of a gene bank of the Bacillus isolate all DNA segments homologous with the disclosed nucleotide sequences. Thus, it is possible, without the aid of biological analysis, to know in advance the probable activity of many new Bacillus isolates, and of the individual gene products expressed by a given Bacillus isolate. Such a probe analysis provides a rapid method for identifying potentially commercially valuable insecticidal toxin genes within the multifarious subspecies of B.t.

One hybridization procedure useful according to the subject invention typically includes the initial steps of isolating the DNA sample of interest and purifying it chemically. Either lysed bacteria or total fractionated nucleic acid isolated from bacteria can be used. Cells can be treated using known techniques to liberate their DNA (and/or RNA). The DNA sample can be cut into pieces with an appropriate restriction enzyme. The pieces can be separated by size through electrophoresisin a gel, usually agarose or acrylamide. The pieces of interest can be transferred to an immobilizing membrane.

The particular hybridization technique is not essential to the subject invention. As improvements are made in hybridization techniques, they can be readily applied.

The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. As is well known in the art, if the probe molecule and nucleic acid sample hybridize by forming a strong non-covalent bond between the two molecules, it can be reasonably assumed that the probe and sample are essentially identical. The probe's detectable label provides a means for determining in a known manner whether hybridization has occurred.

In the use of the nucleotide segments as probes, the particular probe is labeled with any suitable label known to those skilled in the art, including radioactive and non-radioactive labels. Typical radioactive labels include $^{32}$P, $^{35}$S, or the like. Non-radioactive labels include, for example, ligands such as biotin or thyroxine, as well as enzymes such as hydrolases or perixodases, or the various chemiluminescers such as luciferin, or fluorescent compounds like fluorescein and its derivatives. The probes may be made inherently fluorescent as described in International Application No. WO 93/16094.

Various degrees of stringency of hybridization can be employed. The more severe the conditions, the greater the complementarity that is required for duplex formation. Severity can be controlled by temperature, probe concentration, probe length, ionic strength, time, and the like. Preferably, hybridization is conducted under moderate to high stringency conditions by techniques well known in the art, as described, for example, in Keller, G. H., M. M. Manak (1987) *DNA Probes*, Stockton Press, New York, N.Y., pp. 169–170.

As used herein "moderate to high stringency" conditions for hybridization refers to conditions which achieve the same, or about the same, degree of specificity of hybridization as the conditions employed by the current applicants. Examples of moderate and high stringency conditions are provided herein. Specifically, hybridization of immobilized DNA on Southern blots with 32P-labeled gene-specific probes was performed by standard methods (Maniatis et al.). In general, hybridization and subsequent washes were carried out under moderate to high stringency conditions that allowed for detection of target sequences with homology to the exemplified toxin genes. For double-stranded DNA gene probes, hybridization was carried out overnight at 20–25° C. below the melting temperature (Tm) of the DNA hybrid in 6×SSPE, 5×Denhardt's solution,0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology*, R. Wu, L. Grossman and K. Moldave [eds.] Academic Press, New York 100:266–285).

Tm=81.5° C.+16.6 Log[Na+]+0.41 (%G+C)−0.61 (%formamide)−600/length of duplex in base pairs.

Washes are typically carried out as follows:

(1) Twice at room temperature for 15 minutes in 1×SSPE, 0.1% SDS (low stringency wash).

(2) Once at Tm −20° C. for 15 minutes in 0.2×SSPE, 0.1% SDS (moderate stringency wash).

For oligonucleotide probes, hybridization was carried out overnight at 10–20° C. below the melting temperature (Tm) of the hybrid in 6×SSPE, 5×Denhardt's solution, 0.1% SDS, 0.1 mg/ml denatured DNA. Tm for oligonucleotide probes was determined by the following formula:

Tm (° C.)=2(number T/A base pairs)+4(number G/C base pairs) (Suggs, S. V., T. Miyake, E. H. Kawashime, M. J. Johnson, K. Itakura, and R. B. Wallace [1981] *ICN-UCLA Symp. Dev. Biol. Using Purified Genes*, D. D. Brown [ed.], Academic Press, New York, 23:683–693).

Washes were typically carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

Low: 1 or 2×SSPE, room temperature

Low: 1 or 2×SSPE, 42° C.

Moderate: 0.2× or 1×SSPE, 65° C.

High: 0.1×SSPE, 65° C.

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

Thus, mutational, insertional, and deletional variants of the disclosed nucleotide sequences can be readily prepared by methods which are well known to those skilled in the art. These variants can be used in the same manner as the exemplified primer sequences so long as the variants have substantial sequence homology with the original sequence. As used herein, substantial sequence homology refers to homology which is sufficient to enable the variant probe to function in the same capacity as the original probe. Preferably, this homology is greaterthan 50%; more preferably, this homology is greaterthan 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

PCR Technology

Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Arnheim [1985] "Enzymatic Amplification of β-Globin Genomic Sequences and Restriction Site Analysis for Diagnosis of Sickle Cell Anemia," *Science* 230:1350–1354.). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium *Thermus aquaticus*, the amplification process can be completely automated. Other enzymes which can be used are known to those skilled in the art.

The DNA sequences of the subject invention can be used as primers for PCR amplification. In performing PCR amplification, a certain degree of mismatch can be tolerated between primer and template. Therefore, mutations, deletions, and insertions (especially additions of nucleotidesto the 5' end) of the exemplified primers fall within the scope of the subject invention. Mutations, insertions and deletions can be produced in a given primer by methods known to an ordinarily skilled artisan.

All of the U.S. patents cited herein are hereby incorporated by reference.

Following are examples which illustrate procedures for practicing the invention. These examples should not be construed as limiting. All percentages are by weight and all solvent mixture proportions are by volume unless otherwise noted.

EXAMPLE 1

Culturing of Bacillus Isolates Useful According to the Invention

Growth of Cells

The cellular host containing the Bacillus insecticidal gene may be grown in any convenient nutrient medium. These cells may then be harvested in accordance with conventional ways. Alternatively, the cells can be treated prior to harvesting.

The Bacillus cells of the invention can be cultured using standard art media and fermentation techniques. During the fermentation cycle, the bacteria can be harvested by first separating the Bacillus vegetative cells, spores, crystals, and lysed cellular debris from the fermentation broth by means well known in the art. Any Bacillus spores or crystal δ-endotoxins formed can be recovered employing well-known techniques and used as a conventional 67 -endotoxin B.t. preparation. The supernatant from the fermentation process contains toxins of the present invention. The toxins are isolated and purified employing well-known techniques.

A subculture of Bacillus isolates, or mutants thereof, can be used to inoculate the following medium, known as TB broth:

| | |
|---|---|
| Tryptone | 12 g/l |
| Yeast Extract | 24 g/l |
| Glycerol | 4 g/l |
| $KH_2PO_4$ | 2.1 g/l |
| $K_2HPO_4$ | 14.7 g/l |
| pH 7.4 | |

The potassium phosphate was added to the autoclaved broth after cooling. Flasks were incubated at 30° C. on a rotary shaker at 250 rpm for 24–36 hours.

The above procedure can be readily scaled up to large fermentors by procedures well known in the art.

The Bacillus obtained in the above fermentation, can be isolated by procedures well known in the art. A frequently-used procedure is to subject the harvested fermentation broth to separation techniques, e.g., centrifugation. In a specific embodiment, Bacillus proteins useful according the present invention can be obtained from the supernatant. The culture supernatant containing the active protein(s) can be used in bioassays.

Alternatively, a subculture of Bacillus isolates, or mutants thereof, can be used to inoculate the following peptone, glucose, salts medium:

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| pH 7.2 | |
| Salts Solution (100 ml) | |
| $MgSO_4 \cdot 7H_2O$ | 2.46 g |
| $MnSO_4 \cdot H_2O$ | 0.04 g |
| $ZnSO_4 \cdot 7H_2O$ | 0.28 g |
| $FeSO_4 \cdot 7H_2O$ | 0.40 g |
| $CaCl_2$ Solution (100 ml) | |
| $CaCl_2 \cdot 2H_2O$ | 3.66 g |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The Bacillus spores and/or crystals, obtained in the above fermentation, can be isolated by procedures well known in the art. A frequently-used procedure is to subject the harvested fermentation broth to separation techniques, e.g., centrifugation.

EXAMPLE 2

Isolation and Preparation of Cellular DNA for PCR

DNA can be prepared from cells grown on Spizizen's agar, or other minimal or enriched agar known to those skilled in the art, for approximately 16 hours. Spizizen's cas amino acid agar comprises 23.2 g/l Spizizen's minimal salts [$(NH_4)_2SO_4$, 120 g; $K_2HPO_4$, 840 g; $KH_2PO_4$, 360 g; sodium citrate, 60 g; $MgSO_4.7H_2O$, 12 g. Total: 1392 g]; 1.0 g/l vitamin-free casamino acids; 15.0 g/l Difco agar. In preparing the agar, the mixture was autoclaved for 30 minutes, then a sterile, 50% glucose solution can be added to a final concentration of 0.5% (1/100 vol). Once the cells are grown for about 16 hours, an approximately 1 $cm^2$ patch of cells can be scraped from the agar into 300 $\mu$l of 10 mM Tris-HCl (pH 8.0)-1 mM EDTA. Proteinase K was added to 50 $\mu$g/ml and incubated at 55° C. for 15 minutes. Other suitable proteases lacking nuclease activity can be used. The samples were then placed in a boiling water bath for 15 minutes to inactivate the proteinase and denature the DNA. This also precipitates unwanted components. The samples are then centrifuged at 14,000×g in an Eppendorf microfuge at room temperature for 5 minutes to remove cellular debris. The supernatants containing crude DNA were transferred to fresh tubes and frozen at −20° C. until used in PCR reactions.

Alternatively, total cellular DNA may be prepared from plate-grown cells using the QIAamp Tissue Kit from Qiagen (Santa Clarita, Calif.) following instructions from the manufacturer.

EXAMPLE 3

Use of PCR Primers to Characterize and/or Identify Toxin Genes

Two primers useful in PCR procedures were designed to identify genes that encode pesticidal toxins. Preferably, these toxins are active against lepidopteran insects. The DNA from 95 B.t. strains was subjected to PCR using these primers. Two clearly distinguishable molecular weight bands were visible in "positive" strains, as outlined below. The frequency of strains yielding a 339 bp fragment was 29/95 (31%). This fragment is referred to herein as the "339 bp fragment" even though some small deviation in the exact number of base pairs may be observed.

GARCCRTGGA AAGCAAATAA TAARAATGC (SEQ ID NO. 1)

AAARTTATCT CCCCAWGCTT CATCTCCATT TTG (SEQ ID NO. 2)

The strains which were positive for the 339 bp fragment (29 strains) were: PS11B, PS31G1, PS36A, PS49C, PS81A2, PS81F, PS81GG, PS81I, PS85A1, PS86BB1, PS86V1, PS86W1, PS89J3, PS91C2, PS94R1, PS101DD, PS158C2, PS185U2, PS192M4, PS202S, PS213E5, PS218G2, PS244A2, HD29, HD110, HD129, HD525, HD573a, and Javelin 1990.

The 24 strains which gave a larger (approximately 1.2 kb) fragment were: PS24J, PS33F2, PS45B1, PS52A1, PS62B1, PS80PP3, PS86A1, PS86Q3, PS88F16, PS29B, PS101Z2, PS123D1, PS157C1, PS169E, PS177F1, PS177G, PS185L2, PS201L1, PS204C3, PS204G4, PS242H10, PS242K17, PS244A2, PS244D1.

It was found that Bacillus strains producing lepidopteran-active proteins yielded only the 339 bp fragment. Few, if any, of the strains amplifying the approximately 1.2 kb fragment had known lepidopteran activity, but rather were coleopteran-, mite-, and/or nematode-active B.t. crystal protein producing strains.

EXAMPLE 4

DNA Sequencing of Toxin Genes Producing the 339 Fragment

PCR-amplified segments of toxin genes present in Bacillus strains can be readily sequenced. To accomplish this, amplified DNA fragments can be first cloned into the PCR DNA TA-cloning plasmid vector, pCRII, as described by the supplier (Invitrogen, San Diego, Calif.). Individual pCRII clones from the mixture of amplified DNA fragments from each Bacillus strain are chosen for sequencing. Colonies are lysed by boiling to release crude plasmid DNA. DNA templates for automated sequencing are amplified by PCR using vector-specific primers flanking the plasmid multiple cloning sites. These DNA templates are sequenced using Applied Biosystems (Foster City, Calif.) automated sequencing methodologies. The polypeptide sequences can be deduced from these nucleotide sequences.

DNA from three of the 29 B.t. strains which amplified the 339 bp fragments were sequenced. A DNA sequence encoding a toxin from strain PS36A is shown in SEQ ID NO. 3. An amino acid sequence for the 36A toxin is shown in SEQ ID. NO 4. A DNA sequence encoding a toxin from strain PS81F is shown in SEQ ID NO. 5. An amino acid sequence for the 81F toxin is shown in SEQ ID. NO 6. A DNA sequence encoding a toxin from strain Javelin 1990 is shown in SEQ ID NO. 7. An amino acid sequence for the Javelin 1990 toxin is shown in SEQ ID. NO 8.

EXAMPLE 5

Determination of DNA Sequences from Additional Genes Encoding Toxins from Strains PS158C2 and PS49C Genes encoding novel toxins were identified from isolates PS158C2 and PS49C as follows: Total cellular DNA was extracted from B.t. strains using Qiagen (Santa Clarita, Calif.) Genomic-tip 500/G DNA extraction kits according to the supplier and was subjected to PCR using the oligonucleotide primer pairs listed below. Amplified DNA fragments were purified on Qiagen PCR purification columns and were used as templates for sequencing.

For PS158C2, the primers used were as follows.
158C2 PRIMER A:

GCTCTAGAAGGAGGTAACTTATGAACAAGAATAATACTAAATTAAGC (SEQ ID NO. 9)

339 reverse:

AAARTTATCT CCCCAWGCTT CATCTCCATT TTG (SEQ ID NO. 2)

The resulting PCR-amplified DNA fragment was approximately 2 kbp in size. This DNA was partially sequenced by dideoxy chain termination using automated DNA sequencing technology (Pekin Elmer/AppliedBiosystems, Foster City, Calif.). A DNA sequence encoding a portion of a soluble toxin from PS158C2 is shown in SEQ ID NO. 10.

For PS49C, two separate DNA fragments encoding parts of a novel toxin gene were amplified and sequenced. The first fragment was amplified using the following primer pair:
49C PRIMER A:

CATCCTCCCTACACTTTCTAA (SEQ ID NO. 11)

339 reverse:

AAARTTATCT CCCCAWGCTT CATCTCCATT TTG (SEQ ID NO. 2)

The resulting approximately 1 kbp DNA fragment was used as a template for automated DNA sequencing. A sequence of a portion of a toxin gene from strain PS49C is shown in SEQ ID NO. 12.

The second fragment was amplified using the following primer pair:
49C PRIMER B:

AAATTATGCGCTAAGTCTGC (SEQ ID NO. 13)

49C PRIMER C:

TTGATCCGGACATAATAAT (SEQ ID NO. 14)

The resulting approximately 0.57 kbp DNA fragment was used as a template for automated DNA sequencing. An additional sequence of a portion of the toxin gene from PS49C is shown in SEQ ID NO. 15.

EXAMPLE 6

Additional Primers Useful for Characterizing and/or Identifying Toxin Genes

The following primer pair can be used to identify and/or characterize genes of the
SUP-1 family:
SUP-1A:

GGATTCGTTATCAGAAA (SEQ ID NO. 53)

SUP-1B:

CTGTYGCTAACAATGTC (SEQ ID NO. 54)

These primers can be used in PCR procedures to amplify a fragment having a predicted size of approximately 370 bp. A band of the predicted size was amplified from strains PS158C2 and PS49C.

EXAMPLE 7

Additional Primers Useful for Characterizing and/or Identifying Toxin Genes

Another set of PCR primers can be used to identify and/or characterize additional genes encoding pesticidal toxins. The sequences of these primers were as follows:

GGRTTAMTTGGRTAYTATTT (SEQ ID NO. 16)

ATATCKWAYATTKGCATTTA (SEQ ID NO. 17)

Redundant nucleotide codes used throughout the subject disclosure are in accordance with the IUPAC convention and include:

R=A or G
M=A or C
Y=C or T
K=G or T
W=A or T

EXAMPLE 8

Identification and Sequencing of Genes Encoding Novel Soluble Protein Toxins from Bacillus Strains PCR using primers SEQ ID NO. 16 and SEQ ID NO. 17 was performed on total cellular genomic DNA isolated from a broad range of Bt strains. Those samples yielding an approximately 1 kb band were selected for characterization by DNA sequencing. Amplified DNA fragments were first cloned into the PCR DNA TA-cloning plasmid vector, pCR2.1, as described by the supplier (Invitrogen, San Diego, Calif.). Plasmids were isolated from recombinant clones and tested for the presence of an approximately 1 kbp insert by PCR using the plasmid vector primers, T3 and T7.

The following strains yielded the expected band of approximately 1000 bp, thus indicating the presence of a MIS-type toxin gene: PS10E1, PS31J2, PS33D2, PS66D3, PS68F, PS69AA2, PS168G1, PS177C8, PS177I8, PS185AA2, PS196F3, PS196J4, PS197T1, PS197U2, PS202E1, KB33, KB38, PS33F1, PS157C1 (157C1-A), PS201Z, PS31F2, and PS185Y2.

Plasmids were then isolated for use as sequencing templates using QIAGEN (Santa Clarita, Calif.) miniprep kits as described by the supplier. Sequencing reactions were performed using the Dye Terminator Cycle Sequencing Ready Reaction Kit from PE Applied Biosystems. Sequencing reactions were run on a ABI PRISM 377 Automated Sequencer. Sequence data was collected, edited, and assembled using the ABI PRISM 377 Collection, Factura, and AutoAssembler software from PE ABI.

DNA sequences were determined for portions of novel toxin genes from the following isolates: PS10E1, PS31J2, PS33D2, PS66D3, PS68F, PS69AA2, PS168G1, PS177C8, PS177I8, PS185AA2, PS196F3, PS196J4, PS197T1, PS197U2, PS202E1, KB33, KB38, PS33F1, PS157C1 (157C1-A), PS201Z, PS31F2, and PS185Y2. Polypeptide sequences were deduced for portions of the encoded, novel soluble toxins from the following isolates: PS10E1, PS31J2, PS33D2, PS66D3, PS68F, PS69AA2, PS177C8, PS177I8, PS185AA2, PS196F3, PS196J4, PS197T1, PS197U2, PS202E1, and PS157C1 (toxin 157C1-A). These nucleotide sequences and amino acid sequences are shown in SEQ ID NOS. 18 to 48 and SEQ ID NOS. 139–144.

EXAMPLE 9

Restriction Fragment Length Polymorphism (RFLP) of Toxins from *Bacillus thuringiensis* Strains Total cellular DNA was prepared from various *Bacillus thuriengensis* (B.t.) strains grown to an optical density of 0.5–0.8 at 600 nm visible light. DNA was extracted using the Qiagen Genomic-tip 500/G kit and Genomic DNA Buffer Set according to protocol for Gram positive bacteria (Qiagen Inc.; Valencia, Calif.).

Standard Southern hybridizations using $^{32}$P-lableled probes were used to identify and characterize novel toxin genes within the total genomic DNA preparations. Prepared total genomic DNA was digested with various restriction enzymes, electrophoresed on a 1% agarose gel, and immobilized on a supported nylon membrane using standard methods (Maniatis et al.).

PCR-amplified DNA fragments 1.0–1.1 kb in length were gel purified for use as probes. Approximately 25 ng of each DNA fragment was used as a template for priming nascent DNA synthesis using DNA polymerase I Klenow fragment (New England Biolabs), random hexanucleotide primers (Boehringer Mannheim) and $^{32}$PdCTP.

Each $^{32}$P-lableled fragment served as a specific probe to its corresponding genomic DNA blot. Hybridizations of immobilized DNA with randomly labeled $^{32}$P probes were performed in standard aqueous buffer consisting of 5×SSPE, 5×Denhardt's solution, 0.5% SDS, 0.1 mg/ml at 65° C. overnight. Blots were washed under moderate stringency in 0.2×SSC, 0.1% SDS at 65° C. and exposed to film. RFLP data showing specific hybridization bands containing all or part of the novel gene of interest was obtained for each strain.

TABLE 4

| (Strain)/ Gene Name | Probe Seq I.D. Number | RFLP Data (approximate band sizes) |
|---|---|---|
| (PS)10E1 | 18 | EcoRI: 4 and 9 kbp, EcoRV: 4.5 and 6 kbp, KpnI: 12 and 24 kbp, SacI: 13 and 24 kbp, SalI: >23 kbp, XbaI: 5 and 15 kbp |
| (PS)31J2 | 20 | ApaI: >23 kbp, BglII: 6.5 kbp, PstI: >23 kbp, SacI: >23 kbp, SalI: >23 kbp, XbaI: 5 kbp |
| (PS)33D2 | 22 | EcoRI: 10 kbp, EcoRV: 15 kbp, HindIII: 18 kbp, KpnI: 9.5 kbp, PstI: 8 kbp |
| (PS)66D3 | 24 | BamHI: 4.5 kbp, HindIII: >23 kbp, KpnI: 23 kbp, PstI: 15 kbp, XbaI: >23 kbp |
| (PS)68F | 26 | EcoRI: 8.5 and 15 kbp, EcoRV: 7 and 18 kbp, HindIII: 2.1 and 9.5 kbp, PstI: 3 and 18 kbp, XbaI: 10 and 15 kbp |
| (PS)69AA2 | 28 | EcoRV: 9.5 kbp, HindIII: 18 kbp, KpnI: 23 kbp, NheI: >23 kbp, PstI: 10 kbp, SalI: >23 kbp |
| (PS)168G1 | 30 | EcoRI: 10 kbp, EcoRV: 3.5 kbp, NheI: 20 kbp, PstI: 20 kbp, SalI: >23 kbp, XbaI: 15 kbp |
| (PS)177I8 | 33 | BamHI: >23 kbp, EcoRI: 10 kbp, HindIII: 2 kbp, SalI: >23 kbp, XbaI: 3.5 kbp |
| (PS)185AA2 | 35 | EcoRI: 7 kbp, EcoRV: 10 kbp (&3.5kbp?), NheI: 4 kbp, PstI: 3 kbp, SalI: >23 kbp, XbaI: 4 kbp |
| (PS)196F3 | 37 | EcoRI: 8 kbp, EcoRV: 9 kbp, NheI: 18 kbp, PstI: 18 kbp, SalI: 20 kbp, XbaI: 7 kbp |

TABLE 4-continued

| (Strain)/ Gene Name | Probe Seq I.D. Number | RFLP Data (approximate band sizes) |
|---|---|---|
| (PS)196J4 | 39 | BamHI: >23 kbp, EcoRI: 3.5 and 4.5 kbp, PstI: 9 and 24 kbp, SalI: >23 kbp, XbaI: 2.4 and 12 kbp |
| (PS)197T1 | 41 | HindIII: 10 kbp, KpnI: 20 kbp, PstI: 20 kbp, SacI: 20 kbp, SpeI: 15 kbp, XbaI: 5 kbp |
| (PS)197U2 | 43 | EcoRI: 5 kbp, EcoRV: 1.9 kbp, NheI: 20 kbp, PstI: 23 kbp, SalI: >23 kbp, XbaI: 7 kbp |
| (PS)202E1 | 45 | EcoRV: 7 kbp, KpnI: 12 kbp, NheI: 10 kbp, PstI: 15 kbp, SalI: 23 kbp, XbaI: 1.8 kbp |
| KB33 | 47 | EcoRI: 9 kbp, EcoRV: 6 kbp, HindIII: 8 kbp, KpnI: >23 kbp, NheI: 22 kbp, SalI: >23 kbp |
| KB38 | 48 | BamHI: 5.5 kbp, EcoRV: 22 kbp, HindIII: 2.2 kbp NheI: 20 kbp, PstI: >23 kbp |

In separate experiments, alternative probes for MIS and WAR genes were used to detect novel toxin genes on Southern blots of genomic DNA by $^{32}$P autoradiography or by non-radioactive methods using the DIG nucleic acid labeling and detection system (Boehringer Mannheim; Indianapolis, Ind.). DNA fragments approximately 2.6 kbp (PS177C8 MIS toxin gene; SEQ ID NO. 31) and 1.3 kbp (PS177C8 WAR toxin gene; SEQ ID NO. 51) in length were PCR amplified from plasmid pMYC2450 and used as the probes for all strains listed. Fragments were gel purified and approximately 25 ng of each DNA fragment was randomly labeled with $^{32}$P for radioactive detection or approximately 300 ng of each DNA fragment was randomly labeled with the DIG High Prime kit for nonradioactive detection. Hybridization of immobilized DNA with randomly labeled $^{32}$P probes were performed in standard formamide conditions: 50% formamide, 5×SSPE, 5×Denhardt's solution, 2% SDS, 0.1 mg/ml sonicated sperm DNA at 42° C. overnight. Blots were washed under low stringency in 2×SSC, 0.1% SDS at 42° C. and exposed to film. RFLP data showing DNA bands containing all or part of the novel gene of interest was obtained for each strain.

RFLP data using Probe 177C8-MIS (SEQ ID NO. 31) were as follows:

TABLE 5

| RFLP Class | Strain Name(s) | RFLP Data (approximate band size in base pairs) |
|---|---|---|
| A | 177C8, 74H3, 66D3 | HindIII: 2,454; 1,645<br>XbaI: 14,820; 9,612; 8,138; 5,642; 1,440 |
| B | 177I8 | HindIII: 2,454<br>XbaI: 3,500 (very faint 7,000) |
| C | 66D3 | HindIII: 2,454 (faint 20,000)<br>XbaI: 3,500 (faint 7,000) |
| D | 28M, 31F2, 71G5, 71G7, 71I1, 71N1, 146F, 185Y2, 201JJ7, KB73, KB68B46-2, KB71A35-4, KB71A116-1 | HindIII: 11,738; 7,614<br>XbaI: 10,622; 6,030 |
| $D_1$ | 70B2, 71C2 | HindIII: 11,738; 8,698; 7,614<br>XbaI: 11,354; 10,622; 6,030 |
| E | KB68B51-2, KB68B55-2 | HindIII: 6,975; 2,527<br>XbaI: 10,000; 6,144 |
| F | KB53A49-4 | HindIII: 5,766<br>XbaI: 6,757 |
| G | 86D1 | HindIII: 4,920<br>XbaI: 11,961 |

TABLE 5-continued

| RFLP Class | Strain Name(s) | RFLP Data (approximate band size in base pairs) |
|---|---|---|
| H | HD573B, 33F1, 67B3 | HindIII: 6,558; 1,978<br>XbaI: 7,815; 6,558 |
| I | 205C, 40C1 | HindIII: 6,752<br>XbaI: 4,618 |
| J | 130A3, 143A2, 157C1 | HindIII: 9,639; 3,943, 1,954; 1,210<br>XbaI: 7,005; 6,165; 4,480; 3,699 |
| K | 201Z | HindIII: 9,639; 4,339<br>XbaI: 7,232; 6,365 |
| L | 71G4 | HindIII: 7,005<br>XbaI: 9.639 |
| M | KB42A33-8, KB71A72-1, KB71A133-11 | HindIII: 3,721<br>XbaI: 3,274 |
| N | KB71A134-2 | HindIII: 7,523<br>XbaI: 10,360; 3,490 |
| O | KB69A125-3, KB69A127-7, KB69A136-2, KB71A20-4 | HindIII: 6,360; 3,726; 1,874; 1,098<br>XbaI: 6,360; 5,893; 5,058; 3,726 |

RFLP data using Probe 177C8-WAR (SEQ ID NO. 51) were as follows:

TABLE 6

| RFLP Class | Strain Name(s) | RFLP Data (approximate band size in base pairs) |
|---|---|---|
| A | 177C8, 74H3 | HindIII: 3,659, 2,454, 606<br>XbaI: 5,457, 4,469, 1,440, 966 |
| B | 177I8, 66D3 | data unavailable |
| C | 28M, 31F2, 71G5, 71G7, 71I1, 71N1, 146F, 185Y2, 201JJ7, KB73, KB68B46-2, KB71A35-4, KB71A116-1 | HindIII: 7,614<br>XbaI: 10,982, 6,235 |
| $C_1$ | 70B2, 71C2 | HindIII: 8,698, 7,614<br>XbaI: 11,354, 6,235 |
| D | KB68B51-2, KB68B55-2 | HindIII: 7,200<br>XbaI: 6,342 (and 11,225 for 51-2)(and 9,888 for 55-2) |
| E | KB53A49-4 | HindIII: 5,766<br>XbaI: 6,757 |
| F | HD573B, 33F1, 67B3 | HindIII: 3,348, 2,037 (and 6,558 for HD573B only)<br>XbaI: 6,953 (and 7,815, 6,185 for HD573B only) |
| G | 205C, 40C1 | HindIII: 3,158<br>XbaI: 6,558, 2,809 |
| H | 130A3, 143A2, 157C1 | HindIII: 4,339, 3,361, 1,954, 660, 349<br>XbaI: 9,043, 4,203, 3,583, 2,958, 581, 464 |
| I | 201Z | HindIII: 4,480, 3,819, 703<br>XbaI: 9,336, 3,256, 495 |
| J | 71G4 | HindIII: 7,005<br>XbaI: 9,639 |
| K | KB42A33-8, KB71A72-1, KB71A133-11 | no hybridization signal |
| L | KB71A134-2 | HindIII: 7,523<br>XbaI: 10,360 |
| M | KB69A125-3, KB69A127-7, KB69A136-2, KB71A20-4 | HindIII: 5,058; 3,726; 3,198; 2,745; 257<br>XbaI: 5,255; 4,341; 3,452; 1,490; 474 |

EXAMPLE 10

Use of Additional PCR Primers for Characterizing and/or Identifying Novel Genes

Another set of PCR primers can be used to identify additional novel genes encoding pesticidal toxins. The sequences of these primers were as follows:

ICON-forward:

CTTGAYTTTAAARATGATRTA (SEQ ID NO. 49)

ICON-reverse:

AATRGCSWATAAATAMGCACC (SEQ ID NO. 50)

These primers can be used in PCR procedures to amplify a fragment having a predicted size of about 450 bp.

Strains PS177C8, PS177I8, and PS66D3 were screened and were found to have genes amplifiable with these ICON primers. A sequence of a toxin gene from PS177C8 is shown in SEQ ID NO. 51. An amino acid sequence of the 177C8-ICON toxin is shown in SEQ ID NO. 52.

EXAMPLE 11

Use of Mixed Primer Pairs to Characterize and/or Identify Toxin Genes

Various combinations of the primers described herein can be used to identify and/or characterize toxin genes. PCR conditions can be used as indicated below:

| | SEQ ID NO. 16/17 | SEQ ID NO. 49/50 | SEQ ID NO. 49/17 |
|---|---|---|---|
| Pre-denature | 94° C. 1 min. | 94° C. 1 min. | 94° C. 1 min. |
| Program | 94° C. 1 min. | 94° C. 1 min. | 94° C. 1 min. |

-continued

| | SEQ ID NO. 16/17 | SEQ ID NO. 49/50 | SEQ ID NO. 49/17 |
|---|---|---|---|
| Cycle | 42° C. 2 min.<br>72° C. 3 min. +<br>5 sec/cycl<br>Repeat cycle<br>29 times<br>Hold 4° C. | 42° C. 2 min.<br>72° C. 3 min. +<br>5 sec/cycl<br>Repeat cycle<br>29 times<br>Hold 4° C. | 42° C. 2 min.<br>72° C. 3 min. +<br>5 sec/cycl<br>Repeat cycle<br>29 times<br>Hold 4° C. |

Using the above protocol, a strain harboring a MIS-type of toxin would be expected to yield a 1000 bp fragment with the SEQ ID NO. 16/17 primer pair. A strain harboring a WAR-type of toxin would be expected to amplify a fragment of about 475 bp with the SEQ ID NO. 49/50 primer pair, or a fragment of about 1800 bp with the SEQ ID NO. 49/17 primer pair. The amplified fragments of the expected size were found in four strains. The results are reported in Table 7.

TABLE 7

| | Approximate Amplified Fragment Sizes (bp) | | |
|---|---|---|---|
| Strain | SEQ ID NO. 16/17 | SEQ ID NO. 49/50 | SEQ ID NO. 49/17 |
| PS66D3 | 1000 | 900, 475 | 1800 |
| PS177C8 | 1000 | 475 | 1800 |
| PS177I8 | 1000 | 900, 550, 475 | 1800 |
| PS217U2 | 1000 | 2500, 1500, 900, 475 | no band detected |

EXAMPLE 12

Characterization and/or Identification of WAR Toxins

In a further embodiment of the subject invention, pesticidal toxins can be characterized and/or identified by their level of reactivity with antibodies to pesticidal toxins exemplified herein. In a specific embodiment, antibodies can be raised to WAR toxins such as the toxin obtainable from PS177C8a. Other WAR toxins can then be identified and/or characterized by their reactivity with the antibodies. In a preferred embodiment, the antibodies are polyclonal antibodies. In this example, toxins with the greatest similarity to the 177C8a-WAR toxin would have the greatest reactivity with the polyclonal antibodies. WAR toxins with greater diversity react with the 177C8a polyclonal antibodies, but to a lesser extent. Toxins which immunoreact with polyclonal antibodies raised to the 177C8a WAR toxin can be obtained from, for example, the isolates designated PS177C8a, PS177I8, PS66D3, KB68B55-2, PS185Y2, PS146F, KB53A49-4, PS175I4, KB68B51-2, PS28K1, PS31F2, KB58B46-2, PS146D, PS74H3, PS28M, PS71G6, PS71G7, PS71I1, PS71N1, PS201JJ7, KB73, KB68B46-2, KB71A35-4, KB71A116-1, PS70B2, PS 71C2, PS86D1, HD573B, PS33F1, PS67B3, PS205C, PS40C1, PS130A3, PS143A2, PS157C1, PS201Z, PS71G4, KB42A33-8, KB71A72-1, KB71A133-11, KB71A134-2, KB69A125-3, KB69A127-7, KB69A136-2, and KB71A20-4. Such diverse WAR toxins can be further characterized by, for example, whether or not their genes can be amplified with ICON primers. For example, the following isolates do not have polynucleotide sequences which are amplified by ICON primers: PS177C8a, PS177I8, PS66D3, KB68B55-2, PS185Y2, PS146F, KB53A49-4, PS175I4, KB68B51-2, PS28K1, PS31F2, KB58B46-2, and PS146D. Of these, isolates PS28K1, PS31F2, KB68B46-2, and PS146D show the weakest antibody reactivity, suggesting advantageous diversity.

EXAMPLE 13

Bioassays for Activity Against Lepidopterans and Coleopterans

Biological activity of the toxins and isolates of the subject invention can be confirmed using standard bioassay procedures. One such assay is the budworm-bollworm (*Heliothis virescens* [Fabricius] and *Helicoverpa zea* [Boddie]) assay. Lepidoptera bioassays were conducted with either surface application to artificial insect diet or diet incorporation of samples. All Lepidopteran insects were tested from the neonate stage to the second instar. All assays were conducted with either toasted soy flour artificial diet or black cutworm artificial diet (BioServ, Frenchtown, N.J.).

Diet incorporation can be conducted by mixing the samples with artificial diet at a rate of 6 mL suspension plus 54 mL diet. After vortexing, this mixture is poured into plastic trays with compartmentalized3-ml wells (Nutrend Container Corporation, Jacksonville, Fla.).

A water blank containing no B.t. serves as the control. First instar larvae (USDA-ARS, Stoneville, Miss.) are placed onto the diet mixture. Wells are then sealed with Mylar sheeting (ClearLam Packaging, Ill.) using a tacking iron, and several pinholes are made in each well to provide gas exchange. Larvae were held at 25° C. for 6 days in a 14:10 (light:dark) holding Mortality and stunting are recorded after six days.

Bioassay by the top load method utilizes the same sample and diet preparations as listed above. The samples are applied to the surface of the insect diet. In a specific embodiment, surface area ranged from 0.3 to approximately 0.8 $cm^2$ depending on the tray size, 96 well tissue culture plates were used in addition to the format listed above. Following application, samples are allowed to air dry before insect infestation. A water blank containing no B.t. can serve as the control. Eggs are applied to each treated well and were then sealed with Mylar sheeting (ClearLam Packaging, Ill.) using a tacking iron, and pinholes are made in each well to provide gas exchange. Bioassays are held at 25° C. for 7 days in a 14:10 (light:dark) or 28° C. for 4 days in a 14:10 (light:dark) holding room. Mortality and insect stunting are recorded at the end of each bioassay.

Another assay useful according to the subject invention is the Western corn rootworm assay. Samples can be bioassayed against neonate western corn rootworm larvae (*Diabrotica virgifera virgifera*) via top-loading of sample onto an agar-based artificial diet at a rate of 160 ml/$cm^2$. Artificial diet can be dispensed into 0.78 $cm^2$ wells in 48-well tissue culture or similar plates and allowed to harden. After the diet solidifies, samples are dispensed by pipette onto the diet surface. Excess liquid is then evaporated from the surface prior to transferring approximately three neonate larvae per well onto the diet surface by camel's hair brush. To prevent insect escape while allowing gas exchange, wells are heat-sealed with 2-mil punched polyester film with 27HT adhesive (Oliver Products Company, Grand Rapids, Mich.). Bioassays are held in darkness at 25° C., and mortality scored after four days.

Analogous bioassays can be performed by those skilled in the art to assess activity against other pests, such as the black cutworm (*Agrotis ipsilon*).

Results are shown in Table 8.

TABLE 8

Genetics and function of concentrated *B.t.* supernatants for lepidopteran and coleopteran activity

| Strain | Approx. 339 bp PCR fragment | Total Protein ($\mu$g/cm$^2$) | ca. 80–100 kDa protein ($\mu$g/cm$^2$) | H. virescens % mortality | H. virescens Stunting | H. zen % mortality | H. zen Stunting | Diabrotica % mortality |
|---|---|---|---|---|---|---|---|---|
| PS31G1 | + | 8.3 | 2.1 | 70 | yes | 39 | yes | NT |
| PS49C | + | 13.6 | 1.5 | 8 | yes | 8 | no | NT |
| PS80JJ1 | – | 8.0 | NT | 18 | no | 13 | no | NT |
| PS80JJ1 (#2) | – | 35 | NT | — | — | — | — | 43 |
| PS81A2 (#1) | – | 30.3 | 2.3 | 100 | yes | 38 | yes | NT |
| PS81A2 (#2) | + | 18.8 | 1.6 | 38 | yes | 13 | no | NT |
| PS81F | ++ | 26 | 5.2 | 100 | yes | 92 | yes | NT |
| PS81I | + | 10.7 | 1.7 | 48 | yes | 13 | no | NT |
| PS86B1 (#1) | – | 23.2 | 4.5 | 17 | no | 13 | no | — |
| PS86B1 (#2) | – | 90 | 17.5 | — | — | — | — | 35 |
| PS86B1 (#3) | – | 35 | 6.8 | — | — | — | — | 10 |
| PS122D3 (#1) | – | 33.2 | 1.8 | 21 | no | 21 | no | — |
| PS122D3 (#2) | – | 124 | 6.7 | — | — | — | — | 45 |
| PS122D3 (#3) | – | 35 | 1.9 | — | — | — | — | 16 |
| PS123D1 (#1) | – | 10.7 | NT | 0 | no | 0 | no | — |
| PS123D1 (#2) | – | 69 | NT | — | — | — | — | 54 |
| PS123D1 (#3) | – | 35 | NT | — | — | — | — | 21 |
| PS123D1 (#4) | – | 17.8 | NT | 5 | no | 4 | no | NT |
| PS149B1 (#1) | NT | 9 | NT | 0 | no | 0 | yes | NT |
| PS149B1 (#2) | NT | 35 | NT | — | — | — | — | 50 |
| PS157C1 (#1) | – | 24 | 2 | 43 | yes | 13 | yes | — |
| PS157C1 (#2) | – | 93 | 8 | — | — | — | — | 40 |
| PS157C1 (#3) | – | 35 | 3 | — | — | — | — | 18 |
| PS185L2 (#1) | – | 2 | NT | 8 | no | 0 | no | NT |
| PS185L2 (#2) | – | 3 | NT | 10 | no | 25 | no | NT |
| PS185U2 | + | 23.4 | 2.9 | 100 | yes | 100 | yes | NT |
| PS192M4 | + | 10.7 | 2.0 | 9 | no | 4 | yes | NT |
| HD129 | + | 44.4 | 4.9 | 100 | yes | 50 | yes | NT |
| Javelin 1990 | ++ | 43.2 | 3.6 | 100 | yes | 96 | yes | NT |
| water | | | | 0–8 | — | 0–4 | — | 12 |

*NT = not tested

EXAMPLE 14

Results of Western Corn Rootworm Bioassays and Further Characterization of the Toxins Concentrated liquid supernatant solutions, obtained according to the subject invention, were tested for activity against Western corn rootworm (WCRW). Supernatants from the following isolates were found to cause mortality against WCRW: PS10E1, PS31F2, PS31J2, PS33D2, PS66D3, PS68F, PS80JJ1, PS146D, PS175I4, PS177I8, PS196J4, PS197T1, PS197U2, KB33, KB53A49-4, KB68B46-2, KB68B51-2, KB68B55-2, PS177C8, PS69AA2, KB38, PS196F3, PS168G1, PS202E1, PS217U2 and PS185AA2.

Supernatants from the following isolates were also found to cause mortality against WCRW: PS205A3, PS185V2, PS234E1, PS71G4, PS248N10, PS191A21, KB63B19-13, KB63B19-7, KB68B62-7, KB68B63-2, KB69A125-1, KB69A125-3, KB69A125-5, KB69A127-7, KB69A132-1, KB69B2-1, KB70B5-3, KB71A125-15, and KB71A35-6; it was confirmed that this activity was heat labile. Furthermore, it was determined that the supernatants of the following isolates did not react (yielded negative test results) with the WAR antibody (see Example 12), and did not react with the MIS (SEQ ID NO. 31) and WAR (SEQ ID NO. 51) probes: PS205A3, PS185V2, PS234E1, PS71G4, PS248N10, PS191A21, KB63B19-13, KB63B19-7, KB68B62-7, KB68B63-2, KB69A125-1, KB69A125-5, KB69A132-1, KB69B2-1, KB70B5-3, KB71A125-15, and KB71A35-6; the supernatants of isolates KB69A125-3 and KB69A127-7 yielded positive test results.

EXAMPLE 15

Results of Budworm/Bollworm Bioassays

Concentrated liquid supernatant solutions, obtained according to the subject invention, were tested for activity against *Heliothis virescens* (H v.) and *Helicoverpa zea* (H.z.). Supernatants from the following isolates were tested and were found to cause mortality against Hv.: PS157C1, PS31G1, PS49C, PS81F, PS81I, Javelin 1990, PS158C2, PS202S, PS36A, HD110, and HD29. Supernatants from the following isolates were tested are were foundto cause significant mortality against H.z.: PS31G1, PS49C, PS81F, PS81I, PS157C1, PS158C2, PS36A, HD110, and Javelin 1990.

EXAMPLE 16

Target Pests

Toxins of the subject invention can be used, alone or in combination with other toxins, to control one or more non-mammalianpests. These pests may be, for example, those listed in Table 9. Activity can readily be confirmed using the bioassays provided herein, adaptations of these bioassays, and/or other bioassays well known to those skilled in the art.

TABLE 9

| Target pest species | |
|---|---|
| ORDER/Common Name | Latin Name |
| LEPIDOPTERA | |
| European Corn Borer | *Ostrinia nubilalis* |
| European Corn Borer resistant to Cry1A | *Ostrinia nubilalis* |
| Black Cutworm | *Agrotis ipsilon* |
| Fall Armyworm | *Spodoptera frugiperda* |
| Southwestern Corn Borer | *Diatraea grandiosella* |
| Corn Earworm/Bollworm | *Helicoverpa zea* |
| Tobacco Budworm | *Heliothis virescens* |
| Tobacco Budworm Rs | *Heliothis virescens* |
| Sunflower Head Moth | *Homeosoma ellectellum* |
| Banded Sunflower Moth | *Cochylis hospes* |
| Argentine Looper | *Rachiplusia nu* |
| Spilosoma | *Spilosoma virginica* |
| Bertha Armyworm | *Mamestra configurata* |
| Diamondback Moth | *Plutella xylostells* |
| COLEOPTERA | |
| Red Sunflower Seed Weevil | *Smicronyx fulvus* |
| Sunflower Stem Weevil | *Cylindrocopturus adspersus* |
| Sunflower Beetle | *Zygoramma exclamationis* |
| Canola Flea Beetle | *Phyllotreta cruciferae* |
| Western Corn Rootworm | *Diabrotica virgifera virgifera* |
| DIPTERA | |
| Hessian Fly | *Mayetiola destructor* |
| HOMOPTERA | |
| Greenbug | *Schizaphis graminum* |
| HEMIPTERA | |
| Lygus Bug | *Lygus lineolaris* |
| NEMATODA | *Heterodera glycines* |

EXAMPLE 17

Insertion of Toxin Genes Into Plants

One aspect of the subject invention is the transformation of plants with genes encoding the insecticidal toxin of the present invention. The transformed plants are resistant to attack by the target pest.

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higherplants. The vectors comprise, for example, pBR322, pUC series, M13mp series, pACYC184, etc. Accordingly, the sequence encoding the Bacillus toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformationagent, fusion, injection, biolistics (microparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters et al. [1978] *Mol. Gen. Genet.* 163:181–187). The Agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives. In biolistic transformation, plasmid DNA or linear DNA can be employed.

The transformedcells are regeneratedinto morphologicallynormal plants in the usual manner. If a transformation event involves a germ line cell, then the inserted DNA and corresponding phenotypic trait(s) will be transmitted to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831. Also, advantageously, plants encoding a truncated toxin will be used. The truncated toxin typically will encode about 55% to about 80% of the full length toxin. Methods for creating synthetic Bacillus genes for use in plants are known in the art.

It should be understood that the examples and embodiments described herein are for illustrative purposes only and that various modifications or changes in light thereof will be suggested to persons skilled in the art and are to be included within the spirit and purview of this application.

What is claimed is:

1. An isolated polynucleotide which encodes a pesticidally active protein wherein the full complement of a nucleotide sequence selected from the group consisting of SEQ ID NO:20, SEQ ID NO:37, SEQ ID NO:39, SEQ ID NO:43, SEQ ID NO:139, and SEQ ID NO:143 hybridizes with a polynucleotide molecule that codes for said protein, wherein hybridization occurs in 5×SSPE, 5×Denhardt's solution, 0.5%SDS at 65° C., and wash occurs at 0.1×SSPE and 0.1% SDS at a temperature of 65° C.

2. The isolated polynucleotide of claim 1 wherein said nucleotide sequence is SEQ ID NO:20.

3. The isolated polynucleotide of claim 1 wherein said nucleotide sequence is SEQ ID NO:37.

4. The isolated polynucleotide of claim 1 wherein said nucleotide sequence is SEQ ID NO:39.

5. The isolated polynucleotide of claim 1 wherein said nucleotide sequence is SEQ ID NO:43.

6. The isolated polynucleotide of claim 1 wherein said nucleotide sequence is SEQ ID NO:139.

7. The isolated polynucleotide of claim 1 wherein said nucleotide sequence is SEQ ID NO:143.

8. An isolated polynucleotide which encodes a pesticidally active protein wherein said protein comprises an amino acid sequence selected from the group consisting of SEQ ID NO:21, SEQ ID NO:38, SEQ ID NO:40, and SEQ ID NO:140.

9. The polynucleotide of claim 8 wherein said amino acid sequence is SEQ ID NO:21.

10. The polynucleotide of claim 8 wherein said amino acid sequence is SEQ ID NO:38.

11. The polynucleotide of claim 8 wherein said amino acid sequence is SEQ ID NO:40.

12. The polynucleotide of claim 8 wherein said amino acid sequence is SEQ ID NO:140.

13. A recombinant plant host comprising an isolated polynucleotide which encodes a pesticidally active protein wherein the full complement of a nucleotide sequence selected from the group consisting of SEQ ID NO:20, SEQ ID NO:37, SEQ ID NO:39, SEQ ID NO:43, SEQ ID NO:139, and SEQ ID NO:143 hybridizes with a polynucleotide molecule that codes for said protein, wherein hybridization occurs in 5×SSPE, 5×Denhardt's solution, 0.5%SDS at 65° C. and wash occurs at 0.1×SSPE and 0.1% SDS at a temperature of 65° C.

14. The recombinant host of claim 13 wherein said nucleotide sequence is SEQ ID NO:20.

15. The recombinant host of claim 13 wherein said nucleotide sequence is SEQ ID NO:37.

16. The recombinant host of claim 13 wherein said nucleotide sequence is SEQ ID NO:39.

17. The recombinant host of claim 13 wherein said nucleotide sequence is SEQ ID NO:43.

18. The recombinant host of claim 13 wherein said nucleotide sequence is SEQ ID NO:139.

19. The recombinant host of claim 13 wherein said nucleotide sequence is SEQ ID NO:143.

20. A recombinant plant host comprising an isolated polynucleotide which encodes a pesticidally active protein wherein said protein comprises an amino acid sequence selected from the group consisting of SEQ ID NO:21, SEQ ID NO:38, SEQ ID NO:40, and SEQ ID NO:140.

21. The recombinant host of claim 20 wherein said amino acid sequence is SEQ ID NO:21.

22. The recombinant host of claim 20 wherein said amino acid sequence is SEQ ID NO:38.

23. The recombinant host of claim 20 wherein said amino acid sequence is SEQ ID NO:40.

24. The recombinant host of claim 20 wherein said amino acid sequence is SEQ ID NO:140.

25. A recombinant plant cell comprising an isolated polynucleotide that encodes a pesticidally active protein wherein the full complement of a nucleotide sequence selected from the group consisting of SEQ ID NO:20, SEQ ID NO:37, SEQ ID NO:39, SEQ ID NO:43, SEQ ID NO:139, and SEQ ID NO:143 hybridizes with a polynucleotide molecule that codes for said protein, wherein hybridization occurs in 5×SSPE, 5×Denhardt's solution, 0.5%SDS at 65° C., and wash occurs at 0.1×SSPE and 1.0% SDS at a temperature of 65° C.

26. The recombinant plant cell of claim 25 wherein said nucleotide sequence is SEQ ID NO:20.

27. The recombinant plant cell of claim 25 wherein said nucleotide sequence is SEQ ID NO:37.

28. The recombinant plant cell of claim 25 wherein said nucleotide sequence is SEQ ID NO:39.

29. The recombinant plant cell of claim 25 wherein said nucleotide sequence is SEQ ID NO:43.

30. The recombinant plant cell of claim 25 wherein said nucleotide sequence is SEQ ID NO:139.

31. The recombinant plant cell of claim 25 wherein said nucleotide sequence is SEQ ID NO:143.

32. A recombinant bacterium comprising an isolated polynucleotide that encodes a pesticidally active protein wherein the full complement of a nucleotide sequence selected from the group consisting or SEQ ID NO:20, SEQ ID NO:37, SEQ ID NO:39, SEQ ID NO:43, SEQ ID NO:139, and SEQ ID NO:143 hybridizes with a polynucleotide molecule that codes for said protein, wherein hybridization occurs in 5×SSPE, 5×Debhardt's solution, 0.5%SDS at 65° C., and wash occurs at 0.1×SSPE and 0.1% SDS at a temperature of 65° C.

33. The recombinant bacterium of claim 32 wherein said nucleotide sequence is SEQ ID NO:20.

34. The recombinant bacterium of claim 32 wherein said nucleotide sequence is SEQ ID NO:37.

35. The recombinant bacterium of claim 32 wherein said nucleotide sequence is SEQ ID NO:39.

36. The recombinant bacterium of claim 32 wherein said nucleotide sequence is SEQ ID NO:43.

37. The recombinant bacterium of claim 32 wherein said nucleotide sequence is SEQ ID NO:139.

38. The recombinant bacterium of claim 32 wherein said nucleotide sequence is SEQ ID NO:143.

39. A recombinant plant cell comprising an isolated polynucleotide that encodes a pesticidally active protein wherein said protein comprises an amino acid sequence selected from the group cosisting of SEQ ID NO:21, SEQ ID NO:38, SEQ ID NO:40, and SEQ ID NO:140.

40. The recombinant plant cell of claim 39 wherein said amino acid sequence is SEQ ID NO:21.

41. The recombinant plant cell of claim 39 wherein said amino acid sequence is SEQ ID NO:38.

42. The recombinant plant cell of claim 39 wherein said amino acid sequence is SEQ ID NO:40.

43. The recombinant plant cell of claim 39 wherein said amino acid sequence is SEQ ID NO:140.

44. A recombinant bacterium comprising an isolated polynucleotide that encodes a pesticidally active protein wherein said protein comprise an amino acid sequence selected from the group consisting of SEQ ID NO:21, SEQ ID NO:38, SEQ ID NO:40, and SEQ ID NO:140.

45. The recombinant bacterium of claim 44 wherein said amino acid sequence is SEQ ID NO:21.

46. The recombinant bacterium of claim 44 wherein said amino acid sequence is SEQ ID NO:38.

47. The recombinant bacterium of claim 44 wherein said amino acid sequence is SEQ ID NO:40.

48. The recombinant bacterium of claim 44 wherein said amino acid sequence is SEQ ID NO:140.

* * * * *

UNITED STATES PATENT AND TRADEMARK OFFICE
CERTIFICATE OF CORRECTION

PATENT NO. : 6,242,669 B1
DATED : June 5, 2001
INVENTOR(S) : Jerald S. Feitelson, H. Ernest Schnepf, Kenneth E. Narva, Brian A. Stockhoff, James Schmeits, David Loewer, Charles Joseph Dullum, Judy Muller-Cohn, Lisa Stamp, George Morrill, Stacey Finstad-Lee It is certified that error appears in the above-identified patent and that said Letters Patent is hereby corrected as shown below:

Column 1,
Line 16, "microscopicallyas" should be -- microscopically as --.
Line 54, "*Z. ang Ent.*" should be -- *Z. ang. Ent.* --.

Column 2,
Line 47, "identifyingtoxin" should be -- identifying toxin --.

Column 4,
Line 41, "PRIMERA" should be -- PRIMER A --.
Line 60, "PS10E 1." should be -- PS10E1. --.

Column 5,
Line 20, "PS 168G1" should be -- PS168G1 --.

Column 8, Table 1,
Line 30, "April 19,1989" should be -- April 19, 1989 --.
Lines 49, 50 and 51, "July 17,1990" should be -- July 17, 1990 --.

Column 9, Table 1,
Line 28, "April 24,1998" should be -- April 24, 1998 --.

Column 12,
Line 22, "culturesas" should be -- cultures as --.
Line 34,."PS 177I8" should be -- PS177I8 --.

Column 15,
Lines 7 and 8, "J Biol." should be -- J. Biol. --.
Line 15, "J Bacteriol." should be -- J. Bacteriol. --.

Column 19,
Line 65, "electrophoresisin" should be -- electrophoresis in --.

Column 20,
Line 52, "solution,0.1%" should be -- solution, 0.1% --.

UNITED STATES PATENT AND TRADEMARK OFFICE
CERTIFICATE OF CORRECTION

PATENT NO. : 6,242,669 B1
DATED : June 5, 2001

INVENTOR(S) : Jerald S. Feitelson, H. Ernest Schnepf, Kenneth E. Narva, Brian A. Stockhoff, James Schmeits, David Loewer, Charles Joseph Dullum, Judy Muller-Cohn, Lisa Stamp, George Morrill, Stacey Finstad-Lee It is certified that error appears in the above-identified patent and that said Letters Patent is hereby corrected as shown below:

Column 21,
Lines 42 and 43, "greaterthan" should be -- greater than --.

Column 22,
Lines 17-18, "nucleotidesto" should be -- nucleotides to --.
Line 46, "67 -endotoxin" should be -- δ-endotoxin --.

Column 23,
Line 25, "$CaCl_2$ Solution (100 ml)" should be -- $CaCl_2$ Solution (100 ml) --
Lines 44-45, "cas amino" should be -- casamino --.

Column 24,
Line 30, "PS29B" should be -- PS92B --.

Column 25,
Line 23, "        The resulting" should be -- The resulting --.
Lines 60-61, "genes of the
SUP-1 family:" should be -- genes of the SUP-1 family: --.

Column 31,
Line 57, "PS 71C2" should be -- PS71C2 --.

Column 32,
Line 25, "Jacksonville, Fla.).
A water" should be -- Jacksonville, Fla.). A water --.
Line 32, "holding Mortality" should be -- holding room. Mortality --.

Column 33, Table 8,
Line 3, "supernatants for" should be -- supernatants screened for --.
Line 11, "PS81A2 (#1) -" should be -- PS81A2 (#1) + --.

Column 34,
Line 45, "(H v.)" should be -- (*H.v.*) --.
Line 47, "Hv.:" should be -- *H.v.* --.
Line 50, "foundto" should be -- found to --.
Line 63, "non-mammalianpests" should be -- non-mammalian pests --.

CERTIFICATE OF CORRECTION

PATENT NO. : 6,242,669 B1
DATED : June 5, 2001

INVENTOR(S) : Jerald S. Feitelson, H. Ernest Schnepf, Kenneth E. Narva, Brian A. Stockhoff, James Schmeits, David Loewer, Charles Joseph Dullum, Judy Muller-Cohn, Lisa Stamp, George Morrill, Stacey Finstad-Lee It is certified that error appears in the above-identified patent and that said Letters Patent is hereby corrected as shown below:

Column 35, Table 9,
Line 24, "DIPTERA" should be -- DIPTERA --.
Line 26, "HOMOPTERA" should be -- HOMOPTERA --.
Line 28, "HEMIPTERA" should be -- HEMIPTERA --.
Line 30, "NEMATODA" should be -- NEMATODA --.
Line 47, "higherplants." should be -- higher plants. --.

Column 167, claim 13,
Line 52, "C. and" should be -- C., and --.

Column 168, claim 32,
Line 44, "consisting or" should be -- consisting of --.
Line 48, "5×Debhardt's solution" should be -- 5×Denhardt's solution --.

Column 168, claim 39,
Line 66, "cosisting" should be -- consisting --.

Column 169, claim 44,
Line 11, "protein comprise" should be -- protein comprises --.

Signed and Sealed this

Twenty-sixth Day of March, 2002

Attest:

JAMES E. ROGAN

*Attesting Officer* *Director of the United States Patent and Trademark Office*

SEQUENCE LISTING (1) GENERAL INFORMATION:

(iii) NUMBER OF SEQUENCES: 144

(2) INFORMATION FOR SEQ ID NO: 1:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 1:

```
GARCCRTGGA AAGCAAATAA TAARAATGC                                   29
```

(2) INFORMATION FOR SEQ ID NO: 2:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 2:

```
AAARTTATCT CCCCAWGCTT CATCTCCATT TTG                              33
```

(2) INFORMATION FOR SEQ ID NO: 3:

(i) SEQUENCE CHARACTERISTICS:
(A) LENGTH: 2375 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: 36a (xi) SEQUENCE DESCRIPTION: SEQ ID NO: 3:

```
ATGAACAAGA ATAATACTAA ATTAAGCACA AGAGCCTTAC CAAGTTTTAT TGATTATTTT    60

AATGGCATTT ATGGATTTGC CACTGGTATC AAAGACATTA TGAACATGAT TTTTAAAACG   120

GATACAGGTG GTGATCTAAC CCTAGACGAA ATTTTAAAGA ATCAGCAGTT ACTAAATGAT   180

ATTTCTGGTA AATTGGATGG GGTGAATGGA AGCTTAAATG ATCTTATCGC ACAGGGAAAC   240

TTAAATACAG AATTATCTAA GGAAATATTA AAAATTGCAA ATGAACAAAA TCAAGTTTTA   300

AATGATGTTA ATAACAAACT CGATGCGATA AATACGATGC TTCGGGTATA TCTACCTAAA   360

ATTACCTCTA TGTTGAGTGA TGTAATGAAA CAAAATTATG CGCTAAGTCT GCAAATAGAA   420

TACTTAAGTA AACAATTGCA AGAGATTTCT GATAAGTTGG ATATTATTAA TGTAAATGTA   480

CTTATTAACT CTACACTTAC TGAAATTACA CCTGCGTATC AAAGGATTAA ATATGTGAAC   540
```

-continued

```
GAAAAATTTG AGGAATTAAC TTTTGCTACA GAAACTAGTT CAAAAGTAAA AAAGGATGGC    600

TCTCCTGCAA ATATTCTTGA TGAGTTAACT GAGTTAACTG AACTAGCGAA AAGTGTAACA    660

AAAAATGATG TGGATGGTTT TGAATTTTAC CTTAATACAT TCCACGATGT AATGGTAGGA    720

AATAATTTAT TCGGGCGTTC AGCTTTAAAA ACTGCATCGG AATTAATTAC TAAAGAAAAT    780

GTGAAAACAA GTGGCAGTGA GGTCGGAAAT GTTTATAACT TCTTAATTGT ATTAACAGCT    840

CTGCAAGCAA AAGCTTTTCT TACTTTAACA ACATGCCGAA AATTATTAGG CTTAGCAGAT    900

ATTGATTATA CTTCTATTAT GAATGAACAT TTAAATAAGG AAAAAGAGGA ATTTAGAGTA    960

AACATCCTCC CTACACTTTC TAATACTTTT TCTAATCCTA ATTATGCAAA AGTTAAAGGA   1020

AGTGATGAAG ATGCAAAGAT GATTGTGGAA GCTAAACCAG GACATGCATT GATTGGGTTT   1080

GAAATTAGTA ATGATTCAAT TACAGTATTA AAAGTATATG AGGCTAAGCT AAAACAAAAT   1140

TATCAAGTCG ATAAGGATTC CTTATCGGAA GTTATTTATG GTGATATGGA TAAATTATTG   1200

TGCCCAGATC AATCTGAACA AATCTATTAT ACAAATAACA TAGTATTTCC AAATGAATAT   1260

GTAATTACTA AAATTGATTT CACTAAAAAA ATGAAAACTT TAAGATATGA GGTAACAGCG   1320

AATTTTTATG ATTCTTCTAC AGGAGAAATT GACTTAAATA AGAAAAAAGT AGAATCAAGT   1380

GAAGCGGAGT ATAAAACGTT AAGTGCTAAT GATGATGGGG TGTATATGCC GTTAGGTGTC   1440

ATCAGTGAAA CATTTTTGAC TCCGATTAAT GGGTTTGGCC TCCAAGCTGA TGAAAATTCA   1500

AGATTAATTA CTTTAACATG TAAATCATAT TTAAGAGAAC TACTGCTAGC AACAGACTTA   1560

AGCAATAAAG AAACTAAATT GATCGTCCCG CCAAGTGGTT TTATTAGCAA TATTGTAGAG   1620

AACGGGTCCA TAGAAGAGGA CAATTTAGAG CCGTGGAAAG CAAATAATAA GAATGCGTAT   1680

GTAGATCATA CAGGCGGAGT GAATGGAACT AAAGCTTTAT ATGTTCATAA GGACGGAGGA   1740

ATTTCACAAT TTATTGGAGA TAATTTAAAA CCGAAAACTG AGTATGTAAT CCAATATACT   1800

GTTAAAGGAA AACCTTCTAT TCATTTAATA GATGAAAATA CTGGATATAT TCATTATGAA   1860

GATACAAATA ATAATTTAGA AGATTATCAA ACTATTAATA AACGTTTTAC TACAGGAACT   1920

GATTTAAAGG GAGTGTATTT AATTTTAAAA AGTCAAAATG GAGATGAAGC TTGGGGAGAT   1980

AACTTTATTA TTTTGGAAAT TAGTCCTTCT GAAAAGTTAT TAAGTCCAGA ATTAATTAAT   2040

ACAAATAATT GGACGAGTAC GGGATCAACT AATATTAGCG GTAATACACT CACTCTTTAT   2100

CAGGGAGGAC GAGGGATTCT AAAACAAAAC CTTCAATTAG ATAGTTTTTC AACTTATAGA   2160

GTGTATTTTT CTGTGTCCGG AGATGCTAAT GTAAGGATTA GAAATTCTAG GGAAGTGTTA   2220

TTTGAAAAAA GATATATGAG CGGTGCTAAA GATGTTTCTG AAATGTTCAC TACAAAATTT   2280

GAGAAAGATA ACTTTTATAT AGAGCTTTCT CAAGGGAATA ATTTATATGG TGGTCCTATT   2340

GTACATTTTT ACGATGTCTC TATTAAGTAA CCCAA                              2375
```

(2) INFORMATION FOR SEQ ID NO: 4:

(i) SEQUENCE CHARACTERISTICS:
(A) LENGTH: 790 amino acids
(B) TYPE: amino acid
(C) STRANDEDNESS: single
(D) TOPOLOGY: linear (ii) MOLECULE TYPE: protein (vi) ORIGINAL SOURCE:
(C) INDIVIDUAL ISOLATE: 36a (xi) SEQUENCE DESCRIPTION: SEQ ID NO: 4:

-continued

```
Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asn Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
```

-continued

```
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
    450                 455                 460

Lys Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
    530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Asn Leu Lys Pro Lys
            580                 585                 590

Thr Glu Tyr Val Ile Gln Tyr Thr Val Lys Gly Lys Pro Ser Ile His
        595                 600                 605

Leu Ile Asp Glu Asn Thr Gly Tyr Ile His Tyr Glu Asp Thr Asn Asn
    610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
            660                 665                 670

Leu Leu Ser Pro Glu Leu Ile Asn Thr Asn Asn Trp Thr Ser Thr Gly
        675                 680                 685

Ser Thr Asn Ile Ser Gly Asn Thr Leu Thr Leu Tyr Gln Gly Gly Arg
    690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
            740                 745                 750

Ser Glu Met Phe Thr Thr Lys Phe Glu Lys Asp Asn Phe Tyr Ile Glu
        755                 760                 765

Leu Ser Gln Gly Asn Asn Leu Tyr Gly Gly Pro Ile Val His Phe Tyr
    770                 775                 780

Asp Val Ser Ile Lys Pro
785                 790
```

(2) INFORMATION FOR SEQ ID NO: 5:

(i) SEQUENCE CHARACTERISTICS:
(A) LENGTH: 2370 base pairs
(B) TYPE: nucleic acid
(C) STRANDEDNESS: single
(D) TOPOLOGY: linear -continued (ii) MOLECULE TYPE: DNA (genomic)

(vi) ORIGINAL SOURCE:
(C) INDIVIDUAL ISOLATE: 81Fd (xi) SEQUENCE DESCRIPTION: SEQ ID NO: 5:

```
ATGAACAAGA ATAATACTAA ATTAAGCACA AGAGCCTTAC CAAGTTTTAT TGATTATTTT     60

AATGGCATTT ATGGATTTGC CACTGGTATC AAAGACATTA TGAACATGAT TTTTAAAACG    120

GATACAGGTG GTGATCTAAC CCTAGACGAA ATTTTAAAGA ATCAGCAGTT ACTAAATGAT    180

ATTTCTGGTA AATTGGATGG GGTGAATGGA AGCTTAAATG ATCTTATCGC ACAGGGAAAC    240

TTAAATACAG AATTATCTAA AGAAATATTA AAAATTGCAA ATGAACAAAA TCAAGTTTTA    300

AATGATGTTG ATAACAAACT CGATGCGATA AATACGATGC TTCGGGTATA TCTACCTAAA    360

ATTACCTCTA TGTTGAGTGA TGTAATGAAA CAAAATTATG CGCTAAGTCT GCAAATAGAA    420

TACTTAAGTA AACAATTGCA AGAGATTTCT GATAAGTTGG ATATTATTAA TGTAAATGTA    480

CTTATTAACT CTACACTTAC TGAAATTACA CCTGCGTATC AAAGGATTAA ATATGTGAAC    540

GAAAAATTTG AGGAATTAAC TTTTGCTACA GAAACTAGTT CAAAAGTAAA AAAGGATGGC    600

TCTCCTGCAG ATATTCTTGA TGAGTTAACT GAGTTAACTG AACTAGCGAA AAGTGTAACA    660

AAAAATGATG TGGATGGTTT TGAATTTTAC CTTAATACAT TCCACGATGT AATGGTAGGA    720

AATAATTTAT TCGGGCGTTC AGCTTTAAAA ACTGCATCGG AATTAATTAC TAAAGAAAAT    780

GTGAAAACAA GTGGCAGTGA GGTCGGAAAT GTTTATAACT TCTTAATTGT ATTAACAGCT    840

CTGCAAGCAA AAGCTTTTCT TACTTTAACA ACATGCCGAA AATTATTAGG CTTAGCAGAT    900

ATTGATTATA CTTCTATTAT GAATGAACAT TTAAATAAGG AAAAAGAGGA ATTTAGAGTA    960

AACATCCTCC CTACACTTTC TAATACTTTT TCTAATCCTA ATTATGCAAA AGTTAAAGGA   1020

AGTGATGAAG ATGCAAAGAT GATTGTGGAA GCTAAACCAG GACATGCATT GGTTGGGTTT   1080

GAAATTAGTA ATGATTCAAT TACAGTATTA AAAGTATATG AGGCTAAGCT AAAACAAAAT   1140

TATCAAGTTG ATAAGGATTC CTTATCGGAA GTTATTTATG GTGATATGGA TAAATTATTG   1200

TGCCCAGATC AATCTGAACA AATCTATTAT ACAAATAACA TAGTATTTCC AAATGAATAT   1260

GTAATTACTA AAATTGATTT TACTAAAAAA ATGAAAACTT TAAGATATGA GGTAACAGCG   1320

AATTTTTATG ATTCTTCTAC AGGAGAAATT GACTTAAATA AGAAAAAAGT AGAATCAAGT   1380

GAAGCGGAGT ATAGAACGTT AAGTGCTAAT GATGATGGAG TGTATATGCC GTTAGGTGTC   1440

ATCAGTGAAA CATTTTTGAC TCCGATTAAT GGGTTTGGCC TCCAAGCTGA TGAAAATTCA   1500

AGATTAATTA CTTTAACATG TAAATCATAT TTAAGAGAAC TACTGCTAGC AACAGACTTA   1560

AGCAATAAAG AAACTAAATT GATCGTCCCG CCCAGTGGTT TTATTAAAAA TATTGTAGAG   1620

AACGGGTCCA TAGAAGAGGA CAATTTAGAG CCGTGGAAAG CAAATAATAA GAATGAGTAT   1680

GTAGATCATA CAGGCGGAGT GAATGGRACT AAAGCTTTAT ATGTTCATAA GGACGGAGGA   1740

ATTTCACAAT TTATTGGAGA TAAGTTAAAA CCGAAAACTG AGTATGTAAT CCAATATACT   1800

GTTAAAGGAA AACCTTCTAT TCATTTAAAA GATGAAAATA CTGGATATAT TCATTATGAA   1860

GATACAAATA ATAATTTAGA AGATTATCAA ACTATTACTA AACGTTTTAC TACAGGAACT   1920

GATTTAAAGG GAGTGTATTT AATTTTAAAA AGTCAAAATG GAGATGAAGC TTGGGGAGAT   1980

AACTTTATTA TTTTGGAAAT TAGTCCTTCT GAAAAGTTAT TAAGTCCAGA ATTAATTAAT   2040

ACAAATAATT GGACGAGTAC GGGATCAACT AATATTAGCG GTAATACACT CACTCTTTAT   2100

CAGGGAGGAC GAGGAATTCT AAAACAAAAC CTTCAATTAG ATAGTTTTTC AACTTATAGA   2160
```

-continued

```
GTGTATTTTT CTGTGTCCGG AGATGCTAAT GTAAGGATTA GAAATTCTAG GGAAGTGTTA   2220

TTTGAAAAAA GATATATGAG CGGTGCTAAA GATGTTTCTG AAATTTTCAC TACAAAATTT   2280

GGGAAAGATA ACTTTTATAT AGAGCTTTCT CAAGGGAATA ATTTAAATGG TGGCCCTATT   2340

GTACAGTTTC CCGATGTCTC TATTAAGTAA                                    2370
```

(2) INFORMATION FOR SEQ ID NO: 6:

(i) SEQUENCE CHARACTERISTICS:
(A) LENGTH: 789 amino acids
(B) TYPE: amino acid
(C) STRANDEDNESS: single
(D) TOPOLOGY: linear (ii) MOLECULE TYPE: protein (vi) ORIGINAL SOURCE:
(C) INDIVIDUAL ISOLATE: 81Fd (xi) SEQUENCE DESCRIPTION: SEQ ID NO: 6:

```
Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asp Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285
```

-continued

```
Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Val Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Lys Asn Ile Val Glu Asn Gly Ser Ile
    530                 535                 540

Glu Glu Asp Asn Leu Glu Pro Trp Lys Ala Asn Asn Lys Asn Glu Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
    610                 615                 620

Asn Leu Glu Asp Tyr Gln Thr Ile Thr Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
            660                 665                 670

Leu Leu Ser Pro Glu Leu Ile Asn Thr Asn Asn Trp Thr Ser Thr Gly
        675                 680                 685

Ser Thr Asn Ile Ser Gly Asn Thr Leu Thr Leu Tyr Gln Gly Gly Arg
    690                 695                 700

Gly Ile Leu Lys Gln Asn Leu Gln Leu Asp Ser Phe Ser Thr Tyr Arg
```

-continued

```
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
            740                 745                 750

Ser Glu Ile Phe Thr Thr Lys Phe Gly Lys Asp Asn Phe Tyr Ile Glu
        755                 760                 765

Leu Ser Gln Gly Asn Asn Leu Asn Gly Gly Pro Ile Val Gln Phe Pro
    770                 775                 780

Asp Val Ser Ile Lys
785
```

(2) INFORMATION FOR SEQ ID NO: 7:

(i) SEQUENCE CHARACTERISTICS:
(A) LENGTH: 2375 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: Jav90

(xi) SEQUENCE DESCRIPTION: SEQ ID NO: 7:

```
ATGAACAAGA ATAATACTAA ATTAAGCACA AGAGCCTTAC CAAGTTTTAT TGATTATTTT     60

AATGGCATTT ATGGATTTGC CACTGGTATC AAAGACATTA TGAACATGAT TTTTAAAACG    120

GATACAGGTG GTGATCTAAC CCTAGACGAA ATTTTAAAGA ATCAGCAGTT ACTAAATGAT    180

ATTTCTGGTA AATTGGATGG GGTGAATGGA AGCTTAAATG ATCTTATCGC ACAGGGAAAC    240

TTAAATACAG AATTATCTAA GGAAATATTA AAAATTGCAA ATGAACAAAA TCAAGTTTTA    300

AATGATGTTA ATAACAAACT CGATGCGATA AATACGATGC TTCGGGTATA TCTACCTAAA    360

ATTACCTCTA TGTTGAGTGA TGTAATGAAA CAAAATTATG CGCTAAGTCT GCAAATAGAA    420

TACTTAAGTA AACAATTGCA AGAGATTTCT GATAAGTTGG ATATTATTAA TGTAAATGTA    480

CTTATTAACT CTACACTTAC TGAAATTACA CCTGCGTATC AAAGGATTAA ATATGTGAAC    540

GAAAAATTTG AGGAATTAAC TTTTGCTACA GAAACTAGTT CAAAAGTAAA AAAGGATGGC    600

TCTCCTGCAG ATATTCTTGA TGAGTTAACT GAGTTAACTG AACTAGCGAA AAGTGTAACA    660

AAAAATGATG TGGATGGTTT TGAATTTTAC CTTAATACAT TCCACGATGT AATGGTAGGA    720

AATAATTTAT TCGGGCGTTC AGCTTTAAAA ACTGCATCGG AATTAATTAC TAAAGAAAAT    780

GTGAAAACAA GTGGCAGTGA GGTCGGAAAT GTTTATAACT TCTTAATTGT ATTAACAGCT    840

CTGCAAGCAA AAGCTTTTCT TACTTTAACA ACATGCCGAA AATTATTAGG CTTAGCAGAT    900

ATTGATTATA CTTCTATTAT GAATGAACAT TTAAATAAGG AAAAAGAGGA ATTTAGAGTA    960

AACATCCTCC CTACACTTTC TAATACTTTT TCTAATCCTA ATTATGCAAA AGTTAAAGGA   1020

AGTGATGAAG ATGCAAAGAT GATTGTGGAA GCTAAACCAG GACATGCATT GATTGGGTTT   1080

GAAATTAGTA ATGATTCAAT TACAGTATTA AAAGTATATG AGGCTAAGCT AAAACAAAAT   1140

TATCAAGTCG ATAAGGATTC CTTATCGGAA GTTATTTATG GTGATATGGA TAAATTATTG   1200

TGCCCAGATC AATCTGAACA AATCTATTAT ACAAATAACA TAGTATTTCC AAATGAATAT   1260

GTAATTACTA AAATTGATTT CACTAAAAAA ATGAAAACTT TAAGATATGA GGTAACAGCG   1320

AATTTTTATG ATTCTTCTAC AGGAGAAATT GACTTAAATA AGAAAAAAGT AGAATCAAGT   1380
```

-continued

```
GAAGCGGAGT ATAGAACGTT AAGTGCTAAT GATGATGGGG TGTATATGCC GTTAGGTGTC   1440

ATCAGTGAAA CATTTTTGAC TCCGATTAAT GGGTTTGGCC TCCAAGCTGA TGAAAATTCA   1500

AGATTAATTA CTTTAACATG TAAATCATAT TTAAGAGAAC TACTGCTAGC AACAGACTTA   1560

AGCAATAAAG AAACTAAATT GATYGTCCCG CCAAGTGGTT TTATTAGCAA TATTGTAGAG   1620

AACGGGTCCA TAGAAGAGGA CAATTTAGAG CCGTGGAAAG CAAATAATAA GAATGCGTAT   1680

GTAGATCATA CAGGCGGAGT GAATGGAACT AAAGCTTTAT ATGTTCATAA GGACGGAGGA   1740

ATTTCACAAT TTATTGGAGA TAAGTTAAAA CCGAAAACTG AGTATGTAAT CCAATATACT   1800

GTTAAAGGAA AACCTTCTAT TCATTTAAAA GATGAAAATA CTGGATATAT TCATTATGAA   1860

GATACAAATA ATAATTTAGA AGATTATCAA ACTATTAATA AACGTTTTAC TACAGGAACT   1920

GATTTAAAGG GAGTGTATTT AATTTTAAAA AGTCAAAATG GAGATGAAGC TTGGGGAGAT   1980

AACTTTATTA TTTTGGAAAT TAGTCCTTCT GAAAAGTTAT TAAGTCCAGA ATTAATTAAT   2040

ACAAATAATT GGACGAGTAC GGGATCAACT AATATTAGCG GTAATACACT CACTCTTTAT   2100

CAGGGAGGAC GAGGGATTCT AAAACAAAAC CTTCAATTAG ATAGTTTTTC AACTTATAGA   2160

GTGTATTTTT CTGTGTCCGG AGATGCTAAT GTAAGGATTA GAAATTCTAG GGAAGTGTTA   2220

TTTGAAAAAA GATATATGAG CGGTGCTAAA GATGTTTCTG AAATGTTCAC TACAAAATTT   2280

GAGAAAGATA ACTTTTATAT AGAGCTTTCT CAAGGGAATA ATTTATATGG TGGTCCTATT   2340

GTACATTTTT ACGATGTCTC TATTAAGTAA CCCAA                              2375
```

(2) INFORMATION FOR SEQ ID NO: 8:

(i) SEQUENCE CHARACTERISTICS:
(A) LENGTH: 790 amino acids
(B) TYPE: amino acid
(C) STRANDEDNESS: single
(D) TOPOLOGY: linear (ii) MOLECULE TYPE: protein (vi) ORIGINAL SOURCE:
(C) INDIVIDUAL ISOLATE: Jav90

(xi) SEQUENCE DESCRIPTION: SEQ ID NO: 8:

```
Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160
```

-continued

```
Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
    530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575
```

-continued

```
Lys Asp Gly Gly Ile Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
    610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
            660                 665                 670

Leu Leu Ser Pro Glu Leu Ile Asn Thr Asn Asn Trp Thr Ser Thr Gly
        675                 680                 685

Ser Thr Asn Ile Ser Gly Asn Thr Leu Thr Leu Tyr Gln Gly Gly Arg
    690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
            740                 745                 750

Ser Glu Met Phe Thr Thr Lys Phe Glu Lys Asp Asn Phe Tyr Ile Glu
        755                 760                 765

Leu Ser Gln Gly Asn Asn Leu Tyr Gly Gly Pro Ile Val His Phe Tyr
    770                 775                 780

Asp Val Ser Ile Lys Pro
785                 790
```

(2) INFORMATION FOR SEQ ID NO: 9:

(i) SEQUENCE CHARACTERISTICS:
(A) LENGTH: 47 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 9:

```
GCTCTAGAAG GAGGTAACTT ATGAACAAGA ATAATACTAA ATTAAGC                   47
```

(2) INFORMATION FOR SEQ ID NO: 10:

(i) SEQUENCE CHARACTERISTICS:
(A) LENGTH: 2035 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: 158C2-ptl (xi) SEQUENCE DESCRIPTION: SEQ ID NO: 10:

```
ATGAACAAGA ATAATACTAA ATTAAGCGCA AGGGCCTACC GAGTTTTATT GATTATTTTA     60

ATGGCATTTA TGGATTTGCC ACTGGTATCA AAGACATTAT GAATATGATT TTTAAAACGG    120

ATACAGGTGG TAATCTAACC TTAGACGAAA TCCTAAAGAA TCAGCAGTTA CTAAATGAGA    180
```

-continued

```
TTTCTGGTAA ATTGGATGGG GTAAATGGGA GCTTAAATGA TCTTATCGCA CAGGGAAACT    240

TAAATACAGA ATTAGCTAAG CAAATCTTAA AAGTTGCAAA TGAACAAAAT CAAGTTTTAA    300

ATGATGTTAA TAACAAACTA GACTGCGATA AATACGATGC TTAAAATATA TCTACCTAAA    360

ATTCACATCT ATGTTAAGTG ATGTACTGAA GCCAAAATTA TGTGCTTAAG TCTTGCAAAT    420

TGGAATTACC TTTAAGTAAC ATCTGCACCT TGGCAAGAAA TCTCCGACAA GCTAGATATT    480

ATTAACGTAA ATGTGCTTAT TAACTCTACG CTTACTGAAA TTACACCTGC GTATCAACGA    540

ATTAAATATG TGAATGAAAA ATTTGACGAT TTAACTTTTG CTACAGAAAA CACTTTAAAA    600

GTAAAAAAGG ATAGCTCTCC TGCTGATATT CTTGACGAGT TAACTGAATT AACTGAACTA    660

GCGAAAAGTG TTACAAAAAA TGACGTGGAT GGTTTTGAAT TTTACCTTAA TACATTCCAT    720

GATGTAATGG TGGGAAATAA TTTATTCGGT CGTTCAGCTT TAAAAACTGC TTCGGAATTA    780

ATTGCTAAAG AAAATGTGAA AACAAGTGGC AGTGAAGTAG GAAATGTTTA TAATTTCTTA    840

ATTGTATTAA CAGCTCTACA AGCAAAAGCT TTTCTTACTT TAACAACATG CCGAAAATTA    900

TTAGGCTTAG CAGATATTGA TTATACTTCT ATCATGAATG AGCATTTAAA TAAGGAAAAA    960

GAGGAATTTA GAGTAAACAT CCTTCCCACA CTTTCTAATA CCTTTTCTAA TCCTAATTAT   1020

GCAAAAGCTA AGGGAAGTAA TGAAGATACA AAGATGATTG TGGAAGCTAA ACCAGGATAT   1080

GTTTTGGTTG GATTTGAAAT GAGCAATAAT TCAATTACAG TATTAAAAGC ATATCAAGCT   1140

AAGCTAAAAA AAGATTATCA AATTGATAAG GATTCGTTAT CAGAAATAAT ATATAGTACG   1200

TGATACGGAT AAATTATTAT GTCCGGATCA ATCTGAACAA TATATTATAC AAAGAACATA   1260

GCATTTCCAA ATGAATATGT TATTACTAAA ATTGCTTTTA CTAAAAAAAT GAACAGTTTA   1320

AGGTATGAGG CGACAGCGAA TTTTTATGAT TCTTCTACAG GGGATATTGA TCTAAATAAG   1380

ACAAAAGTAG AATCAAGTGA AGCGGAGTAT AGTATGCTAA AAGCTAGTGA TGATGAAGTT   1440

TACATGCCGC TAGGTCTTAT CAGTGAAACA TTTTTAAATC CAATTAATGG ATTTAGGCTT   1500

GCAGTCGATG AAAATTCCAG ACTAGTAACT TTAACATGTA GATCATATTT AAGAGAGACA   1560

TTGTTAGCGA CAGATTTAAA TAATAAAGAA ACTAAATTGA TTGTCCCACC TAATGTTTTT   1620

ATTAGCAATA TTGTAGAGAA TGGAAATATA GAAATGGACA CCTTAGAACC ATGGAAGGCA   1680

AATAATGAGA ATGCGAATGT AGATTATTCA GGCGGAGTGA ATGGAACTAG AGCTTTATAT   1740

GTTCATAAGG ATGGTGAATT CTCACATTTT ATTGGAGACA AGTTGAAATC TAAAACAGAA   1800

TACTTGATTC GATATATTGT AAAAGGAAAA GCTTCTATTT TTTTAAAAGA TGAAAGAAAT   1860

GAAAATTACA TTTACGAGGA TACAAATAAT AATTTAGAAG ATTATCAAAC TATTACTAAA   1920

CGTTTTACTA CAGGAACTGA TTCGACAGGA TTTTATTTAT TTTTTACTAC TCAAGATGGA   1980

AATGAAGCTT GGGGAGACAC TTTTTTTCTC TAGAAAGAGG TAACTTATGA ACAAG        2035
```

(2) INFORMATION FOR SEQ ID NO: 11:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 11:

```
CATCCTCCCT ACACTTTCTA A                                                21
```

(2) INFORMATION FOR SEQ ID NO: 12:

(i) SEQUENCE CHARACTERISTICS:
(A) LENGTH: 950 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: 49C3-ptl (xi) SEQUENCE DESCRIPTION: SEQ ID NO: 12:

```
AAACTAGAGG GAGTGATAAG GATGCGAAAA TCATTATGGA AGCTAAACCT GGATATGCTT     60
TAGTTGGATT TGAAATAAGT AAGGATTCAA TTGCAGTATT AAAAGTTTAT CAGGCAAAGC    120
TAAAACACAA CTATCAAATT GATAAGGATT CGTTATCAGA AATTGTTTAT GGTGATATAG    180
ATAAATTATT ATGTCCGGAT CAATCTGAAC AAATGTATTA TACAAATAAA ATAGCATTTC    240
CAAATGAATA TGTTATCACT AAAATTGCTT TTACTAAAAA ACTGAACAGT TTAAGATATG    300
AGGTCACAGC GAATTTTTAT GACTCTTCTA CAGGAGATAT TGATCTAAAT AAGAAAAAAA    360
TAGAATCAAG TGAAGCGGAG TTTAGTATGC TAAATGCTAA TAATGATGGT GTTTATATGC    420
CGATAGGTAC TATAAGTGAA ACATTTTTGA CTCCAATTAA TGGATTTGGC CTCGTAGTCG    480
ATGAAAATTC AAGACTAGTA ACTTTGACAT GTAAATCATA TTTAAGAGAG ACATTGTTAG    540
CAACAGACTT AAGTAATAAA GAAACTAAAC TGATTGTCCC ACCTAATGGT TTTATTAGCA    600
ATATTGTAGA AAATGGGAAC TTAGAGGGAG AAAACTTAGA GCCGTGGGAA AGCAAATAAC    660
AAAAATGCGT ATGTAGATCA TACCGGAGGT GTAAATGGAA CTAAAGTTTT ATATGTTCAT    720
GAGGATGGTG AGTTCTCACA ATTTATTGGG GATAAATTGA AATTGAAAAC AGAATATGTA    780
ATTCCATATA TTGTAAAGGG GAAAGCTGCT ATTTATTTAA AAGATGAAAA AAATGGGGAT    840
TACATATCAT GAAGAAACAT CATAATGCAA TTGAAGATTT TTCCAGCTGT AACTTCAATA    900
ATGATTTTCG CATCCTTATC ATCCCTCTAG CTTTTTCATA ATAGGATAGA               950
```

(2) INFORMATION FOR SEQ ID NO: 13:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 13:

```
AAATTATGCG CTAAGTCTGC                                                 20
```

(2) INFORMATION FOR SEQ ID NO: 14:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 14:

```
TTGATCCGGA CATAATAAT                                                  19
```

(2) INFORMATION FOR SEQ ID NO: 15:

-continued (i) SEQUENCE CHARACTERISTICS:
(A) LENGTH: 176 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: 49C8-ptl (xi) SEQUENCE DESCRIPTION: SEQ ID NO: 15:

```
GTAAATTATG CGCTAAGTCT GCACCTTTTT TCACTGTTAC TAAACATCAC TTTTCCTATA     60

TCCCCTTAGC TCTTATGGAT TATTGAGCAA ACTTATCTTG TTAATTACTA CTCCCCATCA    120

TATGCTAAAC AAAAACCAAA CAAACATTAT CTATTATATG TCCGGATCAA AATGTA        176
```

(2) INFORMATION FOR SEQ ID NO: 16:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 16:

```
GGRTTAMTTG GRTAYTATTT                                                 20
```

(2) INFORMATION FOR SEQ ID NO: 17:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 17:

```
ATATCKWAYA TTKGCATTTA                                                 20
```

(2) INFORMATION FOR SEQ ID NO: 18:

(i) SEQUENCE CHARACTERISTICS:
(A) LENGTH: 1076 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: 10E1

(xi) SEQUENCE DESCRIPTION: SEQ ID NO: 18:

```
TGGGATTACT TGGATATTAT TTCCAGGATC AAAAGTTTCA GCAACTTGCT TTGATGGCAC     60

ATAGACAAGC TTCTGATTTG GAAATCCCGA AAGATGACGT GAAACAGTTA CTATCCAAGG    120

AGCAGCAACA CATTCAATCT GTTAGATGGC TTGGCTATAT TCAGCCACCT CAAACAGGAG    180

ACTATGTATT GTCAACCTCA TCCGACCAAC AGGTCGTGAT TGAACTCGAT GGAAAAACCA    240

TTGTCAATCA AACTTCTATG ACAGAACCGA TTCAACTCGA AAAAGATAAG CTCTATAAAA    300

TTAGAATTGA ATATGTCCCA GAAGATACAA AAGAACAAGA GAACCTCCTT GACTTTCAGC    360

TCAACTGGTC GATTTCAGGA TCAGAGATAG AACCAATTCC GGAGAATGCT TTCCATTTAC    420
```

-continued

```
CAAATTTTTC TCGTAAACAA GATCAAGAGA AAATCATCCC TGAAACCAGT TTGTTTCAGG    480

AACAAGGAGA TGAGAAAAAA GTATCTCGCA GTAAGAGATC TTTAGCTACA AATCCTATCC    540

GTGATACAGA TGATGATAGT ATTTATGATG AATGGGAAAC GGAAGGATAC ACGATACGGG    600

AACAAATAGC AGTGAAATGG GACGATTCTA TGAAGGATAG AGGTTATACC AAATATGTGT    660

CAAACCCCTA TAAGTCTCAT ACAGTAGGAG ATCCATACAC AGATTGGGAA AAAGCGGCTG    720

GCCGTATCGA TAACGGTGTC AAAGCAGAAG CCAGAAATCC TTTAGTCGCG GCCTATCCAA    780

CTGTTGGTGT ACATATGGAA AGATTAATTG TCTCCGAAAA ACAAAATATA TCAACAGGGC    840

TTGGAAAAAC TGTATCTGCG TCTATGTCCG CAAGCAATAC CGCAGCGATT ACGGCAGGTA    900

TTGATGCAAC AGCCGGTGCC TCTTTACTCG GGCCATCTGG AAGTGTCACG GCTCATTTTT    960

CTTATACAGG ATCTAGTACA TCCACCGTTG AAGATAGCTC CAGCCGGAAT TGGAGTCAAG   1020

ACCTTGGGAT CGATACGGGA CAATCTGCAT ATTTAAATGC CAAATGTACG ATATAA       1076
```

(2) INFORMATION FOR SEQ ID NO: 19:

(i) SEQUENCE CHARACTERISTICS:
(A) LENGTH: 357 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: 10E1

(xi) SEQUENCE DESCRIPTION: SEQ ID NO: 19:

```
Gly Leu Leu Gly Tyr Tyr Phe Gln Asp Gln Lys Phe Gln Gln Leu Ala
1               5                   10                  15

Leu Met Ala His Arg Gln Ala Ser Asp Leu Glu Ile Pro Lys Asp Asp
            20                  25                  30

Val Lys Gln Leu Leu Ser Lys Glu Gln Gln His Ile Gln Ser Val Arg
        35                  40                  45

Trp Leu Gly Tyr Ile Gln Pro Pro Gln Thr Gly Asp Tyr Val Leu Ser
    50                  55                  60

Thr Ser Ser Asp Gln Gln Val Val Ile Glu Leu Asp Gly Lys Thr Ile
65                  70                  75                  80

Val Asn Gln Thr Ser Met Thr Glu Pro Ile Gln Leu Glu Lys Asp Lys
                85                  90                  95

Leu Tyr Lys Ile Arg Ile Glu Tyr Val Pro Glu Asp Thr Lys Glu Gln
            100                 105                 110

Glu Asn Leu Leu Asp Phe Gln Leu Asn Trp Ser Ile Ser Gly Ser Glu
        115                 120                 125

Ile Glu Pro Ile Pro Glu Asn Ala Phe His Leu Pro Asn Phe Ser Arg
    130                 135                 140

Lys Gln Asp Gln Glu Lys Ile Ile Pro Glu Thr Ser Leu Phe Gln Glu
145                 150                 155                 160

Gln Gly Asp Glu Lys Lys Val Ser Arg Ser Lys Arg Ser Leu Ala Thr
                165                 170                 175

Asn Pro Ile Arg Asp Thr Asp Asp Asp Ser Ile Tyr Asp Glu Trp Glu
            180                 185                 190

Thr Glu Gly Tyr Thr Ile Arg Glu Gln Ile Ala Val Lys Trp Asp Asp
        195                 200                 205

Ser Met Lys Asp Arg Gly Tyr Thr Lys Tyr Val Ser Asn Pro Tyr Lys
    210                 215                 220
```

-continued

```
Ser His Thr Val Gly Asp Pro Tyr Thr Asp Trp Glu Lys Ala Ala Gly
225                 230                 235                 240

Arg Ile Asp Asn Gly Val Lys Ala Glu Ala Arg Asn Pro Leu Val Ala
                245                 250                 255

Ala Tyr Pro Thr Val Gly Val His Met Glu Arg Leu Ile Val Ser Glu
            260                 265                 270

Lys Gln Asn Ile Ser Thr Gly Leu Gly Lys Thr Val Ser Ala Ser Met
        275                 280                 285

Ser Ala Ser Asn Thr Ala Ala Ile Thr Ala Gly Ile Asp Ala Thr Ala
    290                 295                 300

Gly Ala Ser Leu Leu Gly Pro Ser Gly Ser Val Thr Ala His Phe Ser
305                 310                 315                 320

Tyr Thr Gly Ser Ser Thr Ser Thr Val Glu Asp Ser Ser Ser Arg Asn
                325                 330                 335

Trp Ser Gln Asp Leu Gly Ile Asp Thr Gly Gln Ser Ala Tyr Leu Asn
            340                 345                 350

Ala Lys Cys Thr Ile
        355
```

(2) INFORMATION FOR SEQ ID NO: 20:

(i) SEQUENCE CHARACTERISTICS:
(A) LENGTH: 1045 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: 31J2

(xi) SEQUENCE DESCRIPTION: SEQ ID NO: 20:

```
TGGGTTACTT GGGTATTATT TTAAAGGAAA AGATTTTAAT AATCTTACTA TATTTGCTCC     60

AACACGTGAG AATACTCTTA TTTATGATTT AGAAACAGCG AATTCTTTAT TAGATAAGCA    120

ACAACAAACC TATCAATCTA TTCGTTGGAT CGGTTTAATA AAAAGCAAAA AAGCTGGAGA    180

TTTTACCTTT CAATTATCGG ATGATGAGCA TGCTATTATA GAAATCGATG GGAAAGTTAT    240

TTCGCAAAAA GGCCAAAAGA AACAAGTTGT TCATTTAGAA AAAGATAAAT TAGTTCCCAT    300

CAAAATTGAA TATCAATCTG ATAAAGCGTT AAACCCAGAT AGTCAAATGT TTAAAGAATT    360

GAAATTATTT AAAATAAATA GTCAAAAACA ATCTCAGCAA GTGCAACAAG ACGAATTGAG    420

AAATCCTGAA TTTGGTAAAG AAAAAACTCA AACATATTTA AAGAAAGCAT CGAAAAGCAG    480

CTTGTTTAGC AATAAAAGTA AACGAGATAT AGATGAAGAT ATAGATGAGG ATACAGATAC    540

AGATGGAGAT GCCATTCCTG ATGTATGGGA AGAAAATGGG TATACCATCA AAGGAAGAGT    600

AGCTGTTAAA TGGGACGAAG GATTAGCTGA TAAGGGATAT AAAAAGTTTG TTTCCAATCC    660

TTTTAGACAG CACACTGCTG GTGACCCCTA TAGTGACTAT GAAAAGGCAT CAAAAGATTT    720

GGATTTATCT AATGCAAAAG AAACATTTAA TCCATTGGTG GCTGCTTTTC CAAGTGTCAA    780

TGTTAGCTTG GAAAATGTCA CCATATCAAA AGATGAAAAT AAAACTGCTG AAATTGCGTC    840

TACTTCATCG AATAATTGGT CCTATACAAA TACAGAGGGG GCATCTATTG AAGCTGGAAT    900

TGGACCAGAA GGTTTGTTGT CTTTTGGAGT AAGTGCCAAT TATCAACATT CTGAAACAGT    960

GGCCAAAGAG TGGGGTACAA CTAAGGGAGA CGCAACACAA TATAATACAG CTTCAGCAGG   1020

ATATCTAAAT GCCAATGTAC GATAT                                         1045
```

(2) INFORMATION FOR SEQ ID NO: 21:

(i) SEQUENCE CHARACTERISTICS:
(A) LENGTH: 348 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: 31J2

(xi) SEQUENCE DESCRIPTION: SEQ ID NO: 21:

```
Gly Leu Leu Gly Tyr Tyr Phe Lys Gly Lys Asp Phe Asn Asn Leu Thr
1               5                   10                  15

Ile Phe Ala Pro Thr Arg Glu Asn Thr Leu Ile Tyr Asp Leu Glu Thr
            20                  25                  30

Ala Asn Ser Leu Leu Asp Lys Gln Gln Gln Thr Tyr Gln Ser Ile Arg
        35                  40                  45

Trp Ile Gly Leu Ile Lys Ser Lys Lys Ala Gly Asp Phe Thr Phe Gln
    50                  55                  60

Leu Ser Asp Asp Glu His Ala Ile Ile Glu Ile Asp Gly Lys Val Ile
65                  70                  75                  80

Ser Gln Lys Gly Gln Lys Lys Gln Val Val His Leu Glu Lys Asp Lys
                85                  90                  95

Leu Val Pro Ile Lys Ile Glu Tyr Gln Ser Asp Lys Ala Leu Asn Pro
            100                 105                 110

Asp Ser Gln Met Phe Lys Glu Leu Lys Leu Phe Lys Ile Asn Ser Gln
        115                 120                 125

Lys Gln Ser Gln Gln Val Gln Gln Asp Glu Leu Arg Asn Pro Glu Phe
    130                 135                 140

Gly Lys Glu Lys Thr Gln Thr Tyr Leu Lys Lys Ala Ser Lys Ser Ser
145                 150                 155                 160

Leu Phe Ser Asn Lys Ser Lys Arg Asp Ile Asp Glu Asp Ile Asp Glu
                165                 170                 175

Asp Thr Asp Thr Asp Gly Asp Ala Ile Pro Asp Val Trp Glu Glu Asn
            180                 185                 190

Gly Tyr Thr Ile Lys Gly Arg Val Ala Val Lys Trp Asp Glu Gly Leu
        195                 200                 205

Ala Asp Lys Gly Tyr Lys Lys Phe Val Ser Asn Pro Phe Arg Gln His
    210                 215                 220

Thr Ala Gly Asp Pro Tyr Ser Asp Tyr Glu Lys Ala Ser Lys Asp Leu
225                 230                 235                 240

Asp Leu Ser Asn Ala Lys Glu Thr Phe Asn Pro Leu Val Ala Ala Phe
                245                 250                 255

Pro Ser Val Asn Val Ser Leu Glu Asn Val Thr Ile Ser Lys Asp Glu
            260                 265                 270

Asn Lys Thr Ala Glu Ile Ala Ser Thr Ser Ser Asn Asn Trp Ser Tyr
        275                 280                 285

Thr Asn Thr Glu Gly Ala Ser Ile Glu Ala Gly Ile Gly Pro Glu Gly
    290                 295                 300

Leu Leu Ser Phe Gly Val Ser Ala Asn Tyr Gln His Ser Glu Thr Val
305                 310                 315                 320

Ala Lys Glu Trp Gly Thr Thr Lys Gly Asp Ala Thr Gln Tyr Asn Thr
                325                 330                 335
```

```
Ala Ser Ala Gly Tyr Leu Asn Ala Asn Val Arg Tyr
            340                 345
```

(2) INFORMATION FOR SEQ ID NO: 22:

(i) SEQUENCE CHARACTERISTICS:
(A) LENGTH: 1641 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: 33D2

(xi) SEQUENCE DESCRIPTION: SEQ ID NO: 22:

```
CCAAAGGGGG NTTAAACCNG GANGGTTNNN TNNTTNNTTN TNGAANCCCA NTTGGAAACC     60

CNATNAAATT CNTGGTTANT GGTNGTGAGT GNNTNTTTTA NCNGAGNTTG CCCNTTTGNN    120

TACCNGGATT TNAAGGCAGA ANTTNTTNNT NGCTNNTTAA AGGTTNTGNT TNTNANTGAA    180

TTTTTTNGGN TTTGCCCAAA AAACAAGGAT GAATCCTGTT ATTCCNCCCT NGAAAAAATN    240

GAAACGGAAC AACGTGAGTA TGATAAACAT CTTTTACAAA CTGCGACATC TTGTTGAAAA    300

TGCCTTTTTT GAAAANNTAA AAGGTTTCGT GGCATTGCCA CACGTTATAC AAAAACCACG    360

TCTGCTTTTA GAGGGGCTGT TACCTTGGCT GCTATTTCTC TGTGGTTGAA TCTCGTATAG    420

ACACTATCTA GTCTATACAT CTTATCTTTT CATCATGATT CCAGTCGTAC ATTTACTCAA    480

AAATAGAAAG GATGACCCCT ATGCAATTAA AAAATGTATA CAAATGTTTA ACCATTACAG    540

CGCTTTTGGC TCAAATCGCC GCCTTCCCGT CTTCCTCTTT TGCGGAAGAC GGGAAGAAAA    600

AAGAAGAAAA TACAGCTAAA ACAGAACATC AACAGAAAAA AGAAACAAAA CCAGTTGTGG    660

GATTAATTGG TCACTATTTT ACTGATGATC AGTTTACTAA CACAGCATTT ATTCAAGTAG    720

GAGAAAAAAG TAAATTACTA GATTCAAAAA TAGTAAAGCA AGATATGTCC AATTTGAAAT    780

CCATTCGATG GGAAGGAAAT GTGAAACCTC CTGAAACAGG AGAATATCTA CTTTCCACGT    840

CCTCTAATGA AAATGTTACA GTAAAAGTAG ATGGAGAAAC TGTTATTAAC AAAGCTAACA    900

TGGAAAAAGC AATGAAACTC GAAAAAGATA AACCACACTC TATTGAAATT GAATATCATG    960

TTCCTGAGAA CGGGAAGGAA CTACAATTAT TTTGGCAAAT AAATGACCAG AAAGCTGTTA   1020

AAATCCCAGA AAAAAACATA CTATCACCAA ATCTTTCTGA ACAGATACAA CCGCAACAGC   1080

GTTCAACTCA ATCTCAACAA AATCAAAATG ATAGGGATGG GGATAAAATC CCTGATAGTT   1140

TAGAAGAAAA TGGCTATACA TTTAAAGACG GTGCGATTGT TGCCTGGAAC GATTCCTATG   1200

CAGCACTAGG CTATAAAAAA TACATATCCA ATTCTAATAA GGCTAAAACA GCTGCTGACC   1260

CCTATACGGA CTTTGAAAAA GTAACAGGAC ACATGCCGGA GGCAACTAAA GATGAAGTAA   1320

AAGATCCACT AGTAGCCGCT TATCCCTCGG TAGGTGTTGC TATGGAAAAA TTTCATTTTT   1380

CTAGAAATGA AACGGTCACT GAAGGAGACT CAGGTACTGT TTCAAAAACC GTAACCAATA   1440

CAAGCACAAC AACAAATAGC ATCGATGTTG GGGGATCCAT TGGATGGGGA GAAAAAGGAT   1500

TTTCTTTTTC ATTCTCTCCC AAATATACGC ATTCTTGGAG TAATAGTACC GCTGTTGCTG   1560

ATACTGAAAG TAGCACATGG TCTTCACAAT TAGCGTATAA TCCTTCAGAA CGTGCTTTCT   1620

TAAATGCCAA TATACGATAT A                                              1641
```

(2) INFORMATION FOR SEQ ID NO: 23:

(i) SEQUENCE CHARACTERISTICS:
(A) LENGTH: 327 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: 33D2

(xi) SEQUENCE DESCRIPTION: SEQ ID NO: 23:

```
Gly Leu Ile Gly His Tyr Phe Thr Asp Asp Gln Phe Thr Asn Thr Ala
1               5                   10                  15

Phe Ile Gln Val Gly Glu Lys Ser Lys Leu Leu Asp Ser Lys Ile Val
            20                  25                  30

Lys Gln Asp Met Ser Asn Leu Lys Ser Ile Arg Trp Glu Gly Asn Val
        35                  40                  45

Lys Pro Pro Glu Thr Gly Glu Tyr Leu Leu Ser Thr Ser Ser Asn Glu
    50                  55                  60

Asn Val Thr Val Lys Val Asp Gly Glu Thr Val Ile Asn Lys Ala Asn
65                  70                  75                  80

Met Glu Lys Ala Met Lys Leu Glu Lys Asp Lys Pro His Ser Ile Glu
                85                  90                  95

Ile Glu Tyr His Val Pro Glu Asn Gly Lys Glu Leu Gln Leu Phe Trp
            100                 105                 110

Gln Ile Asn Asp Gln Lys Ala Val Lys Ile Pro Glu Lys Asn Ile Leu
        115                 120                 125

Ser Pro Asn Leu Ser Glu Gln Ile Gln Pro Gln Gln Arg Ser Thr Gln
    130                 135                 140

Ser Gln Gln Asn Gln Asn Asp Arg Asp Gly Asp Lys Ile Pro Asp Ser
145                 150                 155                 160

Leu Glu Glu Asn Gly Tyr Thr Phe Lys Asp Gly Ala Ile Val Ala Trp
                165                 170                 175

Asn Asp Ser Tyr Ala Ala Leu Gly Tyr Lys Lys Tyr Ile Ser Asn Ser
            180                 185                 190

Asn Lys Ala Lys Thr Ala Ala Asp Pro Tyr Thr Asp Phe Glu Lys Val
        195                 200                 205

Thr Gly His Met Pro Glu Ala Thr Lys Asp Glu Val Lys Asp Pro Leu
    210                 215                 220

Val Ala Ala Tyr Pro Ser Val Gly Val Ala Met Glu Lys Phe His Phe
225                 230                 235                 240

Ser Arg Asn Glu Thr Val Thr Glu Gly Asp Ser Gly Thr Val Ser Lys
                245                 250                 255

Thr Val Thr Asn Thr Ser Thr Thr Thr Asn Ser Ile Asp Val Gly Gly
            260                 265                 270

Ser Ile Gly Trp Gly Glu Lys Gly Phe Ser Phe Ser Phe Ser Pro Lys
        275                 280                 285

Tyr Thr His Ser Trp Ser Asn Ser Thr Ala Val Ala Asp Thr Glu Ser
    290                 295                 300

Ser Thr Trp Ser Ser Gln Leu Ala Tyr Asn Pro Ser Glu Arg Ala Phe
305                 310                 315                 320

Leu Asn Ala Asn Ile Arg Tyr
                325
```

(2) INFORMATION FOR SEQ ID NO: 24:

(i) SEQUENCE CHARACTERISTICS:
(A) LENGTH: 1042 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: 66D3

(xi) SEQUENCE DESCRIPTION: SEQ ID NO: 24:

```
TTAATTGGGT ACTATTTTAA AGGAAAAGAT TTTAATAATC TTACTATATT TGCTCCAACA     60

CGTGAGAATA CTCTTATTTA TGATTTAGAA ACAGCGAATT CTTTATTAGA TAAGCAACAA    120

CAAACCTATC AATCTATTCG TTGGATCGGT TTAATAAAAA GCAAAAAAGC TGGAGATTTT    180

ACCTTTCAAT TATCGGATGA TGAGCATGCT ATTATAGAAA TCGATGGGAA AGTTATTTCG    240

CAAAAAGGCC AAAAGAAACA AGTTGTTCAT TTAGAAAAAG ATAAATTAGT TCCCATCAAA    300

ATTGAATATC AATCTGATAA AGCGTTAAAC CCAGATAGTC AAATGTTTAA AGAATTGAAA    360

TTATTTAAAA TAAATAGTCA AAAACAATCT CAGCAAGTGC AACAAGACGA ATTGAGAAAT    420

CCTGAATTTG GTAAAGAAAA AACTCAAACA TATTTAAAGA AAGCATCGAA AAGCAGCCTG    480

TTTAGCAATA AAAGTAAACG AGATATAGAT GAAGATATAG ATGAGGATAC AGATACAGAT    540

GGAGATGCCA TTCCTGATGT ATGGGAAGAA AATGGGTATA CCATCAAAGG AAGAGTAGCT    600

GTTAAATGGG ACGAAGGATT AGCTGATAAG GGATATAAAA AGTTTGTTTC CAATCCTTTT    660

AGACAGCACA CTGCTGGTGA CCCCTATAGT GACTATGAAA AGGCATCAAA AGATTTGGAT    720

TTATCTAATG CAAAAGAAAC ATTTAATCCA TTGGTGGCTG CTTTTCCAAG TGTCAATGTT    780

AGCTTGGAAA ATGTCACCAT ATCAAAAGAT GAAAATAAAA CTGCTGAAAT TGCGTCTACT    840

TCATCGAATA ATTGGTCCTA TACAAATACA GAGGGGGCAT CTATTGAAGC TGGAATTGGA    900

CCAGAAGGTT TGTTGTCTTT TGGAGTAAGT GCCAATTATC AACATTCTGA AACAGTGGCC    960

AAAGAGTGGG GTACAACTAA GGGAGACGCA ACACAATATA ATACAGCTTC AGCAGGATAT   1020

CTAAATGCCA ATGTACGATA TA                                            1042
```

(2) INFORMATION FOR SEQ ID NO: 25:

(i) SEQUENCE CHARACTERISTICS:
(A) LENGTH: 347 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: 66D3

(xi) SEQUENCE DESCRIPTION: SEQ ID NO: 25:

```
Leu Ile Gly Tyr Tyr Phe Lys Gly Lys Asp Phe Asn Asn Leu Thr Ile
1               5                   10                  15

Phe Ala Pro Thr Arg Glu Asn Thr Leu Ile Tyr Asp Leu Glu Thr Ala
            20                  25                  30

Asn Ser Leu Leu Asp Lys Gln Gln Gln Thr Tyr Gln Ser Ile Arg Trp
        35                  40                  45

Ile Gly Leu Ile Lys Ser Lys Lys Ala Gly Asp Phe Thr Phe Gln Leu
    50                  55                  60

Ser Asp Asp Glu His Ala Ile Ile Glu Ile Asp Gly Lys Val Ile Ser
65                  70                  75                  80
```

-continued

```
Gln Lys Gly Gln Lys Lys Gln Val Val His Leu Glu Lys Asp Lys Leu
                85                  90                  95

Val Pro Ile Lys Ile Glu Tyr Gln Ser Asp Lys Ala Leu Asn Pro Asp
            100                 105                 110

Ser Gln Met Phe Lys Glu Leu Lys Leu Phe Lys Ile Asn Ser Gln Lys
        115                 120                 125

Gln Ser Gln Gln Val Gln Gln Asp Glu Leu Arg Asn Pro Glu Phe Gly
    130                 135                 140

Lys Glu Lys Thr Gln Thr Tyr Leu Lys Lys Ala Ser Lys Ser Ser Leu
145                 150                 155                 160

Phe Ser Asn Lys Ser Lys Arg Asp Ile Asp Glu Asp Ile Asp Glu Asp
                165                 170                 175

Thr Asp Thr Asp Gly Asp Ala Ile Pro Asp Val Trp Glu Glu Asn Gly
            180                 185                 190

Tyr Thr Ile Lys Gly Arg Val Ala Val Lys Trp Asp Glu Gly Leu Ala
        195                 200                 205

Asp Lys Gly Tyr Lys Lys Phe Val Ser Asn Pro Phe Arg Gln His Thr
    210                 215                 220

Ala Gly Asp Pro Tyr Ser Asp Tyr Glu Lys Ala Ser Lys Asp Leu Asp
225                 230                 235                 240

Leu Ser Asn Ala Lys Glu Thr Phe Asn Pro Leu Val Ala Ala Phe Pro
                245                 250                 255

Ser Val Asn Val Ser Leu Glu Asn Val Thr Ile Ser Lys Asp Glu Asn
            260                 265                 270

Lys Thr Ala Glu Ile Ala Ser Thr Ser Ser Asn Asn Trp Ser Tyr Thr
        275                 280                 285

Asn Thr Glu Gly Ala Ser Ile Glu Ala Gly Ile Gly Pro Glu Gly Leu
    290                 295                 300

Leu Ser Phe Gly Val Ser Ala Asn Tyr Gln His Ser Glu Thr Val Ala
305                 310                 315                 320

Lys Glu Trp Gly Thr Thr Lys Gly Asp Ala Thr Gln Tyr Asn Thr Ala
                325                 330                 335

Ser Ala Gly Tyr Leu Asn Ala Asn Val Arg Tyr
            340                 345
```

(2) INFORMATION FOR SEQ ID NO: 26:

(i) SEQUENCE CHARACTERISTICS:
- (A) LENGTH: 1278 base pairs
- (B) TYPE: nucleic acid
- (C) STRANDEDNESS: single
- (D) TOPOLOGY: linear (ii) MOLECULE TYPE: DNA (genomic)

(vi) ORIGINAL SOURCE:
- (C) INDIVIDUAL ISOLATE: 68F (xi) SEQUENCE DESCRIPTION: SEQ ID NO: 26:

```
TGGATTACTT GGGTACTATT TTAAAGGGAA AGATTTTAAT GATCTTACTG TATTTGCACC     60

AACGCGTGGG AATACTCTTG TATATGATCA ACAAACAGCA AATACATTAC TAAATCAAAA    120

ACAACAAGAC TTTCAGTCTA TTCGTTGGGT TGGTTTAATT CAAAGTAAAG AAGCAGGCGA    180

TTTTACATTT AACTTATCAG ATGATGAACA TACGATGATA GAAATCGATG GGAAAGTTAT    240

TTCTAATAAA GGGAAAGAAA AACAAGTTGT CCATTTAGAA AAAGGACAGT TCGTTTCTAT    300

CAAAATAGAA TATCAAGCTG ATGAACCATT TAATGCGGAT AGTCAAACCT TTAAAAATTT    360
```

-continued

```
GAAACTCTTT AAAGTAGATA CTAAGCAACA GTCCCAGCAA ATTCAACTAG ATGAATTAAG    420

AAACCCTGAA TTTAATAAAA AAGAAACACA AGAATTTCTA ACAAAAGCAA CAAAAACAAA    480

CCTTATTACT CAAAAAGTGA AGAGTACTAG GGATGAAGAC ACGGATACAG ATGGAGATTC    540

TATTCCAGAC ATTTGGGAAG AAAATGGGTA TACCATCCAA AATAAGATTG CCGTCAAATG    600

GGATGATTCA TTAGCAAGTA AAGGATATAC GAAATTTGTT TCAAACCCAC TAGATACTCA    660

CACGGTTGGA GATCCTTATA CAGATTATGA AAAAGCAGCA AGGGATTTAG ATTTGTCAAA    720

TGCAAAAGAA ACATTTAACC CATTAGTTGC GGCTTTTCCA AGTGTGAATG TGAGTATGGA    780

AAAAGTGATA TTGTCTCCAG ATGAGAACTT ATCAAATAGT ATCGAGTCTC ATTCATCTAC    840

GAATTGGTCG TATACGAATA CAGAAGGGGC TTCTATTGAA GCTGGTGGGG GAGCATTAGG    900

CCTATCTTTT GGTGTAAGTG CAAACTATCA ACATTCTGAA ACAGTTGGGT ATGAATGGGG    960

AACATCTACG GGAAATACTT CGCAATTTAA TACAGCTTCA GCGGGGTATT TAAATGCGAA   1020

TGTTCGCTAC AATAACGTGG GAACGGGTGC AATCTATGAT GTAAAGCCAA CAACGAGTTT   1080

TGTATTAAAT AAAGATACCA TCGCAACGAT AACAGCAAAA TCGAATACGA CTGCATTAAG   1140

TATCTCACCA GGACAAAGTT ATCCGAAACA AGGTCAAAAT GGAATCGCGA TCACATCGAT   1200

GGATGATTTT AACTCACATC CGATTACATT GAATAAGCAA CAGGTAGGTC AACTGTTAAA   1260

TAATACCCAA TTAATCCA                                                 1278
```

(2) INFORMATION FOR SEQ ID NO: 27:

(i) SEQUENCE CHARACTERISTICS:
(A) LENGTH: 425 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: 68F (xi) SEQUENCE DESCRIPTION: SEQ ID NO: 27:

```
Gly Leu Leu Gly Tyr Tyr Phe Lys Gly Lys Asp Phe Asn Asp Leu Thr
1               5                   10                  15

Val Phe Ala Pro Thr Arg Gly Asn Thr Leu Val Tyr Asp Gln Gln Thr
            20                  25                  30

Ala Asn Thr Leu Leu Asn Gln Lys Gln Gln Asp Phe Gln Ser Ile Arg
        35                  40                  45

Trp Val Gly Leu Ile Gln Ser Lys Glu Ala Gly Asp Phe Thr Phe Asn
    50                  55                  60

Leu Ser Asp Asp Glu His Thr Met Ile Glu Ile Asp Gly Lys Val Ile
65                  70                  75                  80

Ser Asn Lys Gly Lys Glu Lys Gln Val Val His Leu Glu Lys Gly Gln
                85                  90                  95

Phe Val Ser Ile Lys Ile Glu Tyr Gln Ala Asp Glu Pro Phe Asn Ala
            100                 105                 110

Asp Ser Gln Thr Phe Lys Asn Leu Lys Leu Phe Lys Val Asp Thr Lys
        115                 120                 125

Gln Gln Ser Gln Gln Ile Gln Leu Asp Glu Leu Arg Asn Pro Glu Phe
    130                 135                 140

Asn Lys Lys Glu Thr Gln Glu Phe Leu Thr Lys Ala Thr Lys Thr Asn
145                 150                 155                 160
```

-continued

```
Leu Ile Thr Gln Lys Val Lys Ser Thr Arg Asp Glu Asp Thr Asp Thr
                165                 170                 175

Asp Gly Asp Ser Ile Pro Asp Ile Trp Glu Glu Asn Gly Tyr Thr Ile
            180                 185                 190

Gln Asn Lys Ile Ala Val Lys Trp Asp Asp Ser Leu Ala Ser Lys Gly
        195                 200                 205

Tyr Thr Lys Phe Val Ser Asn Pro Leu Asp Thr His Thr Val Gly Asp
    210                 215                 220

Pro Tyr Thr Asp Tyr Glu Lys Ala Ala Arg Asp Leu Asp Leu Ser Asn
225                 230                 235                 240

Ala Lys Glu Thr Phe Asn Pro Leu Val Ala Ala Phe Pro Ser Val Asn
                245                 250                 255

Val Ser Met Glu Lys Val Ile Leu Ser Pro Asp Glu Asn Leu Ser Asn
            260                 265                 270

Ser Ile Glu Ser His Ser Ser Thr Asn Trp Ser Tyr Thr Asn Thr Glu
        275                 280                 285

Gly Ala Ser Ile Glu Ala Gly Gly Gly Ala Leu Gly Leu Ser Phe Gly
    290                 295                 300

Val Ser Ala Asn Tyr Gln His Ser Glu Thr Val Gly Tyr Glu Trp Gly
305                 310                 315                 320

Thr Ser Thr Gly Asn Thr Ser Gln Phe Asn Thr Ala Ser Ala Gly Tyr
                325                 330                 335

Leu Asn Ala Asn Val Arg Tyr Asn Asn Val Gly Thr Gly Ala Ile Tyr
            340                 345                 350

Asp Val Lys Pro Thr Thr Ser Phe Val Leu Asn Lys Asp Thr Ile Ala
        355                 360                 365

Thr Ile Thr Ala Lys Ser Asn Thr Thr Ala Leu Ser Ile Ser Pro Gly
    370                 375                 380

Gln Ser Tyr Pro Lys Gln Gly Gln Asn Gly Ile Ala Ile Thr Ser Met
385                 390                 395                 400

Asp Asp Phe Asn Ser His Pro Ile Thr Leu Asn Lys Gln Gln Val Gly
                405                 410                 415

Gln Leu Leu Asn Asn Thr Gln Leu Ile
            420                 425
```

(2) INFORMATION FOR SEQ ID NO: 28:

(i) SEQUENCE CHARACTERISTICS:
(A) LENGTH: 983 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: 69AA2

(xi) SEQUENCE DESCRIPTION: SEQ ID NO: 28:

```
TGGATTACTT GGGTACTATT TTACTGATGA TCAGTTTACT AACACAGCAT TTATTCAAGT     60

AGGAGAAAAA AGTAAATTAC TAGATTCAAA AATAGTAAAA CAAGATATGT CCAATTTGAA    120

ATCCATTCGA TGGGAAGGAA ATGTGAAACC TCCTGAAACA GGAGAATATC TACTTTCCAC    180

GTCCTCTAAT GAAAATGTTA CAGTAAAAGT AGATGGAGAA ACTGTTATTA ACAAAGCTAA    240

CATGGAAAAA GCAATGAAAC TCGAAAAAGA TAAACCACAC TCTATTGAAA TTGAATATCA    300

TGTTCCTGAG AACGGGAAGG AACTACAATT ATTTTGGCAA ATAAATGACC AGAAAGCTGT    360
```

-continued

```
TAAAATCCCA GAAAAAAACA TACTATCACC AAATCTTTCT GAACAGATAC AACCGCAACA    420

GCGTTCAACT CAATCTCAAC AAAATCAAAA TGATAGGGAT GGGGATAAAA TCCCTGATAG    480

TTTAGAAGAA AATGGCTATA CATTTAAAGA CGGTGCGATT GTTGCCTGGA ACGATTCCTA    540

TGCAGCACTA GGCTATAAAA AATACATATC CAATTCTAAT AAGGCTAAAA CAGCTGCTGA    600

CCCCTATACG GACTTTGAAA AAGTAACAGG ACACATGCCG GAGGCAACTA AAGATGAAGT    660

AAAAGATCCA CTAGTAGCCG CTTATCCCTC GGTAGGTGTT GCTATGGAAA AATTTCATTT    720

TTCTAGAAAT GAAACGGTCA CTGAAGGAGA CTCAGGTACT GTTTCAAAAA CCGTAACCAA    780

TACAAGCACA ACAACAAATA GCATCGATGT TGGGGGATCC ATTGGATGGG GAGAAAAAGG    840

ATTTTCTTTT TCATTCTCTC CCAAATATAC GCATTCTTGG AGTAATAGTA CCGCTGTTGC    900

TGATACTGAA AGTAGCACAT GGTCTTCACA ATTAGCGTAT AATCCTTCAG AACGTGCTNT    960

CTTAAATGCC AATAKACGAT NTA                                            983
```

(2) INFORMATION FOR SEQ ID NO: 29:

(i) SEQUENCE CHARACTERISTICS:
(A) LENGTH: 327 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: 69AA2

(xi) SEQUENCE DESCRIPTION: SEQ ID NO: 29:

```
Gly Leu Leu Gly Tyr Tyr Phe Thr Asp Asp Gln Phe Thr Asn Thr Ala
1               5                   10                  15

Phe Ile Gln Val Gly Glu Lys Ser Lys Leu Leu Asp Ser Lys Ile Val
            20                  25                  30

Lys Gln Asp Met Ser Asn Leu Lys Ser Ile Arg Trp Glu Gly Asn Val
        35                  40                  45

Lys Pro Pro Glu Thr Gly Glu Tyr Leu Leu Ser Thr Ser Ser Asn Glu
    50                  55                  60

Asn Val Thr Val Lys Val Asp Gly Glu Thr Val Ile Asn Lys Ala Asn
65                  70                  75                  80

Met Glu Lys Ala Met Lys Leu Glu Lys Asp Lys Pro His Ser Ile Glu
                85                  90                  95

Ile Glu Tyr His Val Pro Glu Asn Gly Lys Glu Leu Gln Leu Phe Trp
            100                 105                 110

Gln Ile Asn Asp Gln Lys Ala Val Lys Ile Pro Glu Lys Asn Ile Leu
        115                 120                 125

Ser Pro Asn Leu Ser Glu Gln Ile Gln Pro Gln Gln Arg Ser Thr Gln
    130                 135                 140

Ser Gln Gln Asn Gln Asn Asp Arg Asp Gly Asp Lys Ile Pro Asp Ser
145                 150                 155                 160

Leu Glu Glu Asn Gly Tyr Thr Phe Lys Asp Gly Ala Ile Val Ala Trp
                165                 170                 175

Asn Asp Ser Tyr Ala Ala Leu Gly Tyr Lys Lys Tyr Ile Ser Asn Ser
            180                 185                 190

Asn Lys Ala Lys Thr Ala Ala Asp Pro Tyr Thr Asp Phe Glu Lys Val
        195                 200                 205

Thr Gly His Met Pro Glu Ala Thr Lys Asp Glu Val Lys Asp Pro Leu
    210                 215                 220
```

-continued

```
Val Ala Ala Tyr Pro Ser Val Gly Val Ala Met Glu Lys Phe His Phe
225                 230                 235                 240

Ser Arg Asn Glu Thr Val Thr Glu Gly Asp Ser Gly Thr Val Ser Lys
                245                 250                 255

Thr Val Thr Asn Thr Ser Thr Thr Thr Asn Ser Ile Asp Val Gly Gly
            260                 265                 270

Ser Ile Gly Trp Gly Glu Lys Gly Phe Ser Phe Ser Phe Ser Pro Lys
        275                 280                 285

Tyr Thr His Ser Trp Ser Asn Ser Thr Ala Val Ala Asp Thr Glu Ser
    290                 295                 300

Ser Thr Trp Ser Ser Gln Leu Ala Tyr Asn Pro Ser Glu Arg Ala Xaa
305                 310                 315                 320

Leu Asn Ala Asn Xaa Arg Xaa
                325
```

(2) INFORMATION FOR SEQ ID NO: 30:

(i) SEQUENCE CHARACTERISTICS:
(A) LENGTH: 1075 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: 168G1

(xi) SEQUENCE DESCRIPTION: SEQ ID NO: 30:

```
TGGGTTAATT GGATATTATT TCCAGGATCA AAAATTTCAA CAACTCGCTT TAATGGTACA     60

TAGGCAAGCT TCTGATTTAA AAATACTGAA AGATGACGTG AAACATTTAC TATCCGAAGA    120

TCAACAACAC ATTCAATCAG TAAGGTGGAT AGGCTATATT AAGCCACCTA AAACAGGAGA    180

CTACGTATTG TCAACCTCAT CCGACCAACA GGTCATGATT GAACTAGATG GTAAAGTCAT    240

TCTCAATCAG GCTTCTATGA CAGAACCTGT TCAACTTGAA AAAGATAAAC CGTATAAAAT    300

TAAAATTGAA TATGTTCCGG AACAAACAGA AACACAAGAT ACGCTTCTTG ATTTTAAACT    360

GAACTGGTCT TTTTCAGGCG GAAAAACAGA AACGATTCCA GAAAATGCAT TTCTATTACC    420

AGACCTTTCT CGTAAACAAG ATCAAGAAAA GCTTATTCCT GAGGCAAGTT TATTTCAGAA    480

ACCTGGAGAC GAGAAAAAAA TATCTCGAAG TAAACGGTCC TTTAACTACA GATTCTCTAT    540

ATGATACAAG ATGATGATGG GATTTCGGAT GCGTGGGAAA CAGAAGGATA CACGATACAA    600

AGACAACTGG CAGTGAAATG GGACGATTCT ATGAAGGATC GAGGGTATAC CAAATATGTA    660

TCTAATCCCT ATAATTCCCA TACAGTAGGG GATCCATACA CAGATTGGGA AAAAGCGGCT    720

GGACGTATTG ATAAGGCGAT CAAAGGAGAA GCTAGGAATC CTTTAGTCGC GGCCTATCCA    780

ACCGTTGGTG TACATATGGA AAAACTGATT GTCTCCGAGA AACAAAACAT ATCAACTGGA    840

CTCGGAAAAA CAATATCTGC GTCAATGTCT GCAAGTAATA CCGCAGCGAT TACAGCGGGC    900

ATTGATACGA CGGCTGGTGC TTCTTTACTT GGACCGTCTG GAAGCGTCAC GGCTCATTTT    960

TCTGATACAG GATCCAGTAC ATCCACTGTT GAAAATAGCT CAAGTAATAA TTGGAGTCAA   1020

GATCTTGGAA TCGATACGGG ACAATCTGCA TATTTAAATG CCAATGTACG ATATA        1075
```

(2) INFORMATION FOR SEQ ID NO: 31:

(i) SEQUENCE CHARACTERISTICS:
(A) LENGTH: 2645 base pairs

-continued (B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: PS177C8

(xi) SEQUENCE DESCRIPTION: SEQ ID NO: 31:

```
ATGAAGAAGA AGTTAGCAAG TGTTGTAACG TGTACGTTAT TAGCTCCTAT GTTTTTGAAT     60
GGAAATGTGA ATGCTGTTTA CGCAGACAGC AAAACAAATC AAATTTCTAC AACACAGAAA    120
AATCAACAGA AAGAGATGGA CCGAAAAGGA TTACTTGGGT ATTATTTCAA AGGAAAAGAT    180
TTTAGTAATC TTACTATGTT TGCACCGACA CGTGATAGTA CTCTTATTTA TGATCAACAA    240
ACAGCAAATA AACTATTAGA TAAAAAACAA CAAGAATATC AGTCTATTCG TTGGATTGGT    300
TTGATTCAGA GTAAAGAAAC GGGAGATTTC ACATTTAACT TATCTGAGGA TGAACAGGCA    360
ATTATAGAAA TCAATGGGAA AATTATTTCT AATAAAGGGA AAGAAAAGCA AGTTGTCCAT    420
TTAGAAAAAG GAAAATTAGT TCCAATCAAA ATAGAGTATC AATCAGATAC AAAATTTAAT    480
ATTGACAGTA AAACATTTAA AGAACTTAAA TTATTTAAAA TAGATAGTCA AAACCAACCC    540
CAGCAAGTCC AGCAAGATGA ACTGAGAAAT CCTGAATTTA ACAAGAAAGA ATCACAGGAA    600
TTCTTAGCGA AACCATCGAA AATAAATCTT TTCACTCAAA AAATGAAAAG GGAAATTGAT    660
GAAGACACGG ATACGGATGG GGACTCTATT CCTGACCTTT GGGAAGAAAA TGGGTATACG    720
ATTCAAAATA GAATCGCTGT AAAGTGGGAC GATTCTYTAG CAAGTAAAGG GTATACGAAA    780
TTTGTTTCAA ATCCGCTAGA AAGTCACACA GTTGGTGATC CTTATACAGA TTATGAAAAG    840
GCAGCAAGAG ACCTAGATTT GTCAAATGCA AAGGAAACGT TTAACCCATT GGTAGCTGCT    900
TTTCCAAGTG TGAATGTTAG TATGGAAAAG GTGATATTAT CACCAAATGA AAATTTATCC    960
AATAGTGTAG AGTCTCATTC ATCCACGAAT TGGTCTTATA CAAATACAGA AGGTGCTTCT   1020
GTTGAAGCGG GGATTGGACC AAAAGGTATT TCGTTCGGAG TTAGCGTAAA CTATCAACAC   1080
TCTGAAACAG TTGCACAAGA ATGGGGAACA TCTACAGGAA ATACTTCGCA ATTCAATACG   1140
GCTTCAGCGG GATATTTAAA TGCAAATGTT CGATATAACA ATGTAGGAAC TGGTGCCATC   1200
TACGATGTAA AACCTACAAC AAGTTTTGTA TTAAATAACG ATACTATCGC AACTATTACG   1260
GCGAAATCTA ATTCTACAGC CTTAAATATA TCTCCTGGAG AAAGTTACCC GAAAAAAGGA   1320
CAAAATGGAA TCGCAATAAC ATCAATGGAT GATTTTAATT CCCATCCGAT TACATTAAAT   1380
AAAAAACAAG TAGATAATCT GCTAAATAAT AAACCTATGA TGTTGGAAAC AAACCAAACA   1440
GATGGTGTTT ATAAGATAAA AGATACACAT GGAAATATAG TAACTGGCGG AGAATGGAAT   1500
GGTGTCATAC AACAAATCAA GGCTAAAACA GCGTCTATTA TTGTGGATGA TGGGGAACGT   1560
GTAGCAGAAA AACGTGTAGC GGCAAAAGAT TATGAAAATC CAGAAGATAA AACACCGTCT   1620
TTAACTTTAA AAGATGCCCT GAAGCTTTCA TATCCAGATG AAATAAAAGA AATAGAGGGA   1680
TTATTATATT ATAAAAACAA ACCGATATAC GAATCGAGCG TTATGACTTA CTTAGATGAA   1740
AATACAGCAA AAGAAGTGAC CAAACAATTA AATGATACCA CTGGGAAATT TAAAGATGTA   1800
AGTCATTTAT ATGATGTAAA ACTGACTCCA AAAATGAATG TTACAATCAA ATTGTCTATA   1860
CTTTATGATA ATGCTGAGTC TAATGATAAC TCAATTGGTA AATGGACAAA CACAAATATT   1920
GTTTCAGGTG GAAATAACGG AAAAAAACAA TATTCTTCTA ATAATCCGGA TGCTAATTTG   1980
ACATTAAATA CAGATGCTCA AGAAAAATTA AATAAAAATC GTACTATTAT ATAAGTTTAT   2040
```

```
ATATGAAGTC AGAAAAAAAC ACACAATGTG AGATTACTAT AGATGGGGAG ATTTATCCGA   2100

TCACTACAAA AACAGTGAAT GTGAATAAAG ACAATTACAA AAGATTAGAT ATTATAGCTC   2160

ATAATATAAA AAGTAATCCA ATTTCTTCAA TTCATATTAA AACGAATGAT GAAATAACTT   2220

TATTTTGGGA TGATATTTCT ATAACAGATG TAGCATCAAT AAAACCGGAA AATTTAACAG   2280

ATTCAGAAAT TAAACAGATT TATAGTAGGT ATGGTATTAA GTTAGAAGAT GGAATCCTTA   2340

TTGATAAAAA AGGTGGGATT CATTATGGTG AATTTATTAA TGAAGCTAGT TTTAATATTG   2400

AACCATTGCA AAATTATGTG ACAAAATATA AAGTTACTTA TAGTAGTGAG TTAGGACAAA   2460

ACGTGAGTGA CACACTTGAA AGTGATAAAA TTTACAAGGA TGGGACAATT AAATTTGATT   2520

TTACAAAATA TAGTRAAAAT GAACAAGGAT TATTTTATGA CAGTGGATTA AATTGGGACT   2580

TTAAAATTAA TGCTATTACT TATGATGGTA AAGAGATGAA TGTTTTTCAT AGATATAATA   2640

AATAG                                                               2645
```

(2) INFORMATION FOR SEQ ID NO: 32:

(i) SEQUENCE CHARACTERISTICS:
(A) LENGTH: 881 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: PS177C8

(xi) SEQUENCE DESCRIPTION: SEQ ID NO: 32:

```
Met Lys Lys Lys Leu Ala Ser Val Val Thr Cys Thr Leu Leu Ala Pro
1               5                   10                  15

Met Phe Leu Asn Gly Asn Val Asn Ala Val Tyr Ala Asp Ser Lys Thr
            20                  25                  30

Asn Gln Ile Ser Thr Thr Gln Lys Asn Gln Gln Lys Glu Met Asp Arg
        35                  40                  45

Lys Gly Leu Leu Gly Tyr Tyr Phe Lys Gly Lys Asp Phe Ser Asn Leu
    50                  55                  60

Thr Met Phe Ala Pro Thr Arg Asp Ser Thr Leu Ile Tyr Asp Gln Gln
65                  70                  75                  80

Thr Ala Asn Lys Leu Leu Asp Lys Lys Gln Gln Glu Tyr Gln Ser Ile
                85                  90                  95

Arg Trp Ile Gly Leu Ile Gln Ser Lys Glu Thr Gly Asp Phe Thr Phe
            100                 105                 110

Asn Leu Ser Glu Asp Glu Gln Ala Ile Ile Glu Ile Asn Gly Lys Ile
        115                 120                 125

Ile Ser Asn Lys Gly Lys Glu Lys Gln Val Val His Leu Glu Lys Gly
    130                 135                 140

Lys Leu Val Pro Ile Lys Ile Glu Tyr Gln Ser Asp Thr Lys Phe Asn
145                 150                 155                 160

Ile Asp Ser Lys Thr Phe Lys Glu Leu Lys Leu Phe Lys Ile Asp Ser
                165                 170                 175

Gln Asn Gln Pro Gln Gln Val Gln Gln Asp Glu Leu Arg Asn Pro Glu
            180                 185                 190

Phe Asn Lys Lys Glu Ser Gln Glu Phe Leu Ala Lys Pro Ser Lys Ile
        195                 200                 205

Asn Leu Phe Thr Gln Lys Met Lys Arg Glu Ile Asp Glu Asp Thr Asp
    210                 215                 220
```

-continued

```
Thr Asp Gly Asp Ser Ile Pro Asp Leu Trp Glu Glu Asn Gly Tyr Thr
225                 230                 235                 240

Ile Gln Asn Arg Ile Ala Val Lys Trp Asp Asp Ser Leu Ala Ser Lys
                245                 250                 255

Gly Tyr Thr Lys Phe Val Ser Asn Pro Leu Glu Ser His Thr Val Gly
            260                 265                 270

Asp Pro Tyr Thr Asp Tyr Glu Lys Ala Ala Arg Asp Leu Asp Leu Ser
        275                 280                 285

Asn Ala Lys Glu Thr Phe Asn Pro Leu Val Ala Ala Phe Pro Ser Val
    290                 295                 300

Asn Val Ser Met Glu Lys Val Ile Leu Ser Pro Asn Glu Asn Leu Ser
305                 310                 315                 320

Asn Ser Val Glu Ser His Ser Ser Thr Asn Trp Ser Tyr Thr Asn Thr
                325                 330                 335

Glu Gly Ala Ser Val Glu Ala Gly Ile Gly Pro Lys Gly Ile Ser Phe
            340                 345                 350

Gly Val Ser Val Asn Tyr Gln His Ser Glu Thr Val Ala Gln Glu Trp
        355                 360                 365

Gly Thr Ser Thr Gly Asn Thr Ser Gln Phe Asn Thr Ala Ser Ala Gly
    370                 375                 380

Tyr Leu Asn Ala Asn Val Arg Tyr Asn Asn Val Gly Thr Gly Ala Ile
385                 390                 395                 400

Tyr Asp Val Lys Pro Thr Thr Ser Phe Val Leu Asn Asn Asp Thr Ile
                405                 410                 415

Ala Thr Ile Thr Ala Lys Ser Asn Ser Thr Ala Leu Asn Ile Ser Pro
            420                 425                 430

Gly Glu Ser Tyr Pro Lys Lys Gly Gln Asn Gly Ile Ala Ile Thr Ser
        435                 440                 445

Met Asp Asp Phe Asn Ser His Pro Ile Thr Leu Asn Lys Lys Gln Val
    450                 455                 460

Asp Asn Leu Leu Asn Asn Lys Pro Met Met Leu Glu Thr Asn Gln Thr
465                 470                 475                 480

Asp Gly Val Tyr Lys Ile Lys Asp Thr His Gly Asn Ile Val Thr Gly
                485                 490                 495

Gly Glu Trp Asn Gly Val Ile Gln Gln Ile Lys Ala Lys Thr Ala Ser
            500                 505                 510

Ile Ile Val Asp Asp Gly Glu Arg Val Ala Glu Lys Arg Val Ala Ala
        515                 520                 525

Lys Asp Tyr Glu Asn Pro Glu Asp Lys Thr Pro Ser Leu Thr Leu Lys
    530                 535                 540

Asp Ala Leu Lys Leu Ser Tyr Pro Asp Glu Ile Lys Glu Ile Glu Gly
545                 550                 555                 560

Leu Leu Tyr Tyr Lys Asn Lys Pro Ile Tyr Glu Ser Ser Val Met Thr
                565                 570                 575

Tyr Leu Asp Glu Asn Thr Ala Lys Glu Val Thr Lys Gln Leu Asn Asp
            580                 585                 590

Thr Thr Gly Lys Phe Lys Asp Val Ser His Leu Tyr Asp Val Lys Leu
        595                 600                 605

Thr Pro Lys Met Asn Val Thr Ile Lys Leu Ser Ile Leu Tyr Asp Asn
    610                 615                 620

Ala Glu Ser Asn Asp Asn Ser Ile Gly Lys Trp Thr Asn Thr Asn Ile
625                 630                 635                 640
```

-continued

```
Val Ser Gly Gly Asn Asn Gly Lys Lys Gln Tyr Ser Ser Asn Asn Pro
                645                 650                 655

Asp Ala Asn Leu Thr Leu Asn Thr Asp Ala Gln Glu Lys Leu Asn Lys
            660                 665                 670

Asn Arg Asp Tyr Tyr Ile Ser Leu Tyr Met Lys Ser Glu Lys Asn Thr
        675                 680                 685

Gln Cys Glu Ile Thr Ile Asp Gly Glu Ile Tyr Pro Ile Thr Thr Lys
    690                 695                 700

Thr Val Asn Val Asn Lys Asp Asn Tyr Lys Arg Leu Asp Ile Ile Ala
705                 710                 715                 720

His Asn Ile Lys Ser Asn Pro Ile Ser Ser Ile His Ile Lys Thr Asn
                725                 730                 735

Asp Glu Ile Thr Leu Phe Trp Asp Asp Ile Ser Ile Thr Asp Val Ala
            740                 745                 750

Ser Ile Lys Pro Glu Asn Leu Thr Asp Ser Glu Ile Lys Gln Ile Tyr
        755                 760                 765

Ser Arg Tyr Gly Ile Lys Leu Glu Asp Gly Ile Leu Ile Asp Lys Lys
    770                 775                 780

Gly Gly Ile His Tyr Gly Glu Phe Ile Asn Glu Ala Ser Phe Asn Ile
785                 790                 795                 800

Glu Pro Leu Gln Asn Tyr Val Thr Lys Tyr Lys Val Thr Tyr Ser Ser
                805                 810                 815

Glu Leu Gly Gln Asn Val Ser Asp Thr Leu Glu Ser Asp Lys Ile Tyr
            820                 825                 830

Lys Asp Gly Thr Ile Lys Phe Asp Phe Thr Lys Tyr Ser Xaa Asn Glu
        835                 840                 845

Gln Gly Leu Phe Tyr Asp Ser Gly Leu Asn Trp Asp Phe Lys Ile Asn
    850                 855                 860

Ala Ile Thr Tyr Asp Gly Lys Glu Met Asn Val Phe His Arg Tyr Asn
865                 870                 875                 880

Lys
```

(2) INFORMATION FOR SEQ ID NO: 33:

(i) SEQUENCE CHARACTERISTICS:
(A) LENGTH: 1022 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: 177I8

(xi) SEQUENCE DESCRIPTION: SEQ ID NO: 33:

```
TGGATTAATT GGGTATTATT TCAAAGGAAA AGATTTTAAT AATCTTACTA TGTTTGCACC     60

GACACGTGAT AATACCCTTA TGTATGACCA ACAAACAGCG AATGCATTAT TAGATAAAAA    120

ACAACAAGAA TATCAGTCCA TTCGTTGGAT TGGTTTGATT CAGAGTAAAG AAACGGGCGA    180

TTTCACATTT AACTTATCAA AGGATGAACA GGCAATTATA GAAATCGATG GGAAAATCAT    240

TTCTAATAAA GGGAAAGAAA AGCAAGTTGT CCATTTAGAA AAAGAAAAAT TAGTTCCAAT    300

CAAAATAGAG TATCAATCAG ATACGAAATT TAATATTGAT AGTAAAACAT TTAAAGAACT    360

TAAATTATTT AAAATAGATA GTCAAAACCA ATCTCAACAA GTTCAACTGA GAAACCCTGA    420

ATTTAACAAA AAAGAATCAC AGGAATTTTT AGCAAAAGCA TCAAAAACAA ACCTTTTTAA    480
```

-continued

```
GCAAAAAATG AAAAGAGATA TTGATGAAGA TACGGATACA GATGGAGACT CCATTCCTGA    540

TCTTTGGGAA GAAAATGGGT ACACGATTCA AAATAAAGTT GCTGTCAAAT GGGATGATTC    600

GCTAGCAAGT AAGGGATATA CAAAATTTGT TTCGAATCCA TTAGACAGCC ACACAGTTGG    660

CGATCCCTAT ACTGATTATG AAAAGGCCGC AAGGGATTTA GATTTATCAA ATGCAAAGGA    720

AACGTTCAAC CCATTGGTAG CTGCTTTYCC AAGTGTGAAT GTTAGTATGG AAAAGGTGAT    780

ATTATCACCA AATGAAAATT TATCCAATAG TGTAGAGTCT CATTCATCCA CGAATTGGTC    840

TTATACGAAT ACAGAAGGAG CTTCCATTGA AGCTGGTGGC GGTCCATTAG GCCTTTCTTT    900

TGGAGTGAGT GTTAATTATC AACACTCTGA AACAGTTGCA CAAGAATGGG GAACATCTAC    960

AGGAAATACT TCACAATTCA ATACGGCTTC AGCGGGATAT TTAAATGCCA ATATACGATA   1020

TA                                                                  1022
```

(2) INFORMATION FOR SEQ ID NO: 34:

(i) SEQUENCE CHARACTERISTICS:
(A) LENGTH: 340 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: 177I8

(xi) SEQUENCE DESCRIPTION: SEQ ID NO: 34:

```
Gly Leu Ile Gly Tyr Tyr Phe Lys Gly Lys Asp Phe Asn Asn Leu Thr
1               5                   10                  15

Met Phe Ala Pro Thr Arg Asp Asn Thr Leu Met Tyr Asp Gln Gln Thr
            20                  25                  30

Ala Asn Ala Leu Leu Asp Lys Lys Gln Gln Glu Tyr Gln Ser Ile Arg
        35                  40                  45

Trp Ile Gly Leu Ile Gln Ser Lys Glu Thr Gly Asp Phe Thr Phe Asn
    50                  55                  60

Leu Ser Lys Asp Glu Gln Ala Ile Ile Glu Ile Asp Gly Lys Ile Ile
65                  70                  75                  80

Ser Asn Lys Gly Lys Glu Lys Gln Val Val His Leu Glu Lys Glu Lys
                85                  90                  95

Leu Val Pro Ile Lys Ile Glu Tyr Gln Ser Asp Thr Lys Phe Asn Ile
            100                 105                 110

Asp Ser Lys Thr Phe Lys Glu Leu Lys Leu Phe Lys Ile Asp Ser Gln
        115                 120                 125

Asn Gln Ser Gln Gln Val Gln Leu Arg Asn Pro Glu Phe Asn Lys Lys
    130                 135                 140

Glu Ser Gln Glu Phe Leu Ala Lys Ala Ser Lys Thr Asn Leu Phe Lys
145                 150                 155                 160

Gln Lys Met Lys Arg Asp Ile Asp Glu Asp Thr Asp Thr Asp Gly Asp
                165                 170                 175

Ser Ile Pro Asp Leu Trp Glu Glu Asn Gly Tyr Thr Ile Gln Asn Lys
            180                 185                 190

Val Ala Val Lys Trp Asp Asp Ser Leu Ala Ser Lys Gly Tyr Thr Lys
        195                 200                 205

Phe Val Ser Asn Pro Leu Asp Ser His Thr Val Gly Asp Pro Tyr Thr
    210                 215                 220

Asp Tyr Glu Lys Ala Ala Arg Asp Leu Asp Leu Ser Asn Ala Lys Glu
```

-continued

```
225                 230                 235                 240

Thr Phe Asn Pro Leu Val Ala Ala Xaa Pro Ser Val Asn Val Ser Met
            245                 250                 255

Glu Lys Val Ile Leu Ser Pro Asn Glu Asn Leu Ser Asn Ser Val Glu
            260                 265                 270

Ser His Ser Ser Thr Asn Trp Ser Tyr Thr Asn Thr Glu Gly Ala Ser
        275                 280                 285

Ile Glu Ala Gly Gly Gly Pro Leu Gly Leu Ser Phe Gly Val Ser Val
    290                 295                 300

Asn Tyr Gln His Ser Glu Thr Val Ala Gln Glu Trp Gly Thr Ser Thr
305                 310                 315                 320

Gly Asn Thr Ser Gln Phe Asn Thr Ala Ser Ala Gly Tyr Leu Asn Ala
            325                 330                 335

Asn Ile Arg Tyr
            340
```

(2) INFORMATION FOR SEQ ID NO: 35:

(i) SEQUENCE CHARACTERISTICS:
(A) LENGTH: 1073 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: 185AA2

(xi) SEQUENCE DESCRIPTION: SEQ ID NO: 35:

```
TGGATTAATT GGGTATTATT TCCAGGAGCA AAACTTTGAG AAACCCGCTT TGATAGCAAA     60

TAGACAAGCT TCTGATTTGG AAATACCGAA AGATGACGTG AAAGAGTTAC TATCCAAAGA    120

ACAGCAACAC ATTCAATCTG TTAGATGGCT TGGCTATATT CAGCCACCTC AAACAGGAGA    180

CTATGTATTG TCAACCTCAT CCGACCAACA GGTCGTGATT GAACTCGATG GAAAAACCAT    240

TGTCAATCAA ACTTCTATGA CAGAACCGAT TCAACTAGAA AAAGATAAAC GCTATAAAAT    300

TAGAATTGAA TATGTCCCAG GAGATACACA AGGACAAGAG AACCTTCTGG ACTTTCAACT    360

GAAGTGGTCA ATTTCAGGAG CCGAGATAGA ACCAATTCCG GATCATGCTT TCCATTTACC    420

AGATTTTTCT CATAAACAAG ATCAAGAGAA AATCATCCCT GAAACCAATT TATTTCAGAA    480

ACAAGGAGAT GAGAAAAAAG TATCACGCAG TAAGAGATCT TCAGATAAAG ATCCTGACCG    540

TGATACAGAT GATGATAGTA TTTCTGATGA ATGGGAAACG AGTGGATATA CCATTCAAAG    600

ACAGGTGGCA GTGAAATGGG ACGATTCTAT GAAGGAGCTA GGTTATACCA AGTATGTGTC    660

TAACCCTTAT AAGTCTCGTA CAGTAGGAGA TCCATACACA GATTGGGAAA AAGCGGCTGG    720

CAGTATCGAT AATGCTGTCA AAGCAGAAGC CAGAAATCCT TTAGTCGCGG CCTATCCAAC    780

TGTTGGTGTA CATATGGAAA GATTAATTGT CTCCGAACAA CAAAATATAT CAACAGGGCT    840

TGGAAAAACC GTATCTGCGT CTACGTCCGC AAGCAATACC GCAGCGATTA CGGCAGGTAT    900

TGATGCAACA GCTGGTGCCT CTTTACTTGG GCCATCTGGA AGTGTCACGG CTCATTTTTC    960

TTACACGGGA TCTAGTACAG CCACCATTGA AGATAGCTCC AGCCGTAATT GGAGTCGAGA   1020

CCTTGGGATT GATACGGGAC AAGCTGCATA TTTAAATGCC AATATACGAT ATA          1073
```

(2) INFORMATION FOR SEQ ID NO: 36:

(i) SEQUENCE CHARACTERISTICS:

(A) LENGTH: 357 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: 185AA2

(xi) SEQUENCE DESCRIPTION: SEQ ID NO: 36:

```
Gly Leu Ile Gly Tyr Tyr Phe Gln Glu Gln Asn Phe Glu Lys Pro Ala
1               5                   10                  15

Leu Ile Ala Asn Arg Gln Ala Ser Asp Leu Glu Ile Pro Lys Asp Asp
            20                  25                  30

Val Lys Glu Leu Leu Ser Lys Glu Gln Gln His Ile Gln Ser Val Arg
        35                  40                  45

Trp Leu Gly Tyr Ile Gln Pro Pro Gln Thr Gly Asp Tyr Val Leu Ser
    50                  55                  60

Thr Ser Ser Asp Gln Gln Val Val Ile Glu Leu Asp Gly Lys Thr Ile
65                  70                  75                  80

Val Asn Gln Thr Ser Met Thr Glu Pro Ile Gln Leu Glu Lys Asp Lys
                85                  90                  95

Arg Tyr Lys Ile Arg Ile Glu Tyr Val Pro Gly Asp Thr Gln Gly Gln
            100                 105                 110

Glu Asn Leu Leu Asp Phe Gln Leu Lys Trp Ser Ile Ser Gly Ala Glu
        115                 120                 125

Ile Glu Pro Ile Pro Asp His Ala Phe His Leu Pro Asp Phe Ser His
    130                 135                 140

Lys Gln Asp Gln Glu Lys Ile Ile Pro Glu Thr Asn Leu Phe Gln Lys
145                 150                 155                 160

Gln Gly Asp Glu Lys Lys Val Ser Arg Ser Lys Arg Ser Ser Asp Lys
                165                 170                 175

Asp Pro Asp Arg Asp Thr Asp Asp Asp Ser Ile Ser Asp Glu Trp Glu
            180                 185                 190

Thr Ser Gly Tyr Thr Ile Gln Arg Gln Val Ala Val Lys Trp Asp Asp
        195                 200                 205

Ser Met Lys Glu Leu Gly Tyr Thr Lys Tyr Val Ser Asn Pro Tyr Lys
    210                 215                 220

Ser Arg Thr Val Gly Asp Pro Tyr Thr Asp Trp Glu Lys Ala Ala Gly
225                 230                 235                 240

Ser Ile Asp Asn Ala Val Lys Ala Glu Ala Arg Asn Pro Leu Val Ala
                245                 250                 255

Ala Tyr Pro Thr Val Gly Val His Met Glu Arg Leu Ile Val Ser Glu
            260                 265                 270

Gln Gln Asn Ile Ser Thr Gly Leu Gly Lys Thr Val Ser Ala Ser Thr
        275                 280                 285

Ser Ala Ser Asn Thr Ala Ala Ile Thr Ala Gly Ile Asp Ala Thr Ala
    290                 295                 300

Gly Ala Ser Leu Leu Gly Pro Ser Gly Ser Val Thr Ala His Phe Ser
305                 310                 315                 320

Tyr Thr Gly Ser Ser Thr Ala Thr Ile Glu Asp Ser Ser Ser Arg Asn
                325                 330                 335

Trp Ser Arg Asp Leu Gly Ile Asp Thr Gly Gln Ala Ala Tyr Leu Asn
            340                 345                 350

Ala Asn Ile Arg Tyr
```

355

(2) INFORMATION FOR SEQ ID NO: 37:

(i) SEQUENCE CHARACTERISTICS:
(A) LENGTH: 1073 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: 196F3

(xi) SEQUENCE DESCRIPTION: SEQ ID NO: 37:

```
TGGGTTACNT GGGTATTAYT TTCAGGATAC TAAATTTCAA CAACTTGCTT TAATGGCACA     60

TAGACAAGCC TCAGATTTAG AAATAAACAA AAATGAMGTC AAGGATTTAC TATCAAAGGA    120

TCAACAACAC ATTCAAGCAG TGAGATGGAT GGGCTATATT CAGCCACCTC AAACAGGAGA    180

TTATGTATTG TCAACTTCAT CCGACCAACA GGTCTTCACC GAACTCNATG GAAAAATAAT    240

TCTCAATCAA TCTTCTATGA CCGAACCCAT TCGATTAGAA AAAGATAAAC AATATAMAAT    300

TAGAATTGAA TATGTATCAK AAAGTAAAAC AGAAAAAGAG ACGCTCCTAG ACTTTCAACT    360

CAACTGGTCG ATTTCAGGTG CTACGGTAGA ACCAATTCCA GATAATGCTT TTCAGTTACC    420

AGATCTTTCT CGGGAACAAG NTAAAGATAA AATCATCCCT GAAACAAGTT TATTGCAGGA    480

TCAAGGAGAA GGGAAACAAG TATCTCGAAG TAAAAGATCT CTAGCTGTGA ATCCTCTACA    540

CGATACAGAT GATGATGGGA TTTACGATGA ATGGGAAACA AGCGGCTATA CGATTCAAAG    600

ACAATTGGCA GTAAGATGGA ACGATTCTAT GAAGGATCAA GGCTATACCA AATATGTGTC    660

TAATCCTTAT AAGTCTCATA CTGTAGGAGA TCCATACACA GACTGGGAAA AAGCAGCTGG    720

ACGTATCGAC CAAGCTGTGA AAATAGAAGC CAGAAACCCA TTAGTTGCAG CATATCCAAC    780

AGTTGGCGTA CATATGGAAA GACTGATTGT CTCTGAAAAA CAAAATATAG CAACAGGACT    840

GGGAAAAACA GTATCTGCGT CTACATCTGC AAGTAATACA GCGGGGATTA CAGCGGGAAT    900

CGATGCAACG GTTGGTGCCT CTTTACTTGG ACCTTCGGGA AGTGTCACCG CCCATTTTTC    960

TTATACGGGT TCGAGTACAT CCACTGTTGA AAATAGCTCG AGTAATAATT GGAGTCAAGA   1020

TCTTGGTATT GATACCAGCC AATCTGCGTA CTTAAATGCC AATGTAAGAT ATA          1073
```

(2) INFORMATION FOR SEQ ID NO: 38:

(i) SEQUENCE CHARACTERISTICS:
(A) LENGTH: 357 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: 196F3

(xi) SEQUENCE DESCRIPTION: SEQ ID NO: 38:

```
Gly Leu Xaa Gly Tyr Xaa Phe Gln Asp Thr Lys Phe Gln Gln Leu Ala
1               5                   10                  15

Leu Met Ala His Arg Gln Ala Ser Asp Leu Glu Ile Asn Lys Asn Xaa
            20                  25                  30

Val Lys Asp Leu Leu Ser Lys Asp Gln Gln His Ile Gln Ala Val Arg
        35                  40                  45
```

-continued

```
Trp Met Gly Tyr Ile Gln Pro Pro Gln Thr Gly Asp Tyr Val Leu Ser
    50                  55                  60

Thr Ser Ser Asp Gln Gln Val Phe Thr Glu Leu Xaa Gly Lys Ile Ile
65                  70                  75                  80

Leu Asn Gln Ser Ser Met Thr Glu Pro Ile Arg Leu Glu Lys Asp Lys
                85                  90                  95

Gln Tyr Xaa Ile Arg Ile Glu Tyr Val Ser Xaa Ser Lys Thr Glu Lys
            100                 105                 110

Glu Thr Leu Leu Asp Phe Gln Leu Asn Trp Ser Ile Ser Gly Ala Thr
        115                 120                 125

Val Glu Pro Ile Pro Asp Asn Ala Phe Gln Leu Pro Asp Leu Ser Arg
    130                 135                 140

Glu Gln Xaa Lys Asp Lys Ile Ile Pro Glu Thr Ser Leu Leu Gln Asp
145                 150                 155                 160

Gln Gly Glu Gly Lys Gln Val Ser Arg Ser Lys Arg Ser Leu Ala Val
                165                 170                 175

Asn Pro Leu His Asp Thr Asp Asp Asp Gly Ile Tyr Asp Glu Trp Glu
            180                 185                 190

Thr Ser Gly Tyr Thr Ile Gln Arg Gln Leu Ala Val Arg Trp Asn Asp
        195                 200                 205

Ser Met Lys Asp Gln Gly Tyr Thr Lys Tyr Val Ser Asn Pro Tyr Lys
    210                 215                 220

Ser His Thr Val Gly Asp Pro Tyr Thr Asp Trp Glu Lys Ala Ala Gly
225                 230                 235                 240

Arg Ile Asp Gln Ala Val Lys Ile Glu Ala Arg Asn Pro Leu Val Ala
                245                 250                 255

Ala Tyr Pro Thr Val Gly Val His Met Glu Arg Leu Ile Val Ser Glu
            260                 265                 270

Lys Gln Asn Ile Ala Thr Gly Leu Gly Lys Thr Val Ser Ala Ser Thr
        275                 280                 285

Ser Ala Ser Asn Thr Ala Gly Ile Thr Ala Gly Ile Asp Ala Thr Val
    290                 295                 300

Gly Ala Ser Leu Leu Gly Pro Ser Gly Ser Val Thr Ala His Phe Ser
305                 310                 315                 320

Tyr Thr Gly Ser Ser Thr Ser Thr Val Glu Asn Ser Ser Ser Asn Asn
                325                 330                 335

Trp Ser Gln Asp Leu Gly Ile Asp Thr Ser Gln Ser Ala Tyr Leu Asn
            340                 345                 350

Ala Asn Val Arg Tyr
        355
```

(2) INFORMATION FOR SEQ ID NO: 39:

(i) SEQUENCE CHARACTERISTICS:
(A) LENGTH: 1073 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: 196J4

(xi) SEQUENCE DESCRIPTION: SEQ ID NO: 39:

```
TGGGTTAATT GGGTATTATT TCCAGGATCA AAAGTTTCAA CAACTTGCTT TAATGGCACA     60

TAGACAAGCT TCTAATTTAA ACATACCAAA AAATGAAGTG AAACAGTTAT TATCCGAAGA    120
```

-continued

```
TCAACAACAT ATTCAATCCG TTAGGTGGAT CGGATATATC AAATCACCTC AAACGGGAGA    180

TTATATATTG TCAACTTCAG CCGATCGACA TGTCGTAATT GAACTTGACG GAAAAACCAT    240

TCTTAATCAA TCTTCTATGA CAGCACCCAT TCAATTAGAA AAAGATAAAC TTTATAAAAT    300

TAGAATTGAA TATGTCCCAG AAGATACAAA AGGACAGGAA AACCTCTTTG ACTTTCAACT    360

GAATTGGTCA ATTTCAGGAG ATAAGGTAGA ACCAATTCCG GAGAATGCAT TTCTGTTGCC    420

AGACTTTTCT CATAAACAAG ATCAAGAGAA AATCATCCCT GAAGCAAGTT TATTCCAGGA    480

ACAAGAAGAT GCAAACAAAG TCTCTCGAAA TAAACGATCC ATAGCTACAG GTTCTCTGTA    540

TGATACAGAT GATGATGCTA TTTATGATGA ATGGGAAACA GAAGGATACA CGATACAACG    600

TCAAATAGCG GTGAAATGGG ACGATTCTAT GAAGGAGCGA GGTTATACCA AGTATGTGTC    660

TAACCCCTAT AATTCGCATA CAGTAGGAGA TCCCTACACA GATTGGGAAA AAGCGGCTGG    720

ACGCATTGAT CAGGCAATCA AAGTAGAAGC TAGGAATCCA TTAGTTGCAG CCTATCCAAC    780

AGTTGGTGTA CATATGGAAA AACTGATTGT TTCTGAGAAA CAAAATATAT CAACTGGGGT    840

TGGAAAAACA GTATCTGCGG CTATGTCCAC TGGTAATACC GCAGCGATTA CGGCAGGAAT    900

TGATGCGACC GCCGGGGCAT CTTTACTTGG ACCTTCTGGA AGTGTGACGG CTCATTTTTC    960

TTATACAGGG TCTAGTACAT CTACAATTGA AAATAGTTCA AGCAATAATT GGAGTAAAGA   1020

TCTGGGAATC GATACGGGGC AATCTGCTTA TTTAAATGCC AATGTACGAT ATA          1073
```

(2) INFORMATION FOR SEQ ID NO: 40:

(i) SEQUENCE CHARACTERISTICS:
(A) LENGTH: 357 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: 196J4

(xi) SEQUENCE DESCRIPTION: SEQ ID NO: 40:

```
Gly Leu Ile Gly Tyr Tyr Phe Gln Asp Gln Lys Phe Gln Gln Leu Ala
1               5                   10                  15

Leu Met Ala His Arg Gln Ala Ser Asn Leu Asn Ile Pro Lys Asn Glu
            20                  25                  30

Val Lys Gln Leu Leu Ser Glu Asp Gln Gln His Ile Gln Ser Val Arg
        35                  40                  45

Trp Ile Gly Tyr Ile Lys Ser Pro Gln Thr Gly Asp Tyr Ile Leu Ser
    50                  55                  60

Thr Ser Ala Asp Arg His Val Val Ile Glu Leu Asp Gly Lys Thr Ile
65                  70                  75                  80

Leu Asn Gln Ser Ser Met Thr Ala Pro Ile Gln Leu Glu Lys Asp Lys
                85                  90                  95

Leu Tyr Lys Ile Arg Ile Glu Tyr Val Pro Glu Asp Thr Lys Gly Gln
            100                 105                 110

Glu Asn Leu Phe Asp Phe Gln Leu Asn Trp Ser Ile Ser Gly Asp Lys
        115                 120                 125

Val Glu Pro Ile Pro Glu Asn Ala Phe Leu Leu Pro Asp Phe Ser His
    130                 135                 140

Lys Gln Asp Gln Glu Lys Ile Ile Pro Glu Ala Ser Leu Phe Gln Glu
145                 150                 155                 160
```

-continued

```
Gln Glu Asp Ala Asn Lys Val Ser Arg Asn Lys Arg Ser Ile Ala Thr
                165                 170                 175

Gly Ser Leu Tyr Asp Thr Asp Asp Asp Ala Ile Tyr Asp Glu Trp Glu
            180                 185                 190

Thr Glu Gly Tyr Thr Ile Gln Arg Gln Ile Ala Val Lys Trp Asp Asp
        195                 200                 205

Ser Met Lys Glu Arg Gly Tyr Thr Lys Tyr Val Ser Asn Pro Tyr Asn
    210                 215                 220

Ser His Thr Val Gly Asp Pro Tyr Thr Asp Trp Glu Lys Ala Ala Gly
225                 230                 235                 240

Arg Ile Asp Gln Ala Ile Lys Val Glu Ala Arg Asn Pro Leu Val Ala
                245                 250                 255

Ala Tyr Pro Thr Val Gly Val His Met Glu Lys Leu Ile Val Ser Glu
            260                 265                 270

Lys Gln Asn Ile Ser Thr Gly Val Gly Lys Thr Val Ser Ala Ala Met
        275                 280                 285

Ser Thr Gly Asn Thr Ala Ala Ile Thr Ala Gly Ile Asp Ala Thr Ala
    290                 295                 300

Gly Ala Ser Leu Leu Gly Pro Ser Gly Ser Val Thr Ala His Phe Ser
305                 310                 315                 320

Tyr Thr Gly Ser Ser Thr Ser Thr Ile Glu Asn Ser Ser Ser Asn Asn
                325                 330                 335

Trp Ser Lys Asp Leu Gly Ile Asp Thr Gly Gln Ser Ala Tyr Leu Asn
            340                 345                 350

Ala Asn Val Arg Tyr
        355
```

(2) INFORMATION FOR SEQ ID NO: 41:

(i) SEQUENCE CHARACTERISTICS:
(A) LENGTH: 1046 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: 197T1

(xi) SEQUENCE DESCRIPTION: SEQ ID NO: 41:

```
TGGATTAATT GGGTATTATT TTAAAGGAAA AGATTTTAAT AATCTTACTA TATTTGCTCC     60

AACACGTGAG AATACTCTTA TTTATGATTT AGAAACAGCG AATTCTTTAT TAGATAAGCA    120

ACAACAAACC TATCAATCTA TTCGTTGGAT CGGTTTAATA AAAAGCAAAA AAGCTGGAGA    180

TTTTACCTTT CAATTATCGG ATGATGAGCA TGCTATTATA GAAATCGATG GGAAAGTTAT    240

TTCGCAAAAA GGCCAAAAGA AACAAGTTGT TCATTTAGAA AAAGATAAAT TAGTTCCCAT    300

CAAAATTGAA TATCAATCTG ATAAAGCGTT AAACCCAGAC AGTCAAATGT TTAAAGAATT    360

GAAATTATTT AAAATAAATA GTCAAAAACA ATCTCAGCAA GTGCAACAAG ACGAATTGAG    420

AAATCCTGAA TTTGGTAAAG AAAAAACTCA AACATATTTA AAGAAAGCAT CGAAAAGCAG    480

CTTGTTTAGC AATAAAAGTA AACGAGATAT AGATGAAGAT ATAGATGAGG ATACAGATAC    540

AGATGGAGAT GCCATTCCTG ATGTATGGGA AGAAAATGGG TATACCATCA AAGGAAGAGT    600

AGCTGTTAAA TGGGACGAAG GATTAGCTGA TAAGGGATAT AAAAAGTTTG TTTCCAATCC    660

TTTTAGACAG CACACTGCTG GTGACCCCTA TAGTGACTAT GAAAAGGCAT CAAAAGATTT    720
```

-continued

```
GGATTTATCT AATGCAAAAG AAACATTTAA TCCATTGGTG GCTGCTTTTC CAAGTGTCAA    780

TGTTAGCTTG GAAAATGTCA CCATATCAAA AGATGAAAAT AAAACTGCTG AAATTGCGTC    840

TACTTCATCG AATAATTGGT CCTATACAAA TACAGAGGGG GCATCTATTG AAGCTGGAAT    900

TGGACCAGAA GGTTTGTTGT CTTTTGGAGT AAGTGCCAAT TATCAACATT CTGAAACAGT    960

GGCCAAAGAG TGGGGTACAA CTAAGGGAGA CGCAACACAA TATAATACAG CTTCAGCAGG   1020

ATATCTAAAT GCCAATGTAC GATATA                                        1046
```

(2) INFORMATION FOR SEQ ID NO: 42:

(i) SEQUENCE CHARACTERISTICS:
(A) LENGTH: 348 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: 197T1

(xi) SEQUENCE DESCRIPTION: SEQ ID NO: 42:

```
Gly Leu Ile Gly Tyr Tyr Phe Lys Gly Lys Asp Phe Asn Asn Leu Thr
1               5                   10                  15

Ile Phe Ala Pro Thr Arg Glu Asn Thr Leu Ile Tyr Asp Leu Glu Thr
            20                  25                  30

Ala Asn Ser Leu Leu Asp Lys Gln Gln Gln Thr Tyr Gln Ser Ile Arg
        35                  40                  45

Trp Ile Gly Leu Ile Lys Ser Lys Lys Ala Gly Asp Phe Thr Phe Gln
    50                  55                  60

Leu Ser Asp Asp Glu His Ala Ile Ile Glu Ile Asp Gly Lys Val Ile
65                  70                  75                  80

Ser Gln Lys Gly Gln Lys Lys Gln Val Val His Leu Glu Lys Asp Lys
                85                  90                  95

Leu Val Pro Ile Lys Ile Glu Tyr Gln Ser Asp Lys Ala Leu Asn Pro
            100                 105                 110

Asp Ser Gln Met Phe Lys Glu Leu Lys Leu Phe Lys Ile Asn Ser Gln
        115                 120                 125

Lys Gln Ser Gln Gln Val Gln Gln Asp Glu Leu Arg Asn Pro Glu Phe
    130                 135                 140

Gly Lys Glu Lys Thr Gln Thr Tyr Leu Lys Lys Ala Ser Lys Ser Ser
145                 150                 155                 160

Leu Phe Ser Asn Lys Ser Lys Arg Asp Ile Asp Glu Asp Ile Asp Glu
                165                 170                 175

Asp Thr Asp Thr Asp Gly Asp Ala Ile Pro Asp Val Trp Glu Glu Asn
            180                 185                 190

Gly Tyr Thr Ile Lys Gly Arg Val Ala Val Lys Trp Asp Glu Gly Leu
        195                 200                 205

Ala Asp Lys Gly Tyr Lys Lys Phe Val Ser Asn Pro Phe Arg Gln His
    210                 215                 220

Thr Ala Gly Asp Pro Tyr Ser Asp Tyr Glu Lys Ala Ser Lys Asp Leu
225                 230                 235                 240

Asp Leu Ser Asn Ala Lys Glu Thr Phe Asn Pro Leu Val Ala Ala Phe
                245                 250                 255

Pro Ser Val Asn Val Ser Leu Glu Asn Val Thr Ile Ser Lys Asp Glu
            260                 265                 270
```

-continued

```
Asn Lys Thr Ala Glu Ile Ala Ser Thr Ser Ser Asn Asn Trp Ser Tyr
        275                 280                 285

Thr Asn Thr Glu Gly Ala Ser Ile Glu Ala Gly Ile Gly Pro Glu Gly
    290                 295                 300

Leu Leu Ser Phe Gly Val Ser Ala Asn Tyr Gln His Ser Glu Thr Val
305                 310                 315                 320

Ala Lys Glu Trp Gly Thr Thr Lys Gly Asp Ala Thr Gln Tyr Asn Thr
                325                 330                 335

Ala Ser Ala Gly Tyr Leu Asn Ala Asn Val Arg Tyr
            340                 345
```

(2) INFORMATION FOR SEQ ID NO: 43:

(i) SEQUENCE CHARACTERISTICS:
(A) LENGTH: 1002 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: 197U2

(xi) SEQUENCE DESCRIPTION: SEQ ID NO: 43:

```
TGGGTTAATT GGGTATTATT TTACGGATGA GCAGCATAAG GAAGTAGCTT TTAYTCAATT     60

AGGTGAAAAA AMTACATTAG CAGATTCAGC GAAAATGAAG AAAAACGACA AAAAGATTCT    120

TTCAGCGCAA TGGATTGGWA ATATACAGGT ACCTCAAACA GGGGAATATA CGTTTTCCAC    180

CTCTTCTGAT AAAGATACTA TTTTAAAACT CAATGGGGAA ACGATTATTC AAAAATCTAA    240

TATGGAGAAA CCCATATATT TAGAAAAAGA TAAAGTATAC GAAATTCAAA TCGAGCATAA    300

CAACCCGAAT AGTGAGAAAA CTTTACGATT ATCTTGGAAA ATGGGGGGCA CCAATTCAGA    360

GCTCATCCCA GAAAAATACA TTCTGTCTCC CGATTTTTCT AAAATAGCAG ATCAAGAAAA    420

TGARAAAAAA GACGCATCGA GACATTTATT ATTTACTAAG GATGAATTGA AAGATTCTGA    480

TAAGGACCTT ATCCCAGATG AATTTGAAAA AAATGGGTAT ACATTCAATG GGATTCAAAT    540

TGTTCCTTGG GATGAATCTC TTCAAGAACA GGGCTTTAAA AAATATATTT CCAATCCATA    600

TCAATCGCGT ACAGCGCAGG ATCCATATAC AGATTTTGAA AAAGTAACCG GATATATGCC    660

TGCCGAAACA CAACTGGAAA CGCGTGACCC TTTAGTTGCG GCTTATCCGG CTGTAGGGGT    720

TACGATGGAA CAGTTTATTT TCTCTAAAAA TGATAATGTG CAGGAATCTA ATGGTGGAGG    780

AACTTCAAAA AGTATGACAG AAAGTTCTGA AACGACTTAC TCTGTTGAGA TAGGAGGGAA    840

ATTTACATTG AATCCATTCG CACTGGCGGA AATTTCTCCT AAATATTCTC ACAGTTGGAA    900

AAATGGAGCA TCTACAACAG AGGGAGAAAG TACTTCCTGG AGCTCACAAA TTGGTATTAA    960

CACGGCTGAA CGCGCGTTTT TTAAATGCCA ATATTCGATA TA                      1002
```

(2) INFORMATION FOR SEQ ID NO: 44:

(i) SEQUENCE CHARACTERISTICS:
(A) LENGTH: 333 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: 197U2

(xi) SEQUENCE DESCRIPTION: SEQ ID NO: 44:

```
Gly Leu Ile Gly Tyr Tyr Phe Thr Asp Glu Gln His Lys Glu Val Ala
1               5                   10                  15

Phe Xaa Gln Leu Gly Glu Lys Xaa Thr Leu Ala Asp Ser Ala Lys Met
            20                  25                  30

Lys Lys Asn Asp Lys Lys Ile Leu Ser Ala Gln Trp Ile Xaa Asn Ile
        35                  40                  45

Gln Val Pro Gln Thr Gly Glu Tyr Thr Phe Ser Thr Ser Ser Asp Lys
    50                  55                  60

Asp Thr Ile Leu Lys Leu Asn Gly Glu Thr Ile Ile Gln Lys Ser Asn
65                  70                  75                  80

Met Glu Lys Pro Ile Tyr Leu Glu Lys Asp Lys Val Tyr Glu Ile Gln
                85                  90                  95

Ile Glu His Asn Asn Pro Asn Ser Glu Lys Thr Leu Arg Leu Ser Trp
            100                 105                 110

Lys Met Gly Gly Thr Asn Ser Glu Leu Ile Pro Glu Lys Tyr Ile Leu
        115                 120                 125

Ser Pro Asp Phe Ser Lys Ile Ala Asp Gln Glu Asn Xaa Lys Lys Asp
    130                 135                 140

Ala Ser Arg His Leu Leu Phe Thr Lys Asp Glu Leu Lys Asp Ser Asp
145                 150                 155                 160

Lys Asp Leu Ile Pro Asp Glu Phe Glu Lys Asn Gly Tyr Thr Phe Asn
                165                 170                 175

Gly Ile Gln Ile Val Pro Trp Asp Glu Ser Leu Gln Glu Gln Gly Phe
            180                 185                 190

Lys Lys Tyr Ile Ser Asn Pro Tyr Gln Ser Arg Thr Ala Gln Asp Pro
        195                 200                 205

Tyr Thr Asp Phe Glu Lys Val Thr Gly Tyr Met Pro Ala Glu Thr Gln
    210                 215                 220

Leu Glu Thr Arg Asp Pro Leu Val Ala Ala Tyr Pro Ala Val Gly Val
225                 230                 235                 240

Thr Met Glu Gln Phe Ile Phe Ser Lys Asn Asp Asn Val Gln Glu Ser
                245                 250                 255

Asn Gly Gly Gly Thr Ser Lys Ser Met Thr Glu Ser Ser Glu Thr Thr
            260                 265                 270

Tyr Ser Val Glu Ile Gly Gly Lys Phe Thr Leu Asn Pro Phe Ala Leu
        275                 280                 285

Ala Glu Ile Ser Pro Lys Tyr Ser His Ser Trp Lys Asn Gly Ala Ser
    290                 295                 300

Thr Thr Glu Gly Glu Ser Thr Ser Trp Ser Ser Gln Ile Gly Ile Asn
305                 310                 315                 320

Thr Ala Glu Arg Ala Phe Phe Lys Cys Gln Tyr Ser Ile
                325                 330
```

(2) INFORMATION FOR SEQ ID NO: 45:

(i) SEQUENCE CHARACTERISTICS:
(A) LENGTH: 1073 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: 202E1

-continued (xi) SEQUENCE DESCRIPTION: SEQ ID NO: 45:

```
TGGGTTAATT GGGTACTATT TTCAGGATCA AAAGTTTCAA CAACTCGCTT TGATGGCACA     60
TAGACAAGCT TCAGATTTAG AAATACCTAA AAATGAAGTG AAGGATATAT TATCTAAAGA    120
TCAACAACAT ATTCAATCAG TGAGATGGAG GGGGTATATT AAGCCACCTC AAACAGGAGA    180
CTATATATTG TCAACCTCAT CCGACCAACA GGTCGTGATT GAACTCGATG GAAAAAACAT    240
TGTCAATCAA ACTTCTATGA CAGAACCAAT TCAACTCGAA AAAGATAAAC TCTATAAAAT    300
TAGAATTGAA TATGTCCCAG GAGATACAAA AGGACAAGAG AGCCTCCTTG ACTTTCAACT    360
TAACTGGTCA ATTTCAGGAG ATACGGTGGA ACCAATTCCG GAGAATGCAT TTCTGTTACC    420
AGACTTTTCT CATCAACAAG ATCAAGAGAA ACTCATCCCT GAAATCAGTC TATTTCAGGA    480
ACAAGGAGAT GAGAAAAAAG TATCTCGTAG TAAGAGGTCT TTAGCTACAA ACCCTCTCCT    540
TGATACAGAT GATGATGGTA TTTATGATGA ATGGGAAACG GAAGGATACA CAATACAGGG    600
ACAACTAGCG GTGAAATGGG ACGATTCTAT GAAGGAGCGA GGTTATACTA AGTATGTGTC    660
TAACCCTTAC AAGGCTCATA CAGTAGGAGA TCCCTACACA GATTGGGAAA AAGCGGCTGG    720
CCGTATCGAT AACGCTGTCA AAGCAGAAGC TAGGAATCCT TTAGTCGCGG CCTATCCAAC    780
TGTTGGTGTA CATATGGAAA GACTAATTGT CTCCGAAAAA CAAAATATAT CAACAGGACT    840
TGGAAAAACC GTATCTGTGT CTATGTCCGC AAGCAATACC GCAGCGATTA CGGCAGGAAT    900
TAATGCAACA GCCGGTGCCT CTTTACTTGG GCCATCTGGA AACGTCACGG CTCATTTTTC    960
TTATACAGGA TCTAGTACAT CCACTGTTGA AAATAGCTCA AGTAATAATT GGAGTCAAGA   1020
TCTTGGAATC GATACGGGAC AATCTGCGTA TTTAAATGCC AATGTAAGAT ATA          1073
```

(2) INFORMATION FOR SEQ ID NO: 46:

(i) SEQUENCE CHARACTERISTICS:
(A) LENGTH: 357 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: 202E1

(xi) SEQUENCE DESCRIPTION: SEQ ID NO: 46:

```
Gly Leu Ile Gly Tyr Tyr Phe Gln Asp Gln Lys Phe Gln Gln Leu Ala
1               5                   10                  15

Leu Met Ala His Arg Gln Ala Ser Asp Leu Glu Ile Pro Lys Asn Glu
            20                  25                  30

Val Lys Asp Ile Leu Ser Lys Asp Gln Gln His Ile Gln Ser Val Arg
        35                  40                  45

Trp Arg Gly Tyr Ile Lys Pro Pro Gln Thr Gly Asp Tyr Ile Leu Ser
    50                  55                  60

Thr Ser Ser Asp Gln Gln Val Val Ile Glu Leu Asp Gly Lys Asn Ile
65                  70                  75                  80

Val Asn Gln Thr Ser Met Thr Glu Pro Ile Gln Leu Glu Lys Asp Lys
                85                  90                  95

Leu Tyr Lys Ile Arg Ile Glu Tyr Val Pro Gly Asp Thr Lys Gly Gln
            100                 105                 110

Glu Ser Leu Leu Asp Phe Gln Leu Asn Trp Ser Ile Ser Gly Asp Thr
        115                 120                 125

Val Glu Pro Ile Pro Glu Asn Ala Phe Leu Leu Pro Asp Phe Ser His
```

-continued

```
    130                 135                 140

Gln Gln Asp Gln Glu Lys Leu Ile Pro Glu Ile Ser Leu Phe Gln Glu
145                 150                 155                 160

Gln Gly Asp Glu Lys Lys Val Ser Arg Ser Lys Arg Ser Leu Ala Thr
                165                 170                 175

Asn Pro Leu Leu Asp Thr Asp Asp Asp Gly Ile Tyr Asp Glu Trp Glu
            180                 185                 190

Thr Glu Gly Tyr Thr Ile Gln Gly Gln Leu Ala Val Lys Trp Asp Asp
        195                 200                 205

Ser Met Lys Glu Arg Gly Tyr Thr Lys Tyr Val Ser Asn Pro Tyr Lys
    210                 215                 220

Ala His Thr Val Gly Asp Pro Tyr Thr Asp Trp Glu Lys Ala Ala Gly
225                 230                 235                 240

Arg Ile Asp Asn Ala Val Lys Ala Glu Ala Arg Asn Pro Leu Val Ala
                245                 250                 255

Ala Tyr Pro Thr Val Gly Val His Met Glu Arg Leu Ile Val Ser Glu
            260                 265                 270

Lys Gln Asn Ile Ser Thr Gly Leu Gly Lys Thr Val Ser Val Ser Met
        275                 280                 285

Ser Ala Ser Asn Thr Ala Ala Ile Thr Ala Gly Ile Asn Ala Thr Ala
    290                 295                 300

Gly Ala Ser Leu Leu Gly Pro Ser Gly Asn Val Thr Ala His Phe Ser
305                 310                 315                 320

Tyr Thr Gly Ser Ser Thr Ser Thr Val Glu Asn Ser Ser Ser Asn Asn
                325                 330                 335

Trp Ser Gln Asp Leu Gly Ile Asp Thr Gly Gln Ser Ala Tyr Leu Asn
            340                 345                  350

Ala Asn Val Arg Tyr
        355
```

(2) INFORMATION FOR SEQ ID NO: 47:

(i) SEQUENCE CHARACTERISTICS:
(A) LENGTH: 967 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: KB33

(xi) SEQUENCE DESCRIPTION: SEQ ID NO: 47:

```
TGGATTACTT GGGTACTATT TTGAAGAACC AAACTTTAAT GACCTTCTAT TAATCACACA     60

AAAAAACAAC AGTAATTTAT CTCTAGAAAA AGAACATATT TCATCGTTAT CTAGTATTAG    120

AAATAAAGGC ATTCAATCTG CTAGATGGTT AGGTTTTTTA AAACCAAAGC AAACGGATGA    180

ATATGTTTTT TTTAGTCCTT CCAACCATGA AATCATGATT CAAATCGATA ACAAAATTAT    240

TGTAATGGGT AGAAAAATTA TGTTAGAAGA AGGAAAGGTA TATCCAATTC GAATTGAATG    300

CCGCTTTGAA AAAACAAATA ATCTAGATAT AAACTGCGAA CTACTTTGGA CGCATTCTGA    360

TACAAAAGAA ATCATTTCTC AAAACTGTTT GCTGGCACCT GATTATCATA ATACAGAATT    420

TTACCCAAAA ACAAATTTAT TTGGGGATGT ATCTACTACG ACTAGTGATA CTGATAATGA    480

TGGAATACCA GATGACTGGG AAATTAATGG TTATACGTTT GATGGTACAA ATATAATTCA    540

ATGGAATCCT GCTTATGAAG GGTTATATAC TAAATATATT TCTAACCCTA AACAAGCAAG    600
```

```
TACAGTAGGT GATCCATATA CAGATTTAGA GAACGTMCAA AGCTAAAKGG ATCAAAGAAS    660

CARGAAAYCC TTKTAGCAGA AGCTWATCCG AAAAATTGGA BTTAGCATGG AAGAATTACT    720

CRTCTCTKTA WAARTGKTGA TKTWTTCAAA TGCTCAAGAA AATKACTACT TACTTCTAGT    780

AGRACAGAAG GCACTTCASG TAGYGCAGGC ATTGAGGGAG GAGCAGAAGG AAAAAAACCT    840

ACAGGATTGG TTTCAGCCTC CTTTTCGCAT TCATCTTCAA CAACAAACAC AACGGAACAA    900

ATGAATGGAA CAATGATTCA TCTTGATACA GGAGAATCAG CGTATTTAAA TGCCAATGTA    960

AGATATA                                                              967
```

(2) INFORMATION FOR SEQ ID NO: 48:

(i) SEQUENCE CHARACTERISTICS:
(A) LENGTH: 972 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: KB38

(xi) SEQUENCE DESCRIPTION: SEQ ID NO: 48:

```
TGGATTACTT GGGTATTATT TTGAAGAACC AAACTTTAAT AACCTTCTAT TAATCACACA     60

AAAAAACAAC AGTAATTTAT CTCTAGAAAA AGAACATATT TCATCGTTAT CTAGTATTAG    120

AAATAAAGGC ATTCAATCTG CTAGATGGTT AGGTTTTTTA AAACCAGAGC AAACGGATGA    180

ATATGTTTTT TTTAGTCCTT CCAACCATGA AATTATGATT CAAATCGATA ACAAAATTAT    240

TGTAATGGGT AGAAAAATTA TGTTAGAAAA AGGAAAGGTA TATCCAATTC GAATTGAATG    300

CCGCTTTGAA AAAACAAATA ATATAGATAT AAACTGCGAA CTACTTTGGA CGCACTCTGA    360

TACAAAAGAA ATCATTTCTC AAAACTTTTT GCTGGCACCT GATTATAACA ATACAGAATT    420

TTATCCAAAA ACAAATTTAT TTGGAGATGT ATCTACTACG ACTWAGTGAT ACTGATAATG    480

ATGGAATACC AGATGACTGG GAAATTAATG GTTATACCTT TGATGGTACA AATATAATTC    540

AGTGGAATTC TGCTTATGAA GGGTTATATA CTAAATATGT TTCTAATCCT AAACAAGCAA    600

GTACAGTAGG TGATCCATAT ACAGATTTAG AGAAAGTAAC AGCTCAAATG GATCGAGCAA    660

CCTCTCTAGA AGCAAGGAAT CCTTTAGTAG CAGCTTATCC AAAAATTGGA GTTAGCATGG    720

AAGAATTACT CATCTCTTTA AATGTTGATT TTTCAAATGC TCAAGAAAAT ACTACTTCTT    780

CTAGTAGAAC AGAAGGCACT TCACGTAGCG CAGGCATTGA GGGAGGAGCA GAAGGAAAAA    840

AACCTACAGG ATTGGTTTCA GCCTCCTTTT CGCATTCATC TTCAACAACA AACACAACGG    900

AACAAATGAA TGGAACAATG ATTCATCTTG ATACAGGAGA ATCAGCGTAT TTAAATGCCA    960

ATGTAAGATA TA                                                        972
```

(2) INFORMATION FOR SEQ ID NO: 49:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 49:

```
CTTGAYTTTA AARATGATRT A                                               21
```

(2) INFORMATION FOR SEQ ID NO: 50:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 50:

AATRGCSWAT AAATAMGCAC C 21

(2) INFORMATION FOR SEQ ID NO: 51:

(i) SEQUENCE CHARACTERISTICS:
(A) LENGTH: 1341 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: PS177C8

(xi) SEQUENCE DESCRIPTION: SEQ ID NO: 51:

ATGTTTATGG TTTCTAAAAA ATTACAAGTA GTTACTAAAA CTGTATTGCT TAGTACAGTT 60

TTCTCTATAT CTTTATTAAA TAATGAAGTG ATAAAAGCTG AACAATTAAA TATAAATTCT 120

CAAAGTAAAT ATACTAACTT GCAAAATCTA AAAATCACTG ACAAGGTAGA GGATTTTAAA 180

GAAGATAAGG AAAAAGCGAA AGAATGGGGG AAAGAAAAAG AAAAAGAGTG GAAACTAACT 240

GCTACTGAAA AAGGAAAAAT GAATAATTTT TTAGATAATA AAAATGATAT AAAGACAAAT 300

TATAAAGAAA TTACTTTTTC TATGGCAGGC TCATTTGAAG ATGAAATAAA AGATTTAAAA 360

GAAATTGATA AGATGTTTGA TAAAACCAAT CTATCAAATT CTATTATCAC CTATAAAAAT 420

GTGGAACCGA CAACAATTGG ATTTAATAAA TCTTTAACAG AAGGTAATAC GATTAATTCT 480

GATGCAATGG CACAGTTTAA AGAACAATTT TTAGATAGGG ATATTAAGTT TGATAGTTAT 540

CTAGATACGC ATTTAACTGC TCAACAAGTT TCCAGTAAAG AAAGAGTTAT TTTGAAGGTT 600

ACGGTTCCGA GTGGGAAAGG TTCTACTACT CCAACAAAAG CAGGTGTCAT TTTAAATAAT 660

AGTGAATACA AAATGCTCAT TGATAATGGG TATATGGTCC ATGTAGATAA GGTATCAAAA 720

GTGGTGAAAA AAGGGGTGGA GTGCTTACAA ATTGAAGGGA CTTTAAAAAA GAGTCTTGAC 780

TTTAAAAATG ATATAAATGC TGAAGCGCAT AGCTGGGGTA TGAAGAATTA TGAAGAGTGG 840

GCTAAAGATT TAACCGATTC GCAAAGGGAA GCTTTAGATG GGTATGCTAG GCAAGATTAT 900

AAAGAAATCA ATAATTATTT AAGAAATCAA GGCGGAAGTG GAAATGAAAA ACTAGATGCT 960

CAAATAAAAA ATATTTCTGA TGCTTTAGGG AAGAAACCAA TACCGGAAAA TATTACTGTG 1020

TATAGATGGT GTGGCATGCC GGAATTTGGT TATCAAATTA GTGATCCGTT ACCTTCTTTA 1080

AAAGATTTTG AAGAACAATT TTTAAATACA ATCAAAGAAG ACAAAGGATA TATGAGTACA 1140

AGCTTATCGA GTGAACGTCT TGCAGCTTTT GGATCTAGAA AAATTATATT ACGATTACAA 1200

GTTCCGAAAG GAAGTACGGG TGCGTATTTA AGTGCCATTG GTGGATTTGC AAGTGAAAAA 1260

GAGATCCTAC TTGATAAAGA TAGTAAATAT CATATTGATA AAGTAACAGA GGTAATTATT 1320

AAGGTGTTAA GCGATATGTA G 1341

(2) INFORMATION FOR SEQ ID NO: 52:

(i) SEQUENCE CHARACTERISTICS:
(A) LENGTH: 446 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: PS177C8

(xi) SEQUENCE DESCRIPTION: SEQ ID NO: 52:

```
Met Phe Met Val Ser Lys Lys Leu Gln Val Val Thr Lys Thr Val Leu
1               5                   10                  15

Leu Ser Thr Val Phe Ser Ile Ser Leu Leu Asn Asn Glu Val Ile Lys
            20                  25                  30

Ala Glu Gln Leu Asn Ile Asn Ser Gln Ser Lys Tyr Thr Asn Leu Gln
        35                  40                  45

Asn Leu Lys Ile Thr Asp Lys Val Glu Asp Phe Lys Glu Asp Lys Glu
    50                  55                  60

Lys Ala Lys Glu Trp Gly Lys Glu Lys Glu Lys Glu Trp Lys Leu Thr
65                  70                  75                  80

Ala Thr Glu Lys Gly Lys Met Asn Asn Phe Leu Asp Asn Lys Asn Asp
                85                  90                  95

Ile Lys Thr Asn Tyr Lys Glu Ile Thr Phe Ser Met Ala Gly Ser Phe
            100                 105                 110

Glu Asp Glu Ile Lys Asp Leu Lys Glu Ile Asp Lys Met Phe Asp Lys
        115                 120                 125

Thr Asn Leu Ser Asn Ser Ile Ile Thr Tyr Lys Asn Val Glu Pro Thr
    130                 135                 140

Thr Ile Gly Phe Asn Lys Ser Leu Thr Glu Gly Asn Thr Ile Asn Ser
145                 150                 155                 160

Asp Ala Met Ala Gln Phe Lys Glu Gln Phe Leu Asp Arg Asp Ile Lys
                165                 170                 175

Phe Asp Ser Tyr Leu Asp Thr His Leu Thr Ala Gln Gln Val Ser Ser
            180                 185                 190

Lys Glu Arg Val Ile Leu Lys Val Thr Val Pro Ser Gly Lys Gly Ser
        195                 200                 205

Thr Thr Pro Thr Lys Ala Gly Val Ile Leu Asn Asn Ser Glu Tyr Lys
    210                 215                 220

Met Leu Ile Asp Asn Gly Tyr Met Val His Val Asp Lys Val Ser Lys
225                 230                 235                 240

Val Val Lys Lys Gly Val Glu Cys Leu Gln Ile Glu Gly Thr Leu Lys
                245                 250                 255

Lys Ser Leu Asp Phe Lys Asn Asp Ile Asn Ala Glu Ala His Ser Trp
            260                 265                 270

Gly Met Lys Asn Tyr Glu Glu Trp Ala Lys Asp Leu Thr Asp Ser Gln
        275                 280                 285

Arg Glu Ala Leu Asp Gly Tyr Ala Arg Gln Asp Tyr Lys Glu Ile Asn
    290                 295                 300

Asn Tyr Leu Arg Asn Gln Gly Gly Ser Gly Asn Glu Lys Leu Asp Ala
305                 310                 315                 320

Gln Ile Lys Asn Ile Ser Asp Ala Leu Gly Lys Lys Pro Ile Pro Glu
                325                 330                 335

Asn Ile Thr Val Tyr Arg Trp Cys Gly Met Pro Glu Phe Gly Tyr Gln
```

-continued

```
            340                 345                 350

Ile Ser Asp Pro Leu Pro Ser Leu Lys Asp Phe Glu Glu Gln Phe Leu
        355                 360                 365

Asn Thr Ile Lys Glu Asp Lys Gly Tyr Met Ser Thr Ser Leu Ser Ser
    370                 375                 380

Glu Arg Leu Ala Ala Phe Gly Ser Arg Lys Ile Ile Leu Arg Leu Gln
385                 390                 395                 400

Val Pro Lys Gly Ser Thr Gly Ala Tyr Leu Ser Ala Ile Gly Gly Phe
                405                 410                 415

Ala Ser Glu Lys Glu Ile Leu Leu Asp Lys Asp Ser Lys Tyr His Ile
            420                 425                 430

Asp Lys Val Thr Glu Val Ile Ile Lys Val Leu Ser Asp Met
        435                 440                 445
```

(2) INFORMATION FOR SEQ ID NO: 53:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 53:

GGATTCGTTA TCAGAAA 17

(2) INFORMATION FOR SEQ ID NO: 54:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 54:

CTGTYGCTAA CAATGTC 17

(2) INFORMATION FOR SEQ ID NO: 55:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 55:

```
Ala Asp Glu Pro Phe Asn Ala Asp
1               5
```

(2) INFORMATION FOR SEQ ID NO: 56:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 56:

GCTGATGAAC CATTTAATGC C 21

(2) INFORMATION FOR SEQ ID NO: 57:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 57:

Leu Phe Lys Val Asp Thr Lys Gln
1 5

(2) INFORMATION FOR SEQ ID NO: 58:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 58:

CTCTTTAAAG TAGATACTAA GC 22

(2) INFORMATION FOR SEQ ID NO: 59:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 59:

Pro Asp Glu Asn Leu Ser Asn Ile Glu
1 5

(2) INFORMATION FOR SEQ ID NO: 60:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 60:

GATGAGAACT TATCAAATAG TATC 24

(2) INFORMATION FOR SEQ ID NO: 61:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 61:

Ala Asn Ser Leu Leu Asp Lys Gln Gln Gln Thr Tyr
1 5 10

(2) INFORMATION FOR SEQ ID NO: 62:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 62:

CGAATTCTTT ATTAGATAAG CAACAACAAA CCT 33

(2) INFORMATION FOR SEQ ID NO: 63:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 63:

Val Ile Ser Gln Lys Gly Gln Lys
1 5

(2) INFORMATION FOR SEQ ID NO: 64:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 64:

GTTATTTCGC AAAAAGGCCA AAAG 24

(2) INFORMATION FOR SEQ ID NO: 65:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 65:

Glu Tyr Gln Ser Asp Lys Ala Leu Asn Pro Asp
1 5 10

(2) INFORMATION FOR SEQ ID NO: 66:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 66:

GAATATCAAT CTGATAAAGC GTTAAACCCA G 31

-continued (2) INFORMATION FOR SEQ ID NO: 67:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 67:

Ser Ser Leu Phe Ser Asn Lys Ser Lys
1 5

(2) INFORMATION FOR SEQ ID NO: 68:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 68:

GCAGCYTGTT TAGCAATAAA AGT 23

(2) INFORMATION FOR SEQ ID NO: 69:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 69:

Ile Lys Gly Arg Val Ala Val Lys
1 5

(2) INFORMATION FOR SEQ ID NO: 70:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 70:

CAAAGGAAGA GTAGCTGTTA 20

(2) INFORMATION FOR SEQ ID NO: 71:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 71:

Val Asn Val Ser Leu Glu Asn Val Thr
1 5

(2) INFORMATION FOR SEQ ID NO: 72:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 72:

CAATGTTAGC TTGGAAAATG TCACC 25

(2) INFORMATION FOR SEQ ID NO: 73:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 73:

Thr Ala Phe Ile Gln Val Gly Glu
1 5

(2) INFORMATION FOR SEQ ID NO: 74:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 74:

AGCATTTATT CAAGTAGGAG 20

(2) INFORMATION FOR SEQ ID NO: 75:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 75:

Tyr Leu Leu Ser Thr Ser Ser
1 5

(2) INFORMATION FOR SEQ ID NO: 76:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 76:

TCTACTTTCC ACGTCCTCT 19

(2) INFORMATION FOR SEQ ID NO: 77:

(i) SEQUENCE CHARACTERISTICS:

(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 77:

Gln Ile Gln Pro Gln Gln Arg
1 5

(2) INFORMATION FOR SEQ ID NO: 78:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 78:

CAGATACAAC CGCAACAGC 19

(2) INFORMATION FOR SEQ ID NO: 79:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 79:

Pro Gln Gln Arg Ser Thr Gln Ser
1 5

(2) INFORMATION FOR SEQ ID NO: 80:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 80:

CCGCAACAGC GTTCAACTCA ATC 23

(2) INFORMATION FOR SEQ ID NO: 81:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 81:

Asp Gly Ala Ile Val Ala Trp
1 5

(2) INFORMATION FOR SEQ ID NO: 82:

(i) SEQUENCE CHARACTERISTICS:
(A) LENGTH: 21 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 82:

GACGGTGCGA TTGTTGCCTG G 21

(2) INFORMATION FOR SEQ ID NO: 83:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 83:

Glu Gly Asp Ser Gly Thr Val
1 5

(2) INFORMATION FOR SEQ ID NO: 84:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 84:

GAAGGAGACT CAGGTACTG 19

(2) INFORMATION FOR SEQ ID NO: 85:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 85:

Thr Val Thr Asn Thr Ser
1 5

(2) INFORMATION FOR SEQ ID NO: 86:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 86:

CCGTAACCAA TACAAGCAC 19

(2) INFORMATION FOR SEQ ID NO: 87:

(i) SEQUENCE CHARACTERISTICS:
(A) LENGTH: 9 amino acids
(B) TYPE: amino acid
(C) STRANDEDNESS: single (D) TOPOLOGY: linear (ii) MOLECULE TYPE: peptide (xi) SEQUENCE DESCRIPTION: SEQ ID NO: 87:

Ser Ser Gln Leu Ala Tyr Asn Pro Ser
1 5

(2) INFORMATION FOR SEQ ID NO: 88:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 88:

CTTCACAATT AGCGTATAAT CCTTC 25

(2) INFORMATION FOR SEQ ID NO: 89:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 89:

Glu Gln His Lys Glu Val Ala
1 5

(2) INFORMATION FOR SEQ ID NO: 90:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 90:

GAGCAGCATA AGGAAGTAG 19

(2) INFORMATION FOR SEQ ID NO: 91:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 91:

Phe Asn Gly Ile Gln Ile Val Pro
1 5

(2) INFORMATION FOR SEQ ID NO: 92:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 92:

CATTCAATGG GATTCAAATT GTTCC 25

(2) INFORMATION FOR SEQ ID NO: 93:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 93:

Val Gln Glu Ser Asn Gly Gly Gly
1 5

(2) INFORMATION FOR SEQ ID NO: 94:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 94:

GTGCAGGAAT CTAATGGTGG AGG 23

(2) INFORMATION FOR SEQ ID NO: 95:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 95:

Glu Ile Gly Gly Lys Phe Thr Leu Asn
1 5

(2) INFORMATION FOR SEQ ID NO: 96:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 96:

GATAGGAGGG AAATTTACAT TG 22

(2) INFORMATION FOR SEQ ID NO: 97:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 97:

TGAAT GCCGCTTTG 19

(2) INFORMATION FOR SEQ ID NO: 98:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 98:

CTCAAAACTK TTTGCTGGCA CC 22

(2) INFORMATION FOR SEQ ID NO: 99:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 99:

GGATCRAGCA ACCTCTCTAG 20

(2) INFORMATION FOR SEQ ID NO: 100:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 100:

ACTACTTACT TCTAGTAG 18

(2) INFORMATION FOR SEQ ID NO: 101:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 101:

Ser Asp Gln Gln Val Val Ile Glu
1 5

(2) INFORMATION FOR SEQ ID NO: 102:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 102:

CCGAYCRACA KGTCRTRATT G 21

(2) INFORMATION FOR SEQ ID NO: 103:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 103:

Asn Gln Thr Ser Met Thr Glu
1 5

(2) INFORMATION FOR SEQ ID NO: 104:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 104:

TCARDCTTCT ATGACAGMAC C 21

(2) INFORMATION FOR SEQ ID NO: 105:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 105:

Gln Asp Gln Glu Lys Ile Ile Pro
1 5

(2) INFORMATION FOR SEQ ID NO: 106:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 106:

CAAGATCAAG ARAARMTYAT YCCT 24

(2) INFORMATION FOR SEQ ID NO: 107:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 107:

Ser His Lys Gln Asp Gln Glu
1 5

(2) INFORMATION FOR SEQ ID NO: 108:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 108:

CTCRTMAACA AGATCAAG 18

(2) INFORMATION FOR SEQ ID NO: 109:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 109:

Ser Gly Ser Val Thr Ala His
1 5

(2) INFORMATION FOR SEQ ID NO: 110:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 110:

CTGGAARYGT SACGGCTC 18

(2) INFORMATION FOR SEQ ID NO: 111:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 111:

GCTTAGTATC TACTTTAAAG AG 22

(2) INFORMATION FOR SEQ ID NO: 112:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 112:

GATACTATTT GATAAGTTCT CATC 24

(2) INFORMATION FOR SEQ ID NO: 113:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 113:

CTTTTGGCCT TTTTGCGAAA TAAC 24

(2) INFORMATION FOR SEQ ID NO: 114:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 114:

CTGGGTTTAA CGCTTTATCA GATTGATATT C 31

(2) INFORMATION FOR SEQ ID NO: 115:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 115:

ACTTTTATTG CTAAACARGC TGC 23

(2) INFORMATION FOR SEQ ID NO: 116:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 116:

TAACAGCTAC TCTTCCTTTG 20

(2) INFORMATION FOR SEQ ID NO: 117:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 117:

GGTGACATTT TCCAAGCTAA CATTG 25

(2) INFORMATION FOR SEQ ID NO: 118:

(i) SEQUENCE CHARACTERISTICS:
(A) LENGTH: 19 base pairs
(B) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO: 118:

AGAGGACGTG GAAAGTAGA 19

(2) INFORMATION FOR SEQ ID NO: 119:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 119:

GCTGTTGCGG TTGTATCTG 19

(2) INFORMATION FOR SEQ ID NO: 120:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 120:

GATTGAGTTG AACGCTGTTG CGG 23

(2) INFORMATION FOR SEQ ID NO: 121:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 121:

CCAGGCAACA ATCGCACCGT C 21

(2) INFORMATION FOR SEQ ID NO: 122:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 122:

CAGTACCTGA GTCTCCTTC 19

(2) INFORMATION FOR SEQ ID NO: 123:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 123:

GTGCTTGTAT TGGTTACGG 19

(2) INFORMATION FOR SEQ ID NO: 124:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 124:

GAAGGATTAT ACGCTAATTG TGAAG 25

(2) INFORMATION FOR SEQ ID NO: 125:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 125:

GGAACAATTT GAATCCCATT GAATG 25

(2) INFORMATION FOR SEQ ID NO: 126:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 126:

CCTCCACCAT TAGATTCCTG CAC 23

(2) INFORMATION FOR SEQ ID NO: 127:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 127:

CAATGTAAAT TTCCCTCCTA TC 22

(2) INFORMATION FOR SEQ ID NO: 128:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 128:

GGTGCCAGCA AAMAGTTTTG AG 22

(2) INFORMATION FOR SEQ ID NO: 129:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 129:

CTAGAGAGGT TGCTYGATCC 20

(2) INFORMATION FOR SEQ ID NO: 130:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 130:

CTACTAGAAG TAAGTAGT 18

(2) INFORMATION FOR SEQ ID NO: 131:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 131:

GGTKCTGTCA TAGAAGHYTG A 21

(2) INFORMATION FOR SEQ ID NO: 132:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 132:

AGGRATRAKY TTYTCTTGAT CTTG 24

(2) INFORMATION FOR SEQ ID NO: 133:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 133:

CTTGATCTTG TTKAYGAG 18

(2) INFORMATION FOR SEQ ID NO: 134:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 134:

GAGCCGTSAC RYTTCCAG 18

(2) INFORMATION FOR SEQ ID NO: 135:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 135:

CCAGTCCAAT GAACCTCTTA C 21

(2) INFORMATION FOR SEQ ID NO: 136:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 136:

AGGGAACAAA CCTTCCCAAC C 21

(2) INFORMATION FOR SEQ ID NO: 137:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 137:

CARMTAKTAA MTAGGGATAG 20

(2) INFORMATION FOR SEQ ID NO: 138:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 138:

AGYTTCTATC GAAGCTGGGR ST 22

(2) INFORMATION FOR SEQ ID NO: 139:

(i) SEQUENCE CHARACTERISTICS:
(A) LENGTH: 1035 base pairs
(B) TYPE: nucleic acid
(C) STRANDEDNESS: single -continued (D) TOPOLOGY: linear (ii) MOLECULE TYPE: DNA (genomic)

(xi) SEQUENCE DESCRIPTION: SEQ ID NO: 139:

```
GGGTTAATTG GGTATTATTT TAAAGGGAAA GATTTTAATA ATCTGACTAT GTTTGCACCA     60
ACCATAAATA ATACGCTTAT TTATGATCGG CAAACAGCAG ATACACTATT AAATAAGCAG    120
CAACAAGAGT TCAATTCTAT TCGATGGATT GGTTTAATAC AAAGTAAAGA AACAGGTGAC    180
TTTACATTCC AATTATCAGA TGATAAAAAT GCCATCATTG AAATAGATGG AAAAGTTGTT    240
TCTCGTAGAG GAGAAGATAA ACAAACTATC CATTTAGAAA AAGGAAAGAT GGTTCCAATC    300
AAAATTGAGT ACCAGTCCAA TGAACCTCTT ACTGTAGATA GTAAAGTATT TAACGATCTT    360
AAACTATTTA AAATAGATGG TCATAATCAA TCGCATCAAA TACAGCAAGA TGATTTGAAA    420
ATCCTGAATT TAATAAAAAG GAAACGAAAG AGCTTTTATC AAAAACAGCA AAAAGAACCT    480
TTTCTCTTCA AAACGGGGTT GAGAAGCGAT GAGGATGATG ATCTAGGATA CAGATGGTGA    540
TAGCATTCCT GGATAATTGG GAAATGAATG GATATACCAT TCAAACGAAA AATGGCAGTC    600
AAATGGGATG ATTCATTTGC AGAAAAAGGA TATACAAAAT TTGTTTCGAA TCCATATGAA    660
GCCCATACAG CAGGAGATCC TTATACCGAT TATGAAAAAG CAGCAAAAGA TATTCCTTTA    720
TCGAACGCAA AAGAAGCCTT TAATCCTCTT GTAGCTGCTT TTCCATCTGT CAATGTAGGA    780
TTAGAAAAAG TAGTAATTTC TAAAAATGAG GATATGAGTC AGGGTGTATC ATCCAGCACT    840
TCGAATAGTG CCTCTAATAC AAATTCAATT GGTGTTACCG TAGATGCTGG TTGGGAAGGT    900
TTGTTCCCTA AATTTGGTAT TTCAACTAAT TATCAAAACA CATGGACCAC TGCACAAGAA    960
TGGGGCTCTT CTAAAGAAGA TTCTACCCAT ATAAATGGAG CACAATCAGC CTTTTTAAAT   1020
GCAAATGTAC GATAT                                                   1035
```

(2) INFORMATION FOR SEQ ID NO: 140:

(i) SEQUENCE CHARACTERISTICS:
(A) LENGTH: 345 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 140:

```
Gly Leu Ile Gly Tyr Tyr Phe Lys Gly Lys Asp Phe Asn Asn Leu Thr
1               5                   10                  15

Met Phe Ala Pro Thr Ile Asn Asn Thr Leu Ile Tyr Asp Arg Gln Thr
            20                  25                  30

Ala Asp Thr Leu Leu Asn Lys Gln Gln Gln Glu Phe Asn Ser Ile Arg
        35                  40                  45

Trp Ile Gly Leu Ile Gln Ser Lys Glu Thr Gly Asp Phe Thr Phe Gln
    50                  55                  60

Leu Ser Asp Asp Lys Asn Ala Ile Ile Glu Ile Asp Gly Lys Val Val
65                  70                  75                  80

Ser Arg Arg Gly Glu Asp Lys Gln Thr Ile His Leu Glu Lys Gly Lys
                85                  90                  95

Met Val Pro Ile Lys Ile Glu Tyr Gln Ser Asn Glu Pro Leu Thr Val
            100                 105                 110

Asp Ser Lys Val Phe Asn Asp Leu Lys Leu Phe Lys Ile Asp Gly His
        115                 120                 125
```

-continued

```
Asn Gln Ser His Gln Ile Gln Gln Asp Asp Leu Lys Ile Leu Asn Leu
    130                 135                 140

Ile Lys Arg Lys Arg Lys Ser Phe Tyr Gln Lys Gln Gln Lys Glu Pro
145                 150                 155                 160

Phe Leu Phe Lys Thr Gly Leu Arg Ser Asp Glu Asp Asp Asp Leu Gly
                165                 170                 175

Tyr Arg Trp Xaa Xaa His Ser Trp Ile Ile Gly Lys Xaa Met Asp Ile
            180                 185                 190

Pro Phe Lys Arg Lys Met Ala Val Lys Trp Asp Asp Ser Phe Ala Glu
        195                 200                 205

Lys Gly Tyr Thr Lys Phe Val Ser Asn Pro Tyr Glu Ala His Thr Ala
    210                 215                 220

Gly Asp Pro Tyr Thr Asp Tyr Glu Lys Ala Ala Lys Asp Ile Pro Leu
225                 230                 235                 240

Ser Asn Ala Lys Glu Ala Phe Asn Pro Leu Val Ala Ala Phe Pro Ser
                245                 250                 255

Val Asn Val Gly Leu Glu Lys Val Val Ile Ser Lys Asn Glu Asp Met
            260                 265                 270

Ser Gln Gly Val Ser Ser Ser Thr Ser Asn Ser Ala Ser Asn Thr Asn
        275                 280                 285

Ser Ile Gly Val Thr Val Asp Ala Gly Trp Glu Gly Leu Phe Pro Lys
    290                 295                 300

Phe Gly Ile Ser Thr Asn Tyr Gln Asn Thr Trp Thr Thr Ala Gln Glu
305                 310                 315                 320

Trp Gly Ser Ser Lys Glu Asp Ser Thr His Ile Asn Gly Ala Gln Ser
                325                 330                 335

Ala Phe Leu Asn Ala Asn Val Arg Tyr
            340                 345
```

(2) INFORMATION FOR SEQ ID NO: 141:

(i) SEQUENCE CHARACTERISTICS:
(A) LENGTH: 1037 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 141:

```
GGGTTAATTG GGTATTATTT TAAAGGGAAA GATTTTAATA ATCTGACTAT GTTTGCACCA     60

ACCATAAATA ATACGCTTAT TTATGATCGG CAAACAGCAG ATACACTATT AAATAAGCAG    120

CAACAAGAGT TCAATTCTAT TCGATGGATT GGTTTAATAC AAAGTAAAGA AACAGGTGAC    180

TTTACATTCC AATTATCAGA TGATAAAAAT GCCATCATTG AAATAGATGG AAAAGTTGTT    240

TCTCGTAGAG GAGAAGATAA ACAAACTATC CATTTAGAAA AAGGAAAGAT GGTTCCAATC    300

AAAATTGAGT ACCAGTCCAA TGAACCTCTT ACTGTAGATA GTAAAGTATT TAACGATCTT    360

AAACTATTTA AAATAGATGG TCATAATCAA TCGCATCAAA TACAGCAAGA TGATTTGAAA    420

AATCCTGAAT TTAATAAAAA AGAAACGAAA GAGCTTTTAT CAAAAACAGC AAAAAGRAAC    480

CTTTTCTCTT CAAACGRRGT KGAGAAGCGA TGAGGATGAT RATCYTAGAT ACAGGTGGKG    540

ATAGCATTCC YKGATAATTG GGGAAATGAA WGGRTATACC ATTCAACSGA AAAATGGSAG    600

TCAAATGGGA TGATTCATTT GCGGAAAAAG GATATACAAA ATTTGTTTCG AATCCATATG    660

AAGCCCATAC AGCAGGAGAT CCTTATACCG ATTATGAAAA AGCAGCAAAA GATATTCCTT    720
```

-continued

```
TATCGAACGC AAAAGAAGCC TTTAATCCTC TTGTAGCTGC TTTTCCATCT GTCAATGTAG    780

GATTAGAAAA AGTAGTAATT TCTAAAAATG AGGATATGAG TCAGGGTGTA TCATCCAGCA    840

CTTCGAATAG TGCCTCTAAT ACAAATTCAA TTGGTGTTAC CGTAGATGCT GGTTGGGAAG    900

GTTTGTTCCC TAAATTTGGT ATTTCAACTA ATTATCAAAA CACATGGACC ACTGCACAAG    960

AATGGGGCTC TTCTAAAGAA GATTCTACCC ATATAAATGG AGCACAATCA GCCTTTTTAA   1020

ATGCAAATGT ACGATAT                                                 1037
```

(2) INFORMATION FOR SEQ ID NO: 142:

(i) SEQUENCE CHARACTERISTICS:
(A) LENGTH: 1048 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 142:

```
TGGGTTAATT GGGTATTATT TTAAAGGGCA AGAGTTTAAT CATCTTACTT TGTTCGCACC     60

AACACGTGAT AATACCCTTA TTTATGATCA ACAAACAGCG AATTCCTTAT TAGATACCAA    120

GCAACAAGAA TATCAATCTA TTCGCTGGAT TGGTTTAATT CAAAGTAAAG AAACGGGTGA    180

TTTCACATTT AACTTATCAG ATGATCAACA TGCAATTATA GAAATCGATG GCAAAATCAT    240

TTCGCATAAA GGACAGAATA AACAAGTTGT TCACTTAGAA AAAGGAAAGT TAGTCCCGAT    300

AAAAATTGAG TATCAATCAG ATCAACTATT AAATAGGGAT AGTAACATCT TTAAAGAGTT    360

TAAATTATTC AAAGTAGATA GTCAGCAACA CGCTCACCAA GTTCAACTAG ACGAATTAAG    420

AAACCCTGCG TTTAATAAAA AGGAAACACA ACAATCTTAA GAAAAAGCAT CCAAAAACAA    480

TCTTTTTACA CCAGGGACAT TAAAAGGAAG ATACTGATGA TGATGATAAG GATAACAGGA    540

TGGGAGATTC TATTCCTGGA CCTTTTGGGG GAAGAAAATG GGTATACCAA TCCCAAAATA    600

AAATAGCTGG TCCAAGTGGG ATGTTCATTC GCCGCGAAAG GGTATACAAA TTTGTTTCTT    660

AATCCACTTG ATAGTCATAC AGTTGGAGAT CCCTATACGG ATTATGAAAA AGCAGCAAGA    720

GATTTAGACT TGGCCCAATG CAAAAGAAAC ATTTAACCCA TTAGTAGCTG CTTTTCCAAG    780

TGTGAATGTG AATTTGGAAA AAGTCATTTT ATCTAAAGAT GAAAATCTAT CCAATAGTGT    840

AGAGTCACAT TCCTCCACCA ACTGGTCTTA TACGAATACA GAAGGAGCTT CTATCGAAGC    900

TGGGGCTAAA CCAGAGGGTC CTACTTTTGG AGTGAGTGCT ACTTATCAAC ACTCTGAAAC    960

AGTTGCAAAA GAATGGGGAA CATCTACAGG AAATACCTCG CAATTTAATA CAGCTTCAGC   1020

AGGATATTTA AATGCAAATG TACGATAT                                      1048
```

(2) INFORMATION FOR SEQ ID NO: 143:

(i) SEQUENCE CHARACTERISTICS:
(A) LENGTH: 1175 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 143:

```
ACCTCTAGAT GCANGCTCGA GCGGCCGCCA GTGTGATGGA TATCTGCAGA ATTCGGATTA     60

CTTGGGTATT ATTTTAAAGG GAAAGAGTTT AATCATCTTA CTTTGTTCGC ACCAACACGT    120

GATAATACCC TTATTTATGA TCAACAAACA GCGAATTCCT TATTAGATAC CAAACAACAA    180
```

-continued

```
GAATATCAAT CTATTCGCTG GATTGGTTTG ATTCAAAGTA AAGAAACAGG TGATTTCACG    240
TTTAACTTAT CTGATGATCA AAATGCAATT ATAGAAATAG ATGGCAAAAT CATTTCGCAT    300
AAAGGACAGA ATAAACAAGT TGTTCACTTA GAAAAAGGAA AGTTAGTCCC GATAAAAATT    360
GAGTATCAAT CAGATCAGAT ATTAACTAGG GATAGTAACA TCTTTAAAGA GTTCAATTAT    420
TCAAAGTAGA TAGTCAAGCA ACACTCTCAC CAAAGTTCAA CTTAGGNCNG AATTAAGNAA    480
CCCTNGGATT TTAANTTNAA AAAAAGGAAC CCNCANCATT CTTTAGGAAA AAGCAGCAAN    540
AACCAAATCC TTTTTTACCA CAGGATATTG AAAAGGAGAT ACGGGNTNGA TGATGGATTG    600
ATACCGGGAT ACCAGTTGGG GNTTCTANTC CCTGACCTTT GGGGAAAGAA AATNGGTATA    660
CCNATCCCAA AANTTAAGCC AGCTGTCCAG GTGGGATGAT TCAATTCGCC CGCGAAAGGG    720
TATACCAAAA TTTGTTTCTT AATCCACTTG AGAGTCATAC AGTTGGAGAT CCCTATACGG    780
ATTATGAAAA AGCAGCAAGA GATTTAGACT TGGCCAATGC AAAAGAAACA TTTAACCCAT    840
TAGTAGCTGC TTTTCCAAGT GTGAATGTGA ATTTGGAAAA AGTAATATTA TCCCCAGATG    900
AGAATTTATC TAACAGTGTA GAATCTCATT CGTCTACAAA TTGGTCTTAT ACGAATACTG    960
AAGGAGCTTC TATCGAAGCT GGGGGTGGTC CATTAGGTAT TTCATTTGGA GTGAGTGCTA   1020
ATTATCAACA CTCTGAAACA GTTGCAAAAG AATGGGGAAC ATCTACAGGA AATACCTCGC   1080
AATTTAATAC AGCTTCAGCA GGATATTTAA ATGCCAATGG TCGATNTAAG CCGAATNCCA   1140
NCACACTGNC GGCCGTTAGT AGTGGCACCG AGCCC                              1175
```

(2) INFORMATION FOR SEQ ID NO: 144:

(i) SEQUENCE CHARACTERISTICS:
(A) LENGTH: 1030 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 144:

```
GGRTTAMTTG GGTATTATTT TAAAGGGAAA GATTTTAATG ATCTTACTGT ATTTGCACCA     60
ACGCGTGGGA ATACTCTTGT ATATGATCAA CAAACAGCAA ATACATTACT AAATCAAAAA    120
CAACAAGACT TTCAGTCTAT TCGTTGGGTT GGTTTAATTC AAAGTAAAGA AGCAGGCGAT    180
TTTACATTTA ACTTATCAGA TGATGAACAT ACGATGATAG AAATCGATGG GAAAGTTATT    240
TCTAATAAAG GGAAAGAAAA ACAAGTTGTC CATTTAGAAA AAGGACAGTT CGTTTCTATC    300
AAAATAGAAT ATCAAGCTGA TGAACCATTT AATGCGGATA GTCAAACCTT TAAAAATTTG    360
AAACTCYTTA AAGTAGATAC TAAGCAACAG TCCCAGCAAA TTCAACTAGA TGAATTAAGA    420
AACCCTGRAA TTTAATAAAA AAGAAACACA AGAATTTCTA ACAAAAGCAA CAAAAACAAA    480
CCTTATTACT CAAAAAGTGA AGAGTACTAG GGATGAAGAC ACGGATACAG ATGGAGATTC    540
TATTCCAGAC ATTTGGGAAG AAAATGGGTA TACCATCCAA AATAAGATTG CCGTCAAATG    600
GGATGATTCA TTAGCAAGTA AAGGATATAC GAAATTTGTT TCAAACCCAC TAGATACTCA    660
CACGGTTGGA GATCCTTATA CAGATTATGA AAAAGCAGCA AGGGATTTAG ATTTGTCAAA    720
TGCAAAAGAA ACATTTAACC CATTAGTTGC GGCTTTTCCA AGTGTGAATG TGAGTATGGA    780
AAAAGTGATA TTGTCTCCAG ATGAGAACTT ATCAAATAGT ATCGAGTCTC ATTCATCTAC    840
GAATTGGTCG TATACGAATA CAGAAGGGGC TTCTATTGAA GCTGGTGGGG GAGCATTAGG    900
CCTATCTTTT GGTGTAAGTG CAAACTATCA ACATTCTGAA ACAGTTGGGT ATGAATGGGG    960
```

-continued

```
AACATCTACG GGAAATACTT CGCAATTTAA TACAGCTTCA GCGGGGTATT TAAATGCCAA   1020

TRTAMGATAT                                                          1030
```